United States Patent
Yokoyama et al.

(10) Patent No.: US 9,553,272 B2
(45) Date of Patent: Jan. 24, 2017

(54) ORGANIC ELECTROLUMINESCENT DEVICE

(75) Inventors: Norimasa Yokoyama, Tokyo (JP); Eiji Takahashi, Ibaraki (JP); Shuichi Hayashi, Ibaraki (JP); Daizou Kanda, Tokyo (JP); Hiroshi Ookuma, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 446 days.

(21) Appl. No.: 14/008,708

(22) PCT Filed: Apr. 17, 2012

(86) PCT No.: PCT/JP2012/060374
§ 371 (c)(1),
(2), (4) Date: Sep. 30, 2013

(87) PCT Pub. No.: WO2012/147568
PCT Pub. Date: Nov. 1, 2012

(65) Prior Publication Data
US 2014/0021451 A1  Jan. 23, 2014

(30) Foreign Application Priority Data
Apr. 25, 2011 (JP) ................. 2011-096744

(51) Int. Cl.
*H01L 51/00* (2006.01)
*C07D 471/04* (2006.01)
*H01L 51/50* (2006.01)

(52) U.S. Cl.
CPC ......... *H01L 51/0059* (2013.01); *C07D 471/04* (2013.01); *H01L 51/0052* (2013.01);
(Continued)

(58) Field of Classification Search
None
See application file for complete search history.

(56) References Cited

U.S. PATENT DOCUMENTS

| | | | |
|---|---|---|---|
| 4,720,432 A | 1/1988 | VanSlyke et al. | |
| 2008/0152950 A1 | 6/2008 | Je et al. | |

(Continued)

FOREIGN PATENT DOCUMENTS

| | | |
|---|---|---|
| CN | 101506207 | 8/2009 |
| JP | 6-314594 | 11/1994 |

(Continued)

OTHER PUBLICATIONS

U.S. Appl. No. 14/000,406 to Norimasa Yokoyama et al., filed Aug. 20, 2013.

(Continued)

*Primary Examiner* — J. L. Yang
(74) *Attorney, Agent, or Firm* — Greenblum & Bernstein, P.L.C.

(57) ABSTRACT

An organic electroluminescent device comprises, between an anode and a cathode, a hole injection layer, a hole-transporting layer, a luminous layer and an electron-transporting layer, wherein the hole injection layer contains an arylamine compound (α) having three or more triphenylamine skeletons, the hole-transporting layer contains an arylamine compound (β) having two triphenylamine skeletons, and the electron-transporting layer contains an electron-transporting compound having an anthracene ring skeleton and a pyridoindole ring skeleton. The organic EL device emits light highly efficiently, drives on a low voltage, and features excellent durability and long life.

15 Claims, 1 Drawing Sheet

8: CATHODE
7: ELECTRON INJECTION LAYER
6: ELECTRON-TRANSPORTING LAYER
5: LUMINOUS LAYER
4: HOLE-TRANSPORTING LAYER
3: HOLE INJECTION LAYER
2: TRANSPARENT ELECTRODE
1: GLASS SUBSTRATE

(52) U.S. Cl.
CPC ...... *H01L 51/0072* (2013.01); *H01L 51/5056* (2013.01); *H01L 51/5072* (2013.01); *H01L 51/5088* (2013.01)

(56) References Cited

U.S. PATENT DOCUMENTS

| | | |
|---|---|---|
| 2009/0230857 A1 | 9/2009 | Choi et al. |
| 2010/0230660 A1 | 9/2010 | Yokoyama et al. |
| 2011/0073852 A1 | 3/2011 | Yokoyama et al. |
| 2011/0175079 A1 | 7/2011 | Yokoyama et al. |
| 2012/0228598 A1 | 9/2012 | Yokoyama et al. |
| 2013/0328040 A1 | 12/2013 | Yokoyama et al. |

FOREIGN PATENT DOCUMENTS

| | | |
|---|---|---|
| JP | 8-291115 | 11/1996 |
| JP | 3529735 | 3/2004 |
| TW | 201000596 | 1/2010 |
| TW | 201022261 | 6/2010 |
| WO | 2009/099133 | 8/2009 |
| WO | 2009/139475 | 11/2009 |
| WO | 2010/035723 | 4/2010 |
| WO | 2010/114256 | 10/2010 |
| WO | 2011/059000 | 5/2011 |

OTHER PUBLICATIONS

International Search Report in PCT/JP2012/060374 mailed on Jun. 26, 2012.
E.P.O. Office action, mail date is Nov. 24, 2014.
Extended European Search Report issued in Patent Application No. 12775988.4, dated Jan. 25, 2016.
Taiwanese Office Action issued in Patent Appl. No. 101114551, dated Mar. 2, 2016.

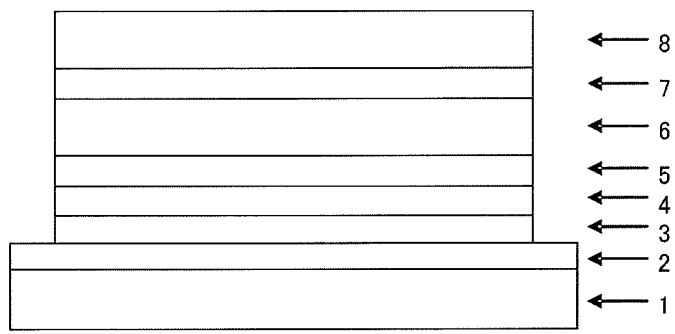
8: CATHODE
7: ELECTRON INJECTION LAYER
6: ELECTRON-TRANSPORTING LAYER
5: LUMINOUS LAYER
4: HOLE-TRANSPORTING LAYER
3: HOLE INJECTION LAYER
2: TRANSPARENT ELECTRODE
1: GLASS SUBSTRATE

ORGANIC ELECTROLUMINESCENT DEVICE

TECHNICAL FIELD

This invention relates to an organic electroluminescent device which is a spontaneously luminescent device suited for use in various kinds of display devices. More specifically, the invention relates to an organic electroluminescent device (hereinafter often abbreviated as organic EL device) using plural kinds of arylamine compounds as a hole injection material, and a compound having an anthracene ring skeleton and a pyridoindole ring skeleton as an electron-transporting material.

BACKGROUND ART

An organic EL device is a spontaneously luminous device which features higher brightness and higher legibility than those of the liquid crystal devices enabling vivid display to be attained and has, therefore, been vigorously studied.

In 1987, C. W. Tang et al. of the Eastman Kodak Co. have developed a device of a layer-laminated structure comprising various kinds of materials to bear individual roles, and have put an organic EL device using organic materials into a practical use. The above organic EL device is constituted by laminating a fluorescent body capable of transporting electrons and an organic material capable of transporting holes. Upon injecting both electric charges into the layer of the fluorescent body to emit light, the device is capable of attaining a brightness of as high as 1000 cd/m$^2$ or more with a voltage of not higher than 10 V.

So far, very many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, to improve the luminous efficiency, to lower the driving voltage and to lengthen the life, it is necessary that the device has excellent carrier balance enabling the electrons and holes to be efficiently injected and transported, and enabling them to be efficiently recombined together.

As the hole injection material used for the organic EL device, there were, first, proposed phthalocyanines such as copper phthalocyanine (CuPc) (e.g., see a patent document 1) accompanied, however, by an absorption in the visible band. Therefore, materials having a phenylenediamine structure have now been widely used (see a patent document 2).

As the hole-transporting material, on the other hand, arylamine materials having a benzidine skeleton have heretofore been used (see a patent document 3).

Tris(8-hydroxyquinoline) aluminum (Alq$_3$) which is a representative luminous material has been generally used as the electron-transporting material. However, the electron mobility possessed by the Alq$_3$ is lower than the hole mobility possessed by the hole-transporting material that is generally used. Besides, the work function of the Alq$_3$ is 5.8 eV which cannot be said to be a sufficiently large hole blocking power. Therefore, use of the above hole-transporting material is accompanied by a problem in that the holes partly pass through the luminous layer to deteriorate the efficiency.

In order to efficiently inject the holes or the electrons from the anode and cathode into the luminous layer, further, there has been developed a device obtained by laminating the hole injection layers and the electron injection layers each in a number of two or more layers to set stepwise the ionization potential values and the values of electron affinity possessed by the materials (see a patent document 4). With the materials that are used, however, none of the luminous efficiency, driving voltage or device life is still satisfactory.

At present, in order to improve properties of the organic EL devices, attempts have been made to attain a high efficiency, a low driving voltage and a long life maintaining good carrier balance by using in combination materials that excel in hole and electron injection/transport property and in maintaining stability and durability in the form of thin films.

PRIOR ART DOCUMENTS

Patent Documents

Patent document 1: U.S. Pat. No. 4,720,432
Patent document 2: JP-A-8-291115
Patent document 3: Japanese Patent No. 3529735
Patent document 4: JP-A-6-314594

OUTLINE OF THE INVENTION

Problems that the Invention is to Solve

The object of the present invention is to provide an organic EL device that features a high efficiency, a low driving voltage and a long life by using in combination various kinds of materials for organic EL device that excel in hole and electron injection/transport property, and stability and durability in the form of thin films so that the properties possessed by the respective materials can be effectively exhibited.

Means for Solving the Problems

To achieve the above object, therefore, the present inventors have paid attention to that the arylamine type materials have excellent hole injection and transporting properties, stability and durability in the form of thin films, have selected two kinds of specific arylamine compounds, and have so combined them together that the holes could be efficiently injected into, and transported by, the luminous layer. As a result, the inventors have discovered that a compound having an anthracene ring skeleton and a pyridoindole ring skeleton exhibits excellent electron injection/transport capability, excellent stability and durability in the form of a thin film. Therefore, the inventors have used the above arylamine compounds in combination as an electron-transporting material and have completed the device of the invention.

According to the present invention, there is provided an organic electroluminescent device comprising, between an anode and a cathode, a hole injection layer, a hole-transporting layer, a luminous layer and an electron-transporting layer, wherein:

the hole injection layer contains an arylamine compound (α) having a molecular structure in which three or more triphenylamine skeletons are bonded together via a single bond or a divalent hydrocarbon group;

the hole-transporting layer contains an arylamine compound (β) having a molecular structure in which two triphenylamine skeletons are bonded together via a single bond or a divalent hydrocarbon group; and the electron-transporting layer contains an electron-transporting compound having an anthracene ring skeleton and a pyridoindole ring skeleton represented by the following general formula (1) or the general formula (2).

The electron-transporting compound of the general formula (1);

[Chemical 1]

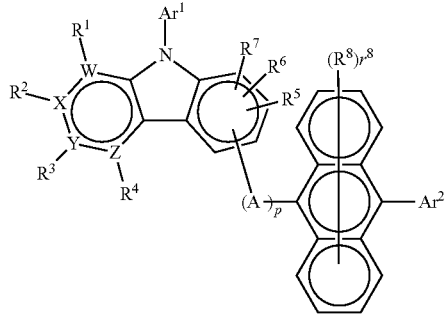

(1)

In the general formula (1), p represents the number of the divalent groups A, and is an integer of 0 to 4, A is a divalent unsubstituted or substituted aromatic hydrocarbon ring group or an aromatic heterocyclic group, and when p is 2 or larger, the plurality of As may be different from each other and when p is 0, A is not present, and the anthracene ring and the pyridoindole ring are bonded together via a single bond, $Ar^1$ is an unsubstituted or substituted aromatic hydrocarbon group or an aromatic heterocyclic group, $Ar^2$ is an unsubstituted or substituted aromatic hydrocarbon group, $R^1$ to $R^7$ are, respectively, hydrogen atoms, deuterium atoms, fluorine atoms, chlorine atoms, cyano groups, trifluoromethyl groups, unsubstituted alkyl groups having 1 to 6 carbon atoms, unsubstituted or substituted aromatic hydrocarbon groups or aromatic heterocyclic groups, $r^8$ which represents the number of $R^8$ is an integer of 0 to 8, $R^8$ is a deuterium atom, a fluorine atom, a chlorine atom, a cyano group, a trifluoromethyl group or an unsubstituted alkyl group having 1 to 6 carbon atoms, and when $r^8$ is a number of 2 or more, the plurality of $R^8$ may be the same or different, and W, X, Y and Z are, respectively, carbon atoms or nitrogen atoms, and when only any one of them is a nitrogen atom, none of $R^1$ to $R^4$ is bonded to the nitrogen atom.

The electron-transporting compound of the general formula (2);

[Chemical 2]

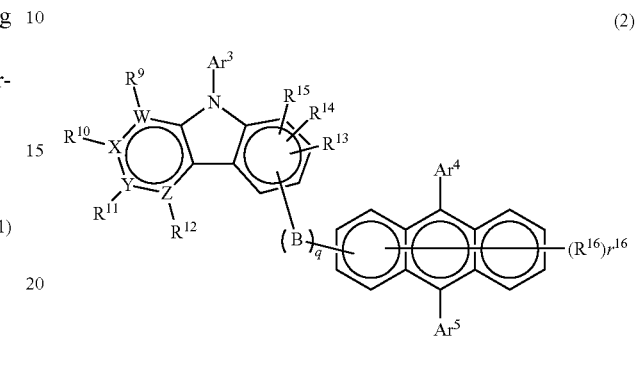

(2)

In the general formula (2), q represents the number of the divalent groups B, and is an integer of 0 to 4, B is a divalent unsubstituted or substituted aromatic hydrocarbon ring group or an aromatic heterocyclic group, and when q is 2 or larger, the plurality of Bs may be different from each other and when q is 0, B is not present, and the anthracene ring and the pyridoindole ring are bonded together via a single bond, $Ar^3$ is an unsubstituted or substituted aromatic hydrocarbon group or an aromatic heterocyclic group, $Ar^4$ and $Ar^5$ are unsubstituted or substituted aromatic hydrocarbon groups, $R^9$ to $R^{15}$ are, respectively, hydrogen atoms, deuterium atoms, fluorine atoms, chlorine atoms, cyano groups, trifluoromethyl groups, unsubstituted alkyl groups having 1 to 6 carbon atoms, unsubstituted or substituted aromatic hydrocarbon groups or aromatic heterocyclic groups, $r^{16}$ which represents the number of $R^{16}$ is an integer of 0 to 7, $R^{16}$ is a deuterium atom, a fluorine atom, a chlorine atom, a cyano group, a trifluoromethyl group or an unsubstituted alkyl group having 1 to 6 carbon atoms, and when $r^{16}$ is a number of 2 or more, the plurality of $R^{16}$ may be the same or different, and W, X, Y and Z are, respectively, carbon atoms or nitrogen atoms, and when only any one of them is a nitrogen atom, none of $R^9$ to $R^{12}$ is bonded to the nitrogen atom.

In the organic EL device of the invention, the arylamine compound (α) used for the hole injection layer, i.e., the arylamine compound (α) having a molecular structure in which three or more triphenylamine skeletons are bonded together via a single bond or a divalent hydrocarbon group, is, preferably, represented by the following general formula (3).

The arylamine compound (α) of the general formula (3),

[Chemical 3]

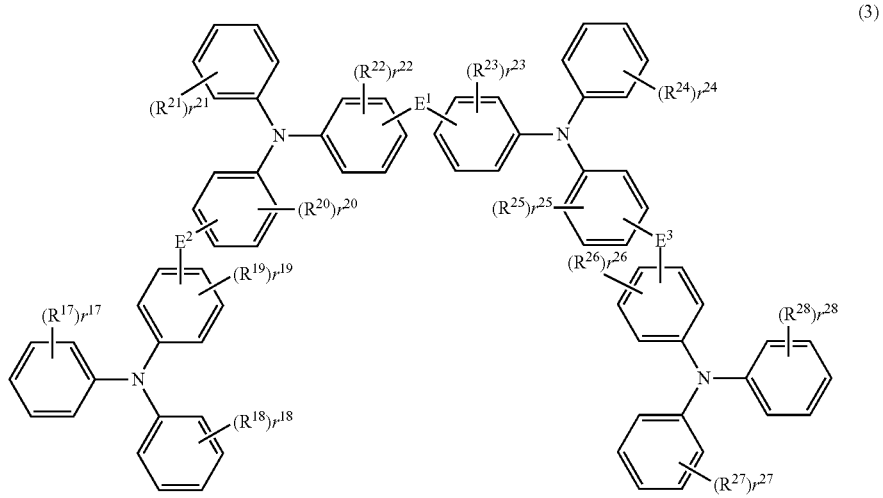

(3)

wherein,
$r^{17}$ to $r^{28}$, respectively, represent the numbers of $R^{17}$ to $R^{28}$;
$r^{17}$, $R^{18}$, $r^{21}$, $r^{24}$, $r^{27}$ and $r^{28}$ being integers of 0 to 5, and $r^{19}$, $r^{20}$, $r^{22}$, $r^{23}$, $r^{25}$ and $r^{26}$ being integers of 0 to 4,
$R^{17}$ to $R^{28}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups or aromatic heterocyclic groups and among these groups, the groups bonded to the same benzene ring may be bonded together to form a ring, and
$E^1$ to $E^3$, respectively, are single bonds or divalent groups represented by any one of the following formulas,

[Chemical 4]

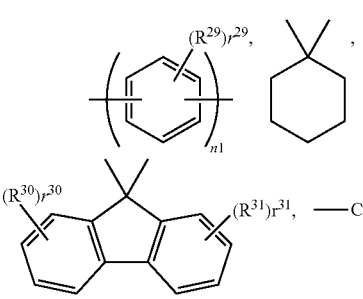

wherein,
n1 is an integer of 1 to 3,
$r^{29}$, $r^{30}$ and $r^{31}$ represent the numbers of $R^{29}$, $R^{30}$ and $R^{31}$, and are, respectively, integers of 0 to 4, and
$R^{29}$, $R^{30}$ and $R^{31}$ are the same atoms or the groups as those of the above $R^{17}$ to $R^{28}$.

In the organic EL device of the invention, the arylamine compound (β) used for the hole-transporting layer, i.e., the arylamine compound (β) having a molecular structure in which two triphenylamine skeletons are bonded together via a single bond or a divalent hydrocarbon group, is, preferably, represented by the following general formula (4).

The arylamine compound (β) of the general formula (4);

[Chemical 5]

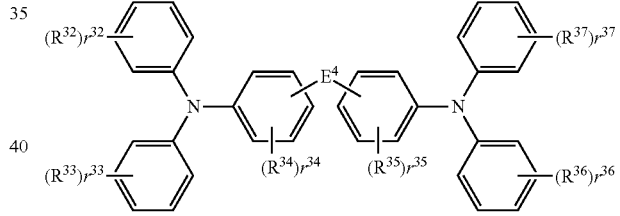

(4)

wherein,
among $r^{32}$ to $r^{37}$ representing the numbers of $R^{32}$ to $R^{37}$,
$r^{32}$, $r^{33}$, $r^{36}$ and $r^{37}$ are integers of 0 to
$r^{34}$ and $r^{35}$ are integers of 0 to 4,
$R^{32}$ to $R^{37}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups or aromatic heterocyclic groups and among these groups, the groups bonded to the same benzene ring may be bonded together to form a ring, and
$E^4$ is a single bond or a divalent group represented by any one of the following formulas,

[Chemical 6]

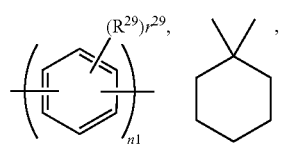

-continued

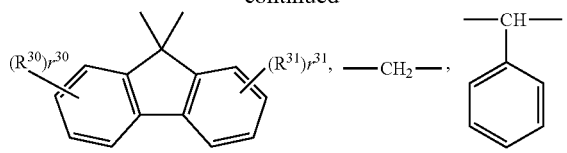

wherein, n1 is an integer of 1 to 3, $r^{29}$, $r^{30}$ and $r''$ represent the numbers of $R^{29}$, $R^{30}$ and $R^{31}$, and are, respectively, integers of 0 to 4, and $R^{29}$, $R^{30}$ and $R^{31}$ are the same atoms or the groups as those of the above $R^{17}$ to $R^{28}$.

Effects of the Invention

The organic EL device of the present invention has a distinguished feature in that the hole injection layer is formed by using the arylamine compound (α) that has three or more triphenylamine skeletons in a molecule thereof, the hole-transporting layer is formed by using the arylamine compound (β) that has two triphenylamine skeletons in a molecule thereof, and the electron-transporting layer is formed by using the electron-transporting compound that has an anthracene ring skeleton and a pyridoindole ring skeleton represented by the above general formula (1) or (2).

Namely, the present invention uses in combination the materials having excellent hole and electron injection/transport properties and excellent stability and durability in the form of thin films maintaining carrier balance. This improves, maintaining good balance, the efficiency for injecting holes into the hole injection layer, the efficiency for transporting holes from the hole-transporting layer to the luminous layer, and the efficiency for transporting electrons from the electron-transporting layer to the luminous layer. As a result, the organic EL device of the invention features a high luminous efficiency, a low driving voltage and excellent durability.

As described above, the present invention realizes an organic EL device that features improved luminous efficiency, decreased driving voltage and elongated service life.

BRIEF DESCRIPTION OF THE DRAWING

FIG. 1 is a view showing the laminated layer structure of organic EL devices fabricated in Examples 8 to 14 and Comparative Examples 1 and 2.

MODES FOR CARRYING OUT THE INVENTION

<Electron-Transporting Compounds>

In the invention, the electron-transporting layer is formed by using an electron-transporting compound that has an anthracene ring skeleton and a pyridoindole ring skeleton. Here, as described earlier, the electron-transporting compound is either the one that is represented by the general formula (1) or the one that is represented by the general formula (2).

General formula (1);
[Chemical 7]

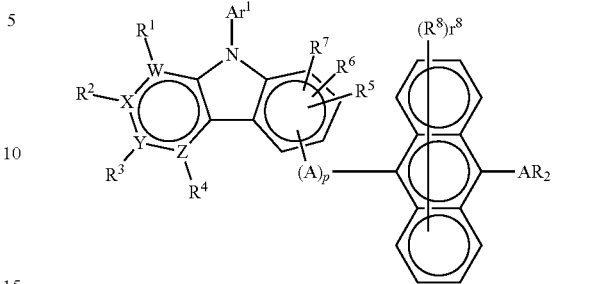

General formula (2);
[Chemical 8]

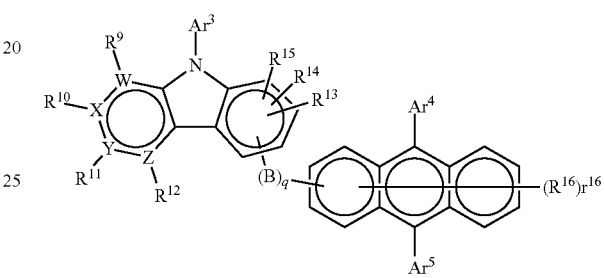

As will be understood from the above general formulas, the compound of the general formula (1) and the compound of the general formula (2) are different from each other in regard to only the position of the anthracene ring to where the pyridoindole ring is bonded, but have substantially the same structure in regard to other respects. Namely, the compound of the general formula (1) has the pyridoindole ring bonded to the 9-th or the 10-th position of the anthracene ring while the compound of the general formula (2) has a structure in which the pyridoindole ring is bonded to a position other than the 9-th or the 10-th position of the anthracene ring.

For instance, the atoms W, X, Y and Z forming part of the pyridoindole ring are in common between the two.

Further, p and the divalent group A in the general formula (1) correspond to q and the divalent group B in the general formula (2), and $Ar^1$ and $Ar^2$ in the general formula (1) correspond to $Ar^3$, $Ar^4$ and $Ar^5$ in the general formula (2). Further, $R^1$ to $R^8$ in the general formula (1) correspond to $R^9$ to $R^{16}$ in the general formula (2), and $r^8$ in the general formula (1) corresponds to $r^{16}$ in the general formula (2).

The groups in the general formulas (1) and (2) will be described below.

(Divalent Groups A, B and p, q)

In the above general formulas (1) and (2), p and q represent the numbers of the divalent groups A and B, and are integers of 0 to 4.

Namely, the electron-transporting compounds have a structure in which the anthracene ring and the pyridoindole ring are bonded together through the divalent group A or B. Here, when p or q is zero, there is present no divalent group A or B, and the anthracene ring and the pyridoindole ring are directly coupled together via a single bond. When a plurality of the divalent groups A or B are connected in series to bond the anthracene ring and the pyridoindole ring together (i.e., when p or q is 2 or more), the plurality of the groups A or B may be different from each other.

These divalent groups A and B are aromatic hydrocarbon ring groups or aromatic heterocyclic groups, and these ring groups may have a single ring structure or a condensed polycyclic structure.

As the aromatic hydrocarbon ring that forms the above ring group, there can be exemplified benzene ring, naphthalene ring, anthracene ring, phenanthrene ring, indene ring and pyrene ring while as the aromatic heterocyclic ring, there can be exemplified pyridine ring, pyrimidine ring, quinoline ring, isoquinoline ring, benzimidazole ring, pyrazole ring, carbazole ring, naphthylidine ring, phenanthridine ring and acridine ring.

The above aromatic hydrocarbon ring group and aromatic heterocyclic group may have a substituent so far as the electron-transporting capability of the compound is not impaired. As the substituent, there can be exemplified deuterium atom, fluorine atom, chlorine atom, cyano group, trifluoromethyl group, alkyl group having 1 to 6 carbon atoms, aromatic hydrocarbon group and aromatic heterocyclic group.

In the substituents, the alkyl group having 1 to 6 carbon atoms may be either a straight chain or branched, and its concrete examples include methyl group, ethyl group, n-propyl group, isopropyl group, n-butyl group, isobutyl group, tert-butyl group, n-pentyl group, isopentyl group, neopentyl group and n-hexyl group.

As the aromatic hydrocarbon group which is the substituent, there can be exemplified phenyl group, biphenylyl group, terphenylyl group, tetrakisphenyl group, styryl group, naphthyl group, anthryl group, acenaphthenyl group, fluorenyl group and phenanthryl group.

As the aromatic heterocyclic group in the above substituents, there can be exemplified indenyl group, pyrenyl group, pyridyl group, pyrimidyl group, furanyl group, pyrrolyl group, thienyl group, quinolyl group, isoquinolyl group, benzofuranyl group, benzothienyl group, indolyl group, carbazolyl group, benzoxazolyl group, benzthiazolyl group, quinoxalyl group, benzimidazolyl group, pyrazolyl group, dibenzofuranyl group, dibenzothienyl group, naphthylidinyl group, phenanthrolinyl group and acridinyl group.

The above substituents may, further, have a substituent.

Further, they may have a quinone structure. For instance, the fluorenone ring, too, may be the divalent group A or R.

($Ar^1$ and $Ar^3$)

$Ar^1$ in the general formula (1) and $Ar^3$ in the general formula (2) represent aromatic hydrocarbon groups or aromatic heterocyclic groups (which are monovalent groups) which may have a condensed polycyclic structure.

As the aromatic hydrocarbon group, there can be exemplified phenyl group, biphenylyl group, terphenylyl group, tetrakisphenyl group, styryl group, naphthyl group, anthryl group, acenaphthenyl group, fluorenyl group and phenanthryl group.

As the aromatic heterocyclic group, further, there can be exemplified indenyl group, pyrenyl group, pyridyl group, pyrimidyl group, furanyl group, pyrrolyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group, naphthyridinyl group, phenanthrolinyl group and acridinyl group.

The above aromatic hydrocarbon group and aromatic heterocyclic group, too, may have a substituent so far as the electron-transporting capability is not adversely affected. As the substituent, there can be exemplified deuterium atom, fluorine atom, chlorine atom, cyano group, trifluoromethyl group, hydroxyl group, nitro group, straight-chain or branched alkyl group having 1 to 6 carbon atoms, cyclopentyl group, cyclohexyl group, straight-chain or branched alkoxy group having 1 to 6 carbon atoms, dialkylamino group substituted by a straight-chain or branched alkyl group having 1 to 6 carbon atoms, phenyl group, naphthyl group, anthryl group, fluorenyl group, styryl group, pyridyl group, pyridoindolyl group, quinolyl group and benzothiazolyl group, which may, further, be substituted.

($Ar^2$ and $Ar^4$, $Ar^5$)

$Ar^2$ in the general formula (1) and $Ar^4$, $Ar^5$ in the general formula (2) represent aromatic hydrocarbon groups which, too, may have a condensed polycyclic structure.

As the aromatic hydrocarbon group, there can be exemplified the same groups as those exemplified concerning $Ar^1$ and $Ar^3$ above, i.e., phenyl group, biphenylyl group, terphenylyl group, tetrakisphenyl group, styryl group, naphthyl group, anthryl group, acenaphthenyl group, fluorenyl group and phenanthryl group.

These aromatic hydrocarbon groups, too, may have the same substituents as those exemplified concerning $Ar^1$ and $Ar^3$ above, and such substituents, too, may, further, have a substituent.

($R^1$ to $R^7$ and $R^9$ to $R^{15}$)

In the general formula (1), $R^1$ to $R^7$ are, respectively, hydrogen atoms, deuterium atoms, fluorine atoms, chlorine atoms, cyano groups, trifluoromethyl groups, unsubstituted alkyl groups having 1 to 6 carbon atoms, unsubstituted or substituted aromatic hydrocarbon groups or aromatic heterocyclic groups. $R^9$ to $R^{15}$ in the general formula (2), too, are the same as $R^1$ to $R^7$.

The above unsubstituted alkyl group having 1 to 6 carbon atoms is the same as the alkyl group that was exemplified above as the substituent which the above-mentioned divalent group A may have.

Further, the above aromatic hydrocarbon group and the aromatic heterocyclic group are the same groups as those exemplified above concerning the $Ar^1$, and the substituents which may be possessed by these groups are the same as those exemplified concerning $Ar^1$.

($R^8$, $r^8$ and $R^{16}$, $r^{16}$)

In the general formula (1), $r^8$ represents number of $R^8$ which can be bonded to the anthracene ring, and is an integer of 0 to 8. Similarly, $r^{16}$ in the general formula (2) represents the number of $R^8$ which can be bonded to the anthracene ring of $R^{16}$, and is an integer of 0 to 7.

Further, $R^8$ and $R^{16}$ are deuterium atoms, fluorine atoms, chlorine atoms, cyano groups, trifluoromethyl groups or unsubstituted alkyl groups having 1 to 6 carbon atoms. When $r^8$ and $r^{16}$ are numbers of 2 or more, the plurality of $R^8$ and $R^{16}$, respectively, may be the same or different.

The above unsubstituted alkyl groups, too, are the same alkyl groups as those exemplified above as the substituents which the above divalent groups A and B may have.

(W to Z)

In either case of the formula (1) or the formula (2), only any one of the atoms W, X, Y and Z forming part of the pyridoindole ring is a nitrogen atom, and the others are carbon atoms. Generally, though not limited thereto only, Y is a nitrogen atom, and W, X and Z are carbon atoms.

Further, any of the groups $R^1$ to $R^4$ (inclusive of hydrogen atom) is bonded to the carbon atom that constitutes the ring. To the nitrogen atom, however, neither the groups $R^1$ to $R^4$ nor the hydrogen atom is bonded.

Preferred Electron-Transporting Compounds of the General Formula (1):

In the electron-transporting compound represented by the above general formula (1), it is desired that the position where the anthracene ring bonds to the pyridoindole ring has been fixed to the position shown, for example, by the following formula (1a).

[Chemical 9]

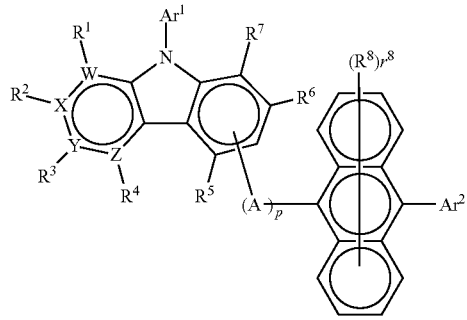

(1a)

In the above general formula (1a), A, Ar$^1$, Ar$^2$, R$^1$ to R$^8$, p, r$^8$, W, X, Y and Z are as described in the above general formula (1).

Among the atoms W to Z constituting the ring as described above, further, it is desired that Y is a nitrogen atom and, further, that the anthracene ring and the pyridoindole ring are bonded together through a single bond (i.e., p=0) or are bonded together through a divalent benzene ring group (phenylene group) or a naphthalene ring group (p=1) and, further, that r$^8$=0. Preferred electron-transporting compounds having such structures are represented, for example, by the following general formulas (1b) to (1g).

[Chemical 10]

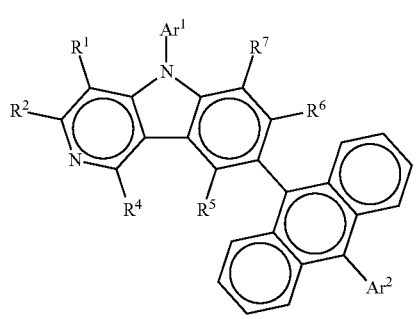

(1b)

[Chemical 11]

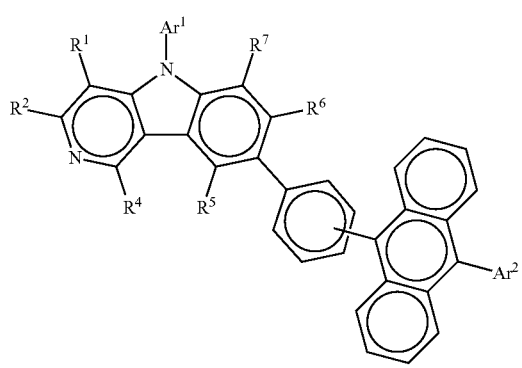

(1c)

[Chemical 12]

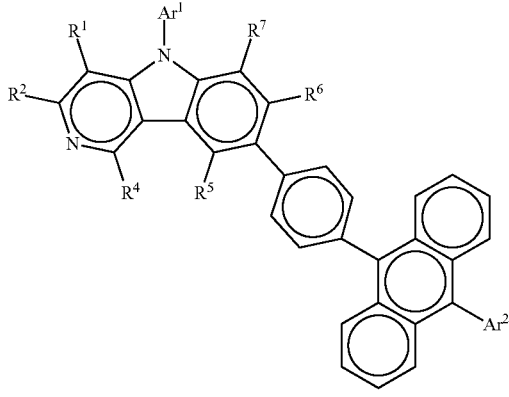

(1d)

[Chemical 13]

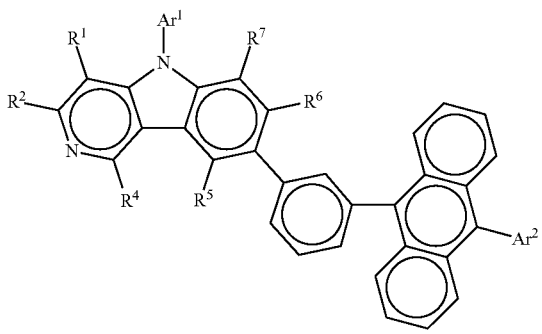

(1e)

[Chemical 14]

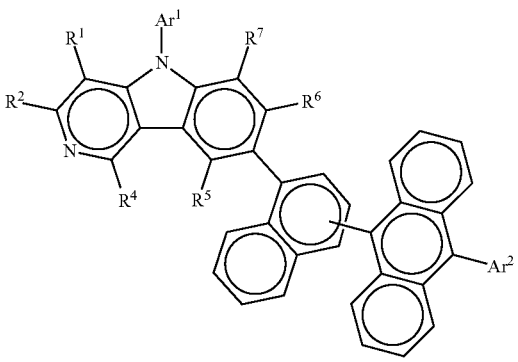

(1f)

[Chemical 15]

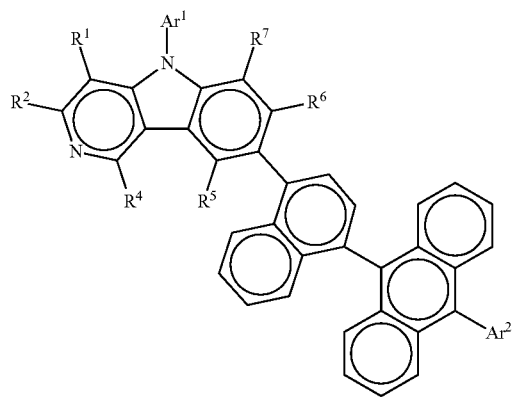

(1g)

In the above general formulas (1b) to (1g), $Ar^1$, $Ar^2$, $R^1$, $R^2$ and $R^4$ to $R^7$ are as described in the above general formula (1).

Concrete Examples of the Electron-Transporting Compound of the General Formula (1).

As concrete examples of the electron-transporting compound represented by the above general formula (1), the following compounds can be exemplified though not limited thereto only.

[Chemical 16]

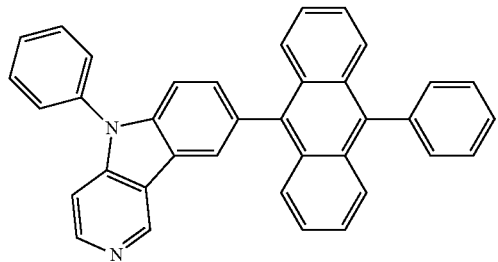

(1-1)

[Chemical 17]

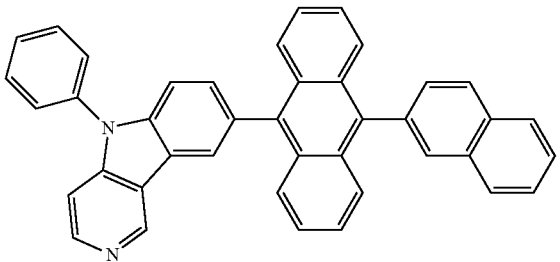

(1-2)

[Chemical 18]

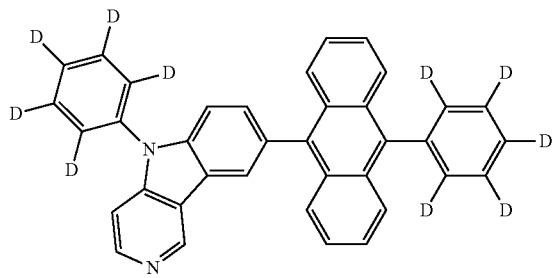

(1-3)

[Chemical 19]

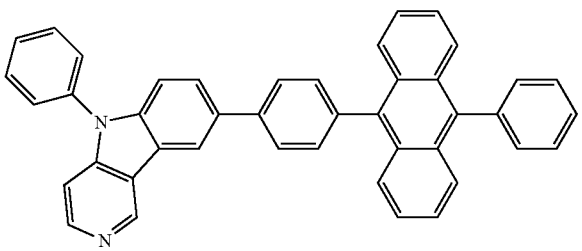

(1-4)

-continued
[Chemical 20]
(1-5)
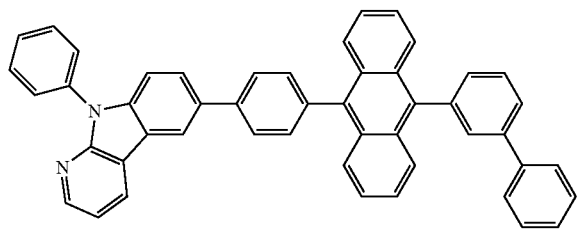
[Chemical 21]
(1-6)
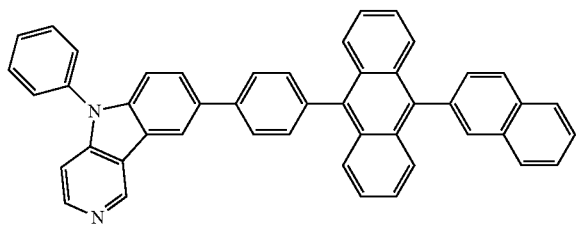
[Chemical 22]
(1-7)
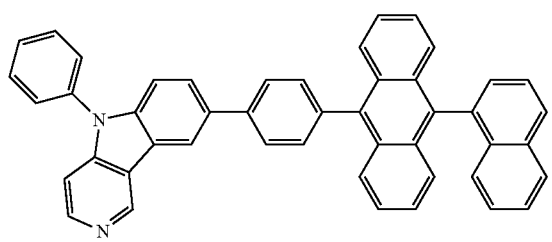
[Chemical 23]
(1-8)
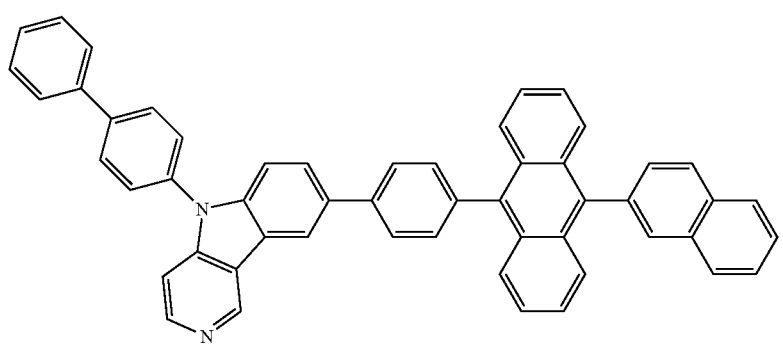
[Chemical 24]
(1-9)
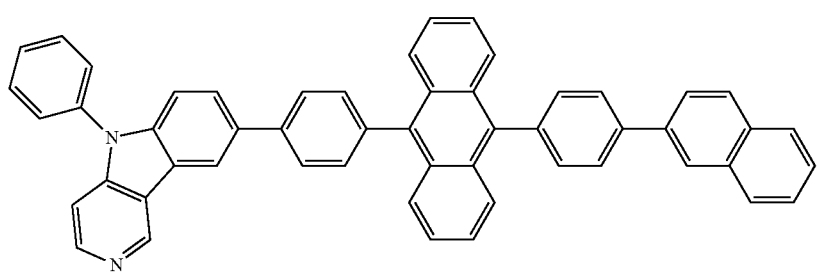

-continued
[Chemical 25]
(1-10)
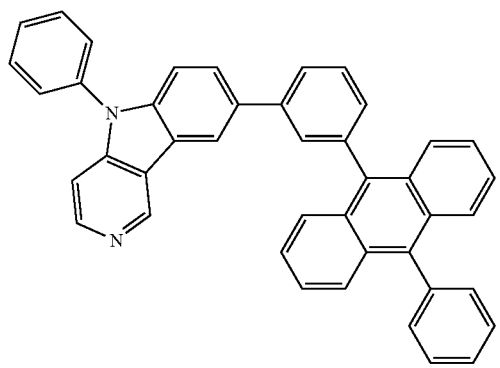
[Chemical 26]
(1-11)
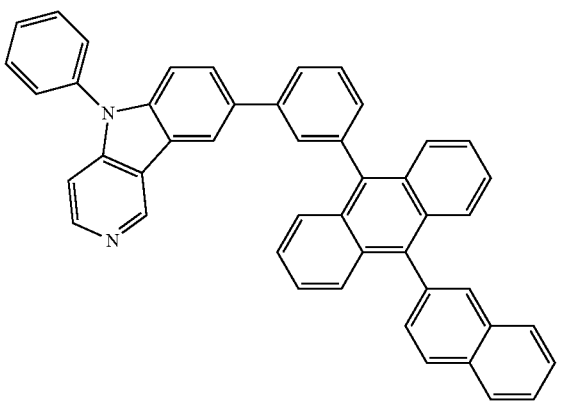
[Chemical 27]
(1-12)
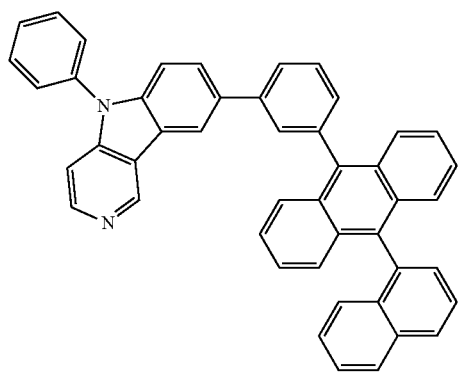
[Chemical 28]
(1-13)
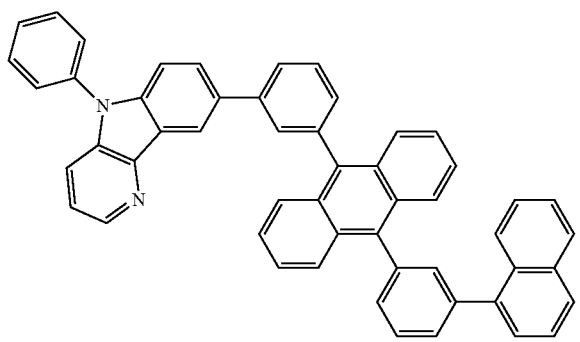
[Chemical 29]
(1-14)
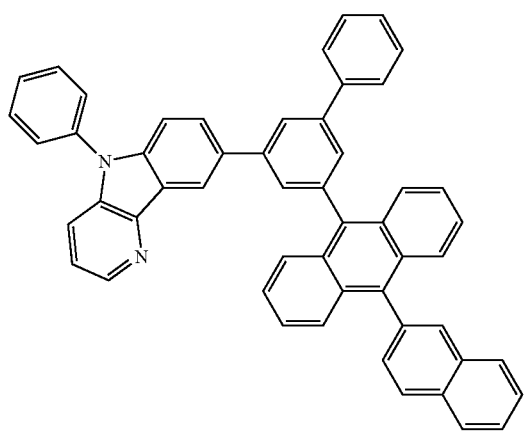
[Chemical 30]
(1-15)
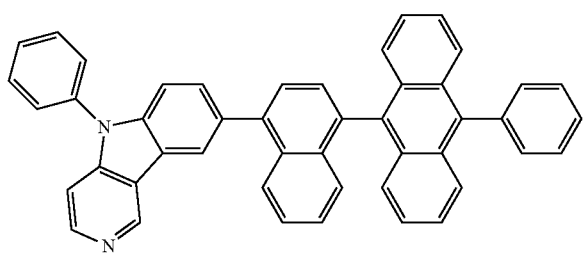

[Chemical 31]
(1-16)
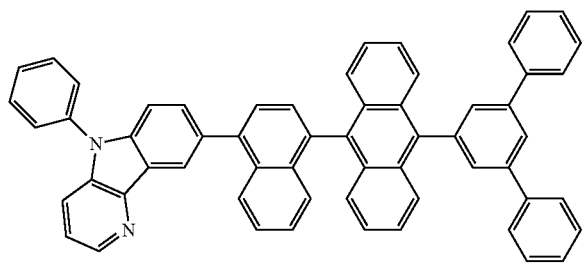
[Chemical 32]
(1-17)
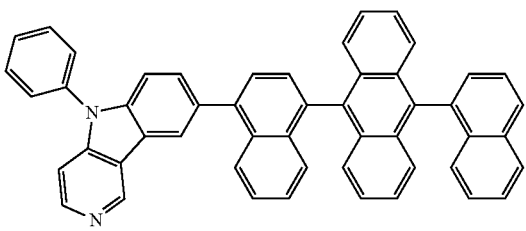
[Chemical 33]
(1-18)
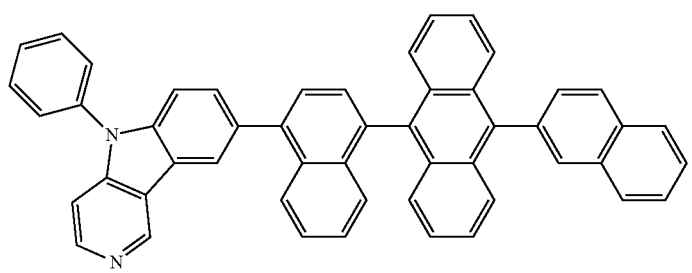
[Chemical 34]
(1-19)
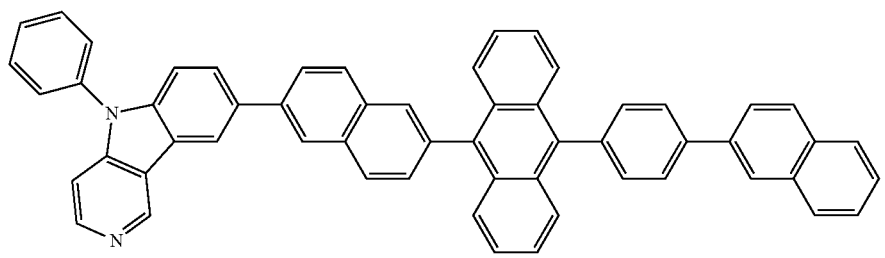
[Chemical 35]
(1-20)
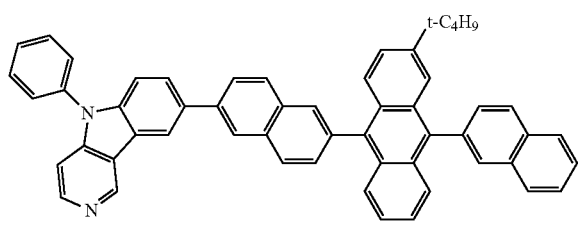
[Chemical 36]
(1-21)
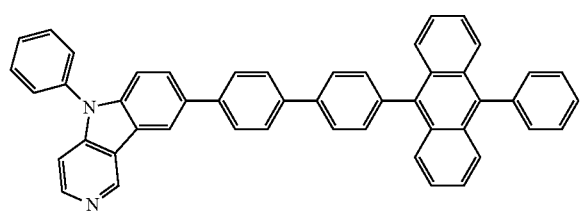
[Chemical 37]
(1-22)
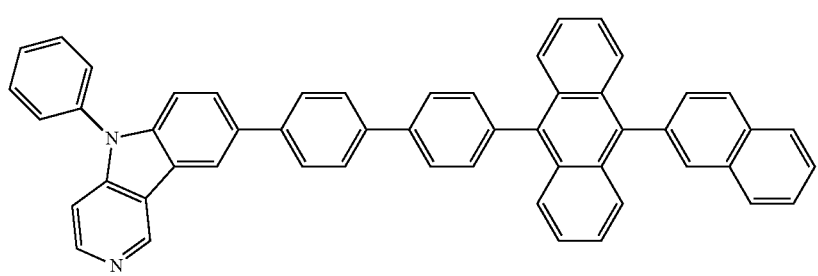

-continued
[Chemical 38]
(1-23)
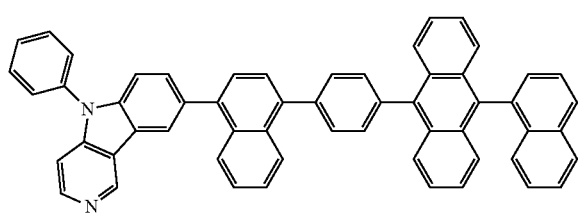
[Chemical 39]
(1-24)
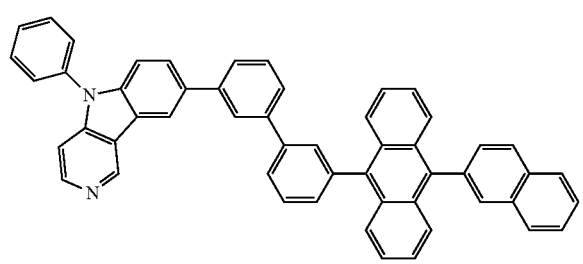
[Chemical 40]
(1-25)
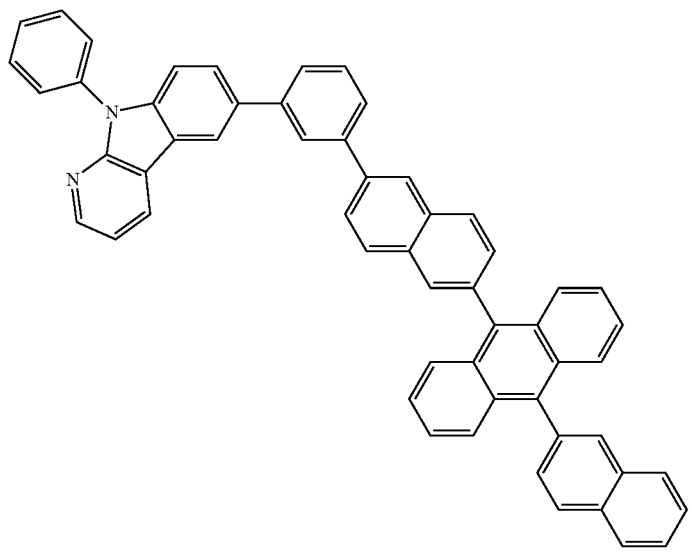
[Chemical 41]
(1-26)
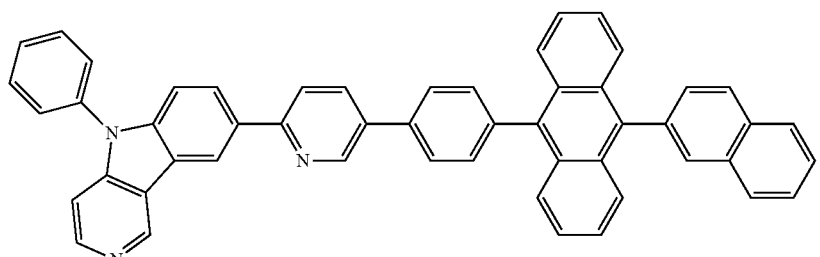
[Chemical 42]
(1-27)
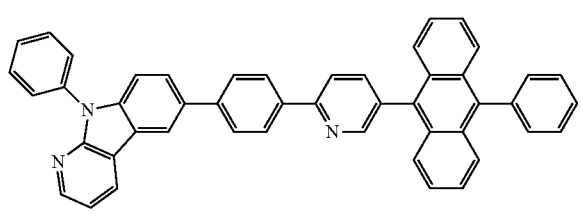
[Chemical 43]
(1-28)
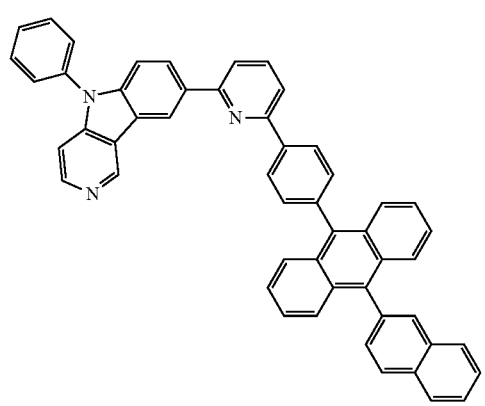

[Chemical 44]
(1-29)
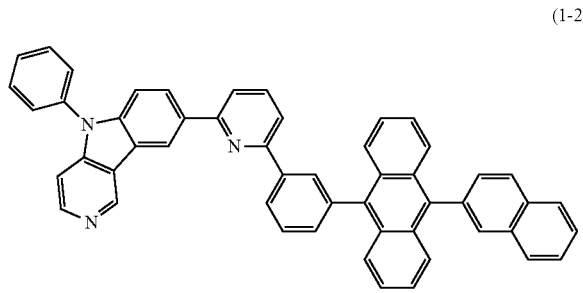
[Chemical 45]
(1-30)
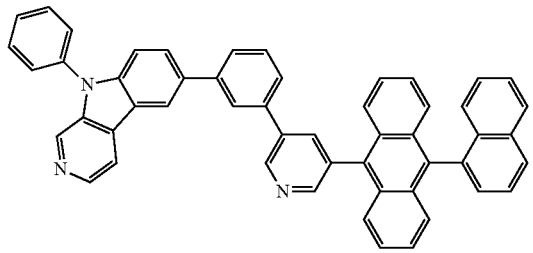
[Chemical 46]
(1-31)
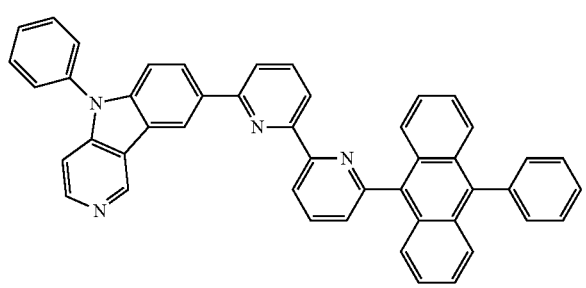
[Chemical 47]
(1-32)
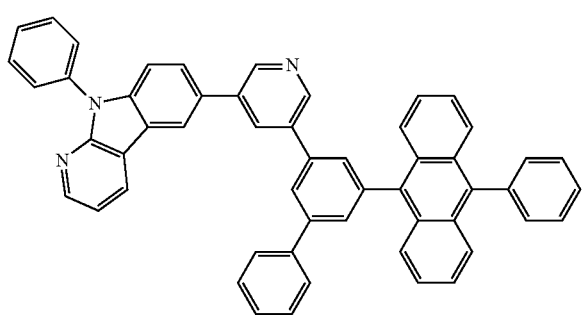
[Chemical 48]
(1-33)
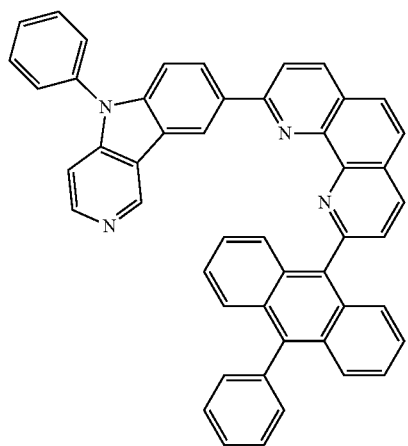
[Chemical 49]
(1-34)
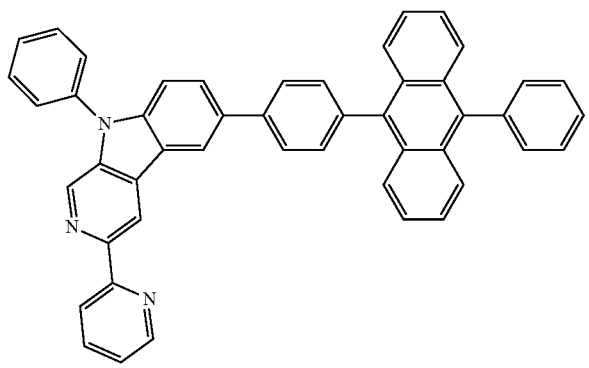
[Chemical 50]
(1-35)
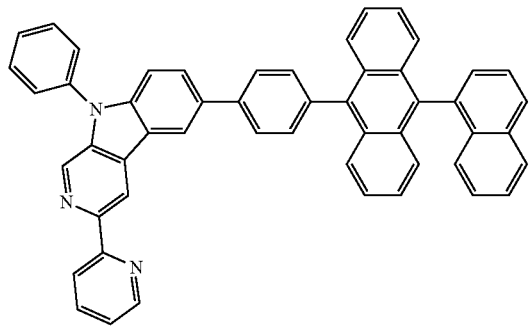
[Chemical 51]
(1-36)
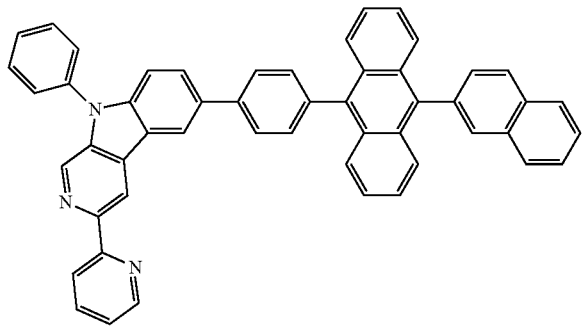

[Chemical 52]

(1-37)

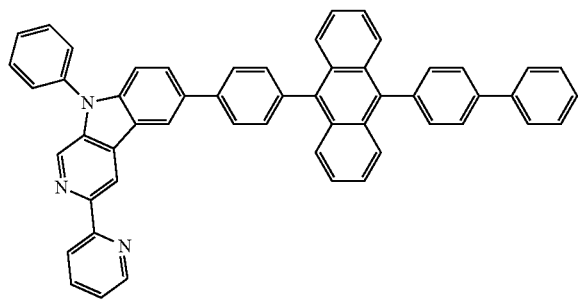

[Chemical 53]

(1-38)

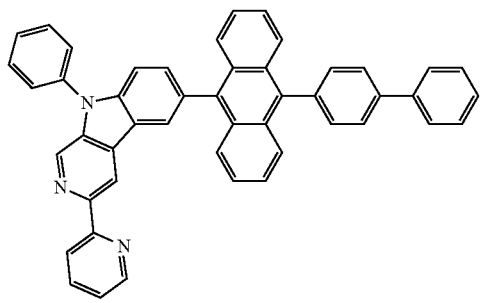

[Chemical 54]

(1-39)

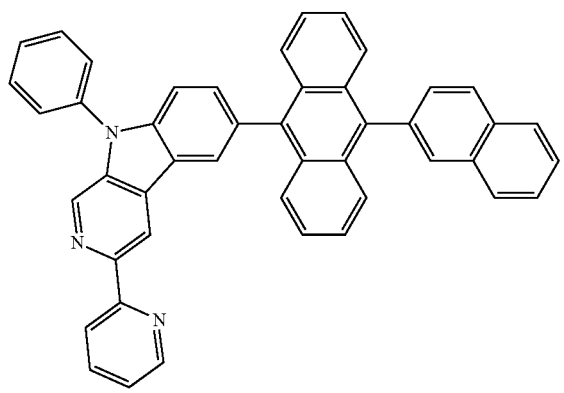

[Chemical 55]

(1-40)

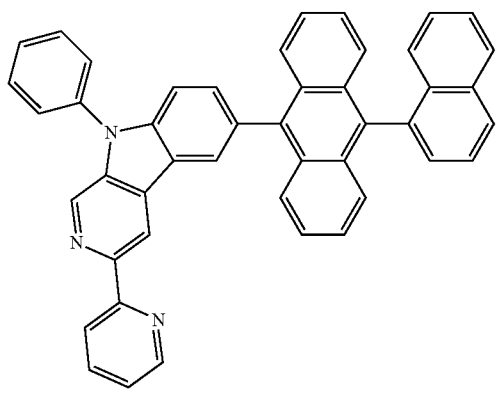

Preferred Electron-Transporting Compounds of the General Formula (2):

In the electron-transporting compound of the invention represented by the above general formula (2), it is desired that the pyridoindole ring is bonded to the second position of the anthracene ring as represented by, for example, the following formula (2a) and it is, further, desired that the position where the anthracene ring bonds to the pyridoindole ring is fixed to the position shown in the following formula (2b).

[Chemical 56]

(2a)

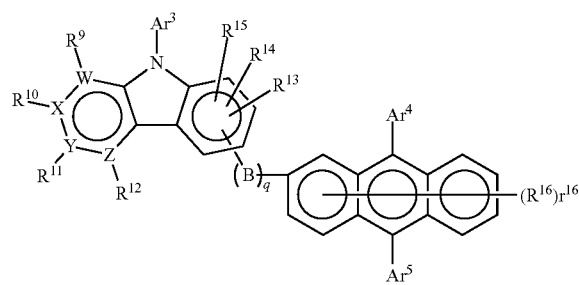

[Chemical 57]

(2b)

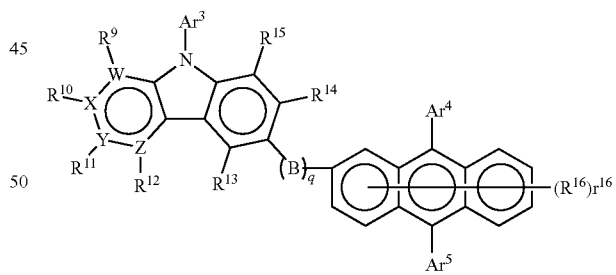

In the above formulas, B, $Ar^3$ to $Ar^5$, $R^9$ to $R^{16}$, q, $r^{16}$, W, X, Y and Z are as described in the above general formula (2).

Among the atoms W to Z constituting the ring in the above electron-transporting compounds, too, it is desired that Y is a nitrogen atom and, further, that the anthracene ring and the pyridoindole ring are bonded together through a single bond (i.e., q=0) or are bonded together through a phenylene group (q=1) and, further, that $r^{16}$=0.

Preferred electron-transporting compounds having such structures are represented, for example, by the following general formulas (2c) to (2e).

[Chemical 58]

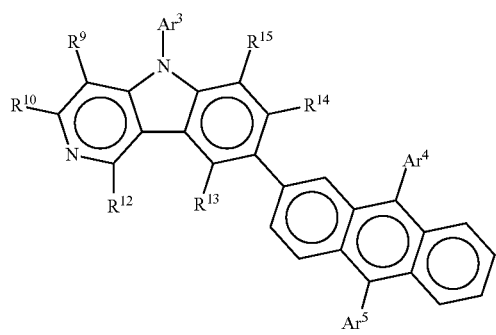

(2c)

[Chemical 59]

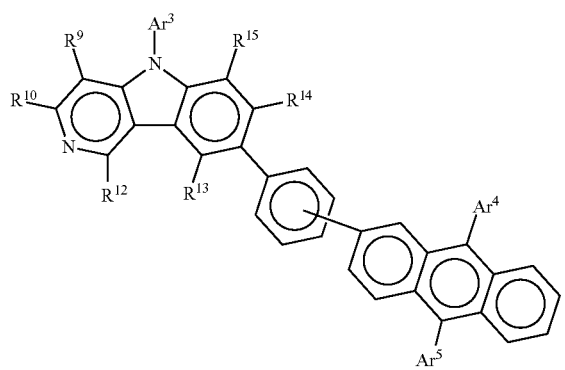

(2d)

[Chemical 60]

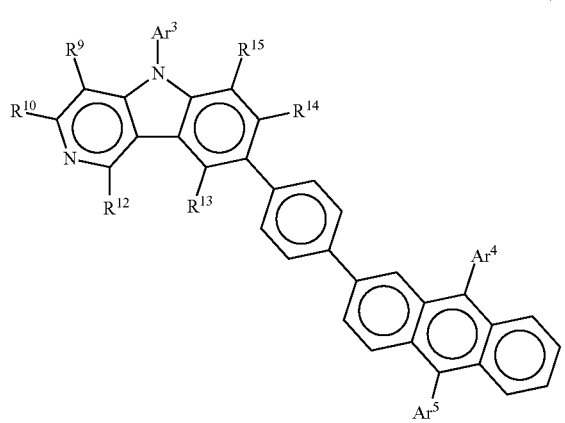

(2e)

In the above formulas, $Ar^3$ to $Ar^5$, $R^9$, $R^{10}$ and $R^{12}$ to $R^{15}$ are as described in the above general formula (2).

Concrete Examples of the Electron-Transporting Compound of the General Formula (2).

As concrete examples of the electron-transporting compound represented by the above general formula (2), the following compounds can be exemplified though not limited thereto only.

[Chemical 61]

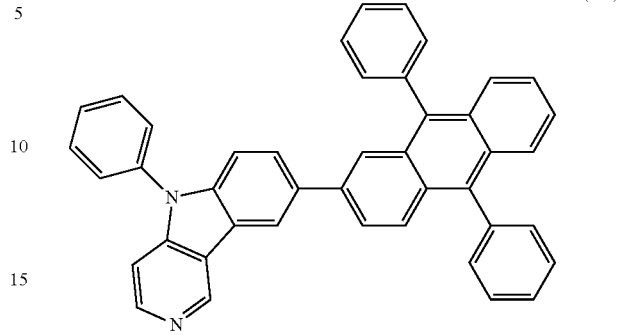

(2-1)

[Chemical 62]

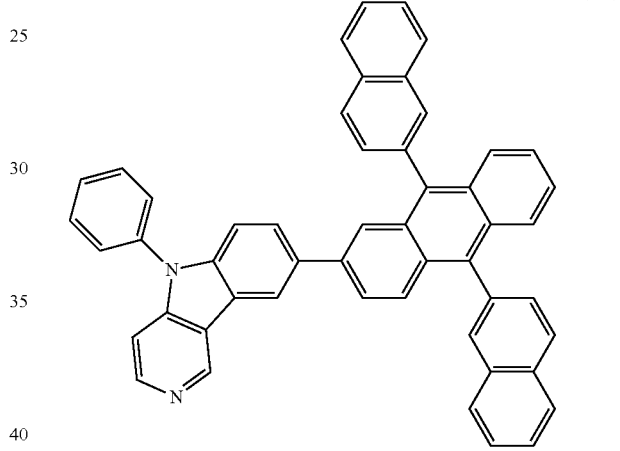

(2-2)

[Chemical 63]

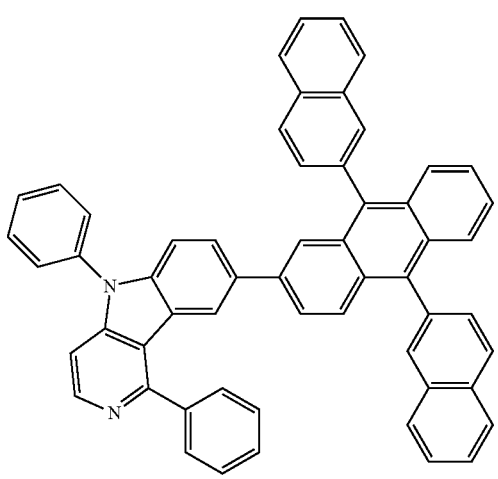

(2-3)

[Chemical 64]

(2-4)

[Chemical 65]

(2-5)

[Chemical 66]

(2-6)

[Chemical 67]

(2-7)

[Chemical 68]

(2-8)

[Chemical 69]

(2-9)

[Chemical 70]
(2-10)
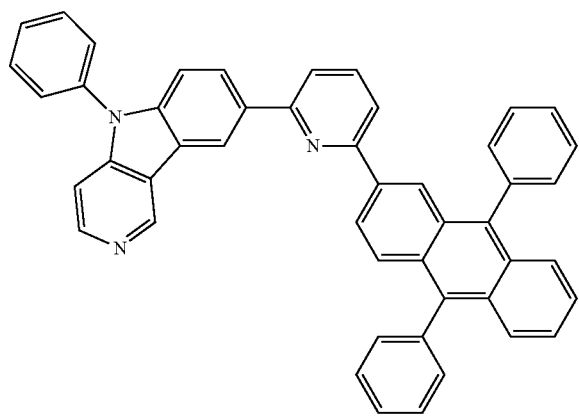
[Chemical 71]
(2-11)
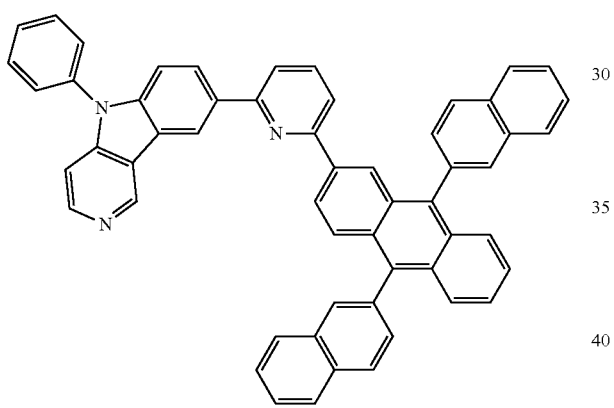
[Chemical 72]
(2-12)
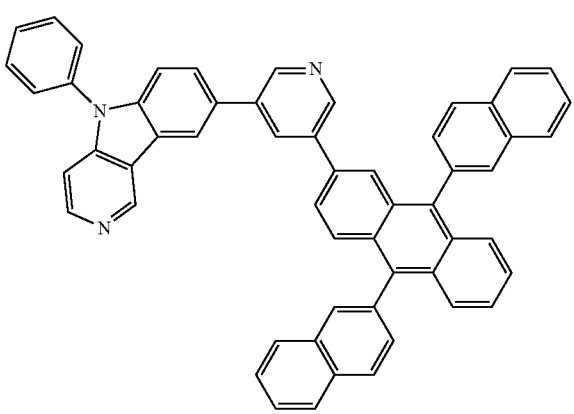
[Chemical 73]
(2-13)
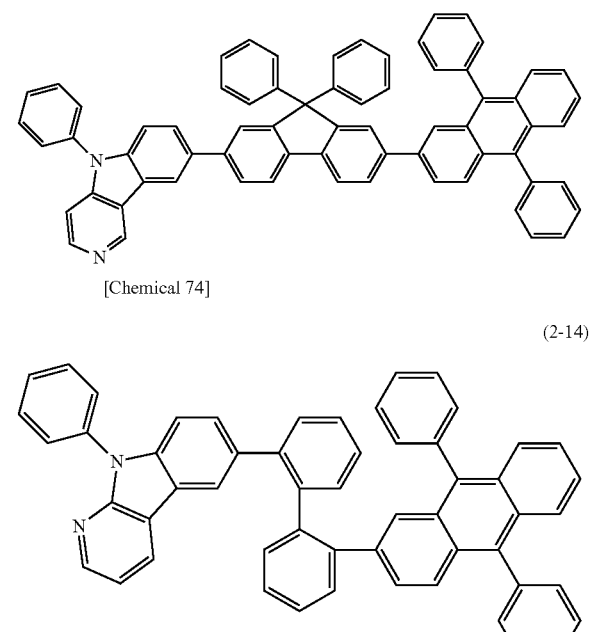
[Chemical 74]
(2-14)
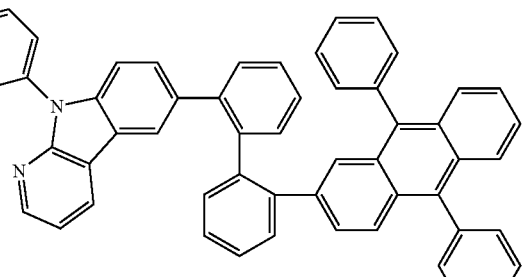
[Chemical 75]
(2-15)
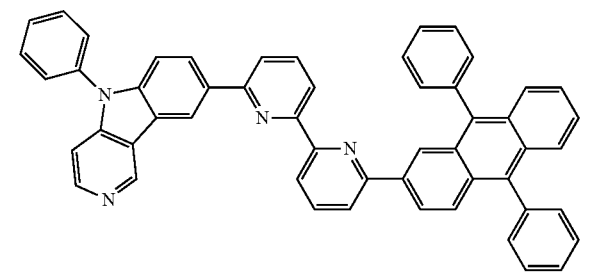
[Chemical 76]
(2-16)
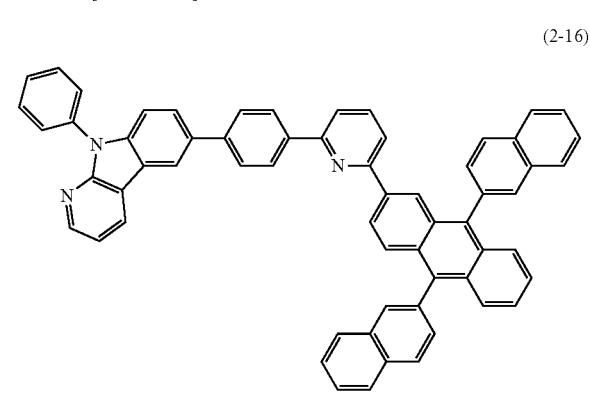

[Chemical 77]
(2-17)
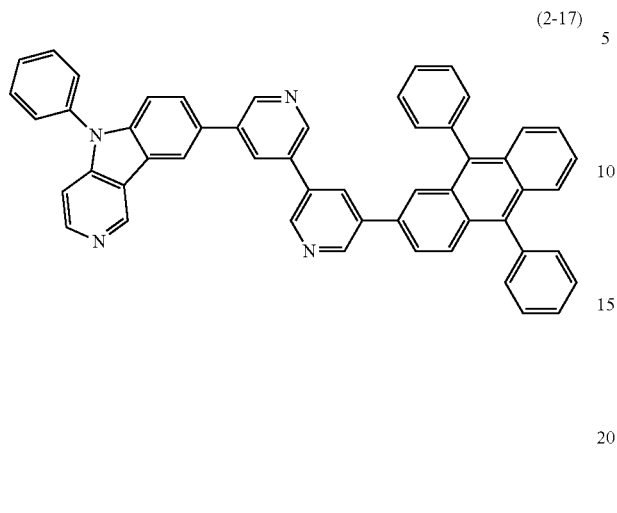
[Chemical 78]
(2-18)
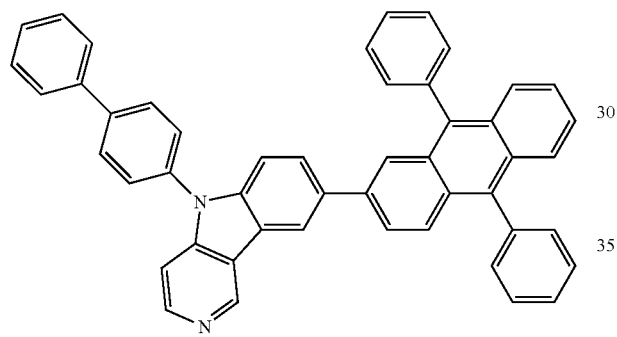
[Chemical 79]
(2-19)
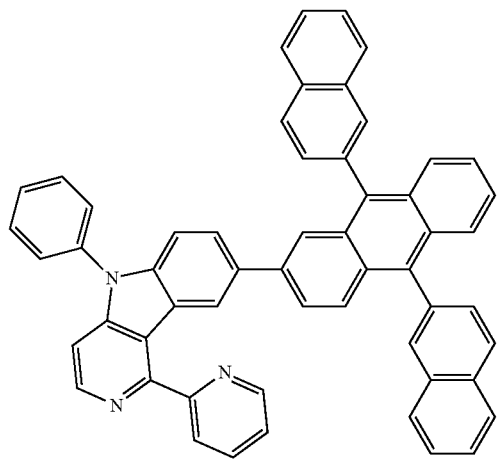
[Chemical 80]
(2-20)
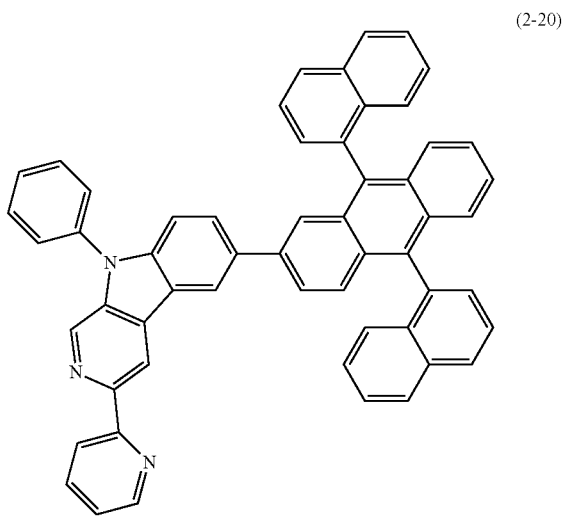
[Chemical 81]
(2-21)
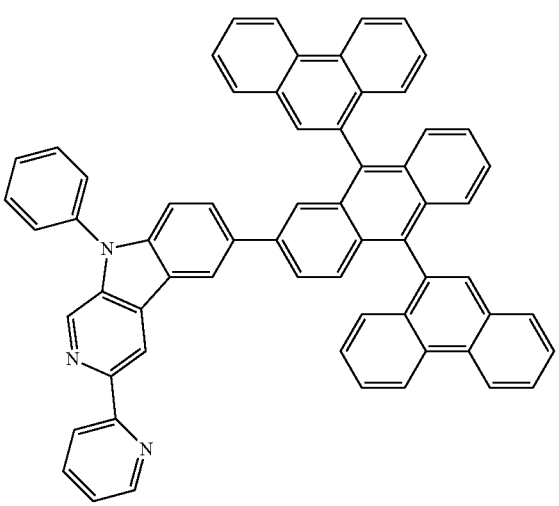

35

-continued

[Chemical 82]

(2-22)

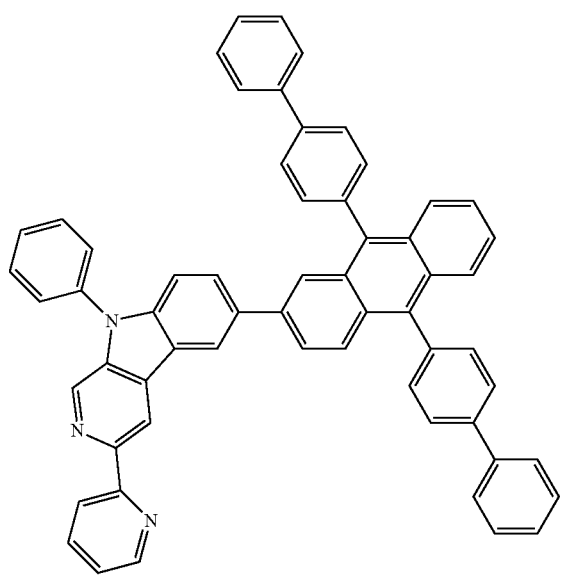

(Preparation of the Electron-Transporting Compounds)

The electron-transporting compound represented by the above general formula (1) or (2) is a novel compound which can be synthesized in a manner, for example, as described below.

First, a corresponding halogenoanilinopyridine is subjected to the cyclization reaction by using a palladium catalyst to synthesize a corresponding pyridoindole derivative (e.g., see J. Chem. Soc., Perkin Trans. 1, 1505 (1999)) which is, further, subjected to the condensation reaction such as Ullmann reaction or Buchwald-Hartwig reaction with halides of various aromatic hydrocarbon compounds or aromatic heterocyclic compounds to synthesize a pyridoindole derivative having aryl groups ($Ar^1$, $Ar^3$) introduced into the corresponding fifth position thereof.

36

The thus synthesized pyridoindole derivative is brominated by using an N-bromosuccinimide to synthesize a corresponding brominated body.

The brominated body of the pyridoindole derivative and the boronic acid or the boronic acid ester having an anthracene ring structure synthesized by a known method (see, for example, J. Org. Chem., 60, 7508 (1995)) are subjected to the cross-coupling reaction such as Suzuki's coupling (e.g., see non-patent document 5) to synthesize the above electron-transporting compound having the anthracene ring skeleton and the pyridoindole ring skeleton.

Further, a corresponding boronic acid or a boronic acid ester is synthesized from the brominated body of the above pyridoindole derivative followed by the reaction with a dihalogenated product of the aromatic hydrocarbon or the aromatic heterocyclic ring to prepare a pyridoindole derivative to which a halogenated aryl group is bonded. Thereafter, the above boronic acid or the boronic acid ester having the anthracene ring structure are subjected to the cross-coupling reaction such as Suzuki's coupling to synthesize the above-mentioned electron-transporting compound having the anthracene ring skeleton and the pyridoindole ring skeleton.

<Arylamine Compounds (α)>

In the invention, the hole injection layer is formed by using the arylamine compound (α) having a molecular structure in which three or more triphenylamine skeletons are bonded together through a single bond or a divalent hydrocarbon group (i.e., divalent group without having hetero atom). The arylamine compound (α) has a higher hole mobility than that of the arylamine compound (β) that will be described later.

The arylamine compound (α) is a trimer or a tetramer of various triphenylamines and, preferably, has four triphenylamine skeletons, specifically, from the standpoint of high hole mobility. As the arylamine having four triphenylamine skeletons, there can be exemplified those represented by the following general formula (3).

[Chemical 83]

(3)

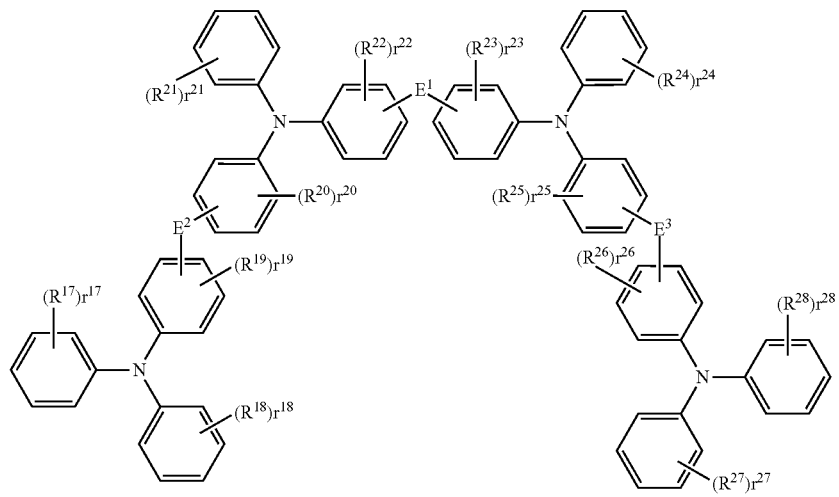

($R^{17}$ to $R^{28}$ and $r^{17}$ to $r^{28}$)

In the above general formula (3), $r^{17}$ to $r^{28}$ represent the numbers of the groups $R^{17}$ to $R^{28}$ that can bond to the benzene rings in the molecules and among them, $r^{17}$, $r^{18}$, $r^{21}$, $r^{24}$, $r^{27}$ and $r^{28}$ are integers of 0 to 5. Further, $r^{19}$, $r^{20}$, $r^{22}$, $r^{23}$, $r^{25}$ and $r^{26}$ are integers of 0 to 4. Namely, $r^{17}$ to $r^{28}$ that have a value of 0 mean that none of the groups $R^{17}$ to $R^{28}$ is bonded to the benzene rings.

$R^{17}$ to $R^{28}$ are, respectively, deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, or unsubstituted or substituted aromatic hydrocarbon groups or aromatic heterocyclic groups. Among these groups, those bonded to the same benzene ring (when $r^{17}$ to $r^{28}$ are 2 or more) may be bonded together to form a ring.

In the above $R^{17}$ to $R^{28}$, the unsubstituted alkyl group having 1 to 6 carbon atoms may be a straight chain or branched, and can be methyl group, ethyl group, n-propyl group, isopropyl group, n-butyl group, isobutyl group, tert-butyl group, n-pentyl group, isopentyl group, neopentyl group or n-hexyl group.

The unsubstituted alkenyl group having 2 to 6 carbon atoms, too, may be a straight chain or branched, and can be vinyl group, allyl group, isopropenyl group or 2-butenyl group.

As the aromatic hydrocarbon group, there can be exemplified phenyl group, biphenylyl group, terphenylyl group, tetrakisphenyl group, stylyl group, naphthyl group, anthryl group, acenaphthenyl group, fluorenyl group and phenanthryl group.

As the aromatic heterocyclic group, there can be exemplified indenyl group, pyrenyl group, pyridyl group, pyrimidyl group, furanyl group, pyrrolyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group, naphthyridinyl group, phenanthrolynyl group and acridinyl group.

Any of the alkenyl group, aromatic hydrocarbon group or the aromatic heterocyclic group may have a substituent. As the substituent, there can be exemplified deuterium atom, fluorine atom, chlorine atom, trifluoromethyl group, alkyl group having 1 to 6 carbon atoms, phenyl group, biphenylyl group, terphenylyl, tetrakisphenyl group, stylyl group, naphthyl group, fluorenyl group, phenanthryl group, indenyl group and pyrenyl group, and these substituents may have another substituent.

Further, when some of those are present in plural numbers among $R^{17}$ to $R^{28}$ and are bonded together to form rings, they may be bonded together via a single bond to form rings,

[Chemical 85]

or may be bonded together via a methylene group that may have a substituent or via an oxygen atom or a sulfur atom to form rings. Specifically, it is desired that the groups are bonded to each other via a dimethylmethylene group to form rings.

In the invention, it is desired that at least any one of $R^{17}$ to $R^{28}$ is a deuterium atom or a group containing deuterium atom, such as alkenyl group having a deuterium atom as a substituent, an aromatic hydrocarbon group or an aromatic heterocyclic group.

($E^1$ to $E^3$)

In the general formula (3), $E^1$ to $E^3$ correspond to the portions where triphenylamine skeletons are bonded together, and are single bonds or divalent hydrocarbon groups.

The divalent hydrocarbon groups, i.e., the divalent groups without having hetero atom are represented by the following formulas.

[Chemical 84]

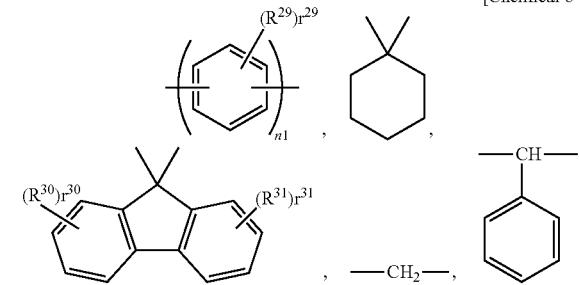

In the above formulas representing the divalent groups, n1 is an integer of 1 to 3, and $r^{29}$, $r^{30}$ and $r^{31}$ representing the numbers of $R^{29}$, $R^{30}$ and $R^{31}$ are, respectively, integers of 0 to 4.

Further, $R^{29}$, $R^{30}$ and $R^{31}$ are, respectively, the same atoms or groups as those represented by $R^{17}$ to $R^{28}$ above.

Concrete Examples of the Arylamine Compound (α) of the General Formula (3).

As the arylamine compound (α) represented by the above general formula (3), there can be concretely exemplified the following compounds (3-1) to (3-23) though not limited thereto only. Among them, the triarylamine (having four triphenylamine skeletons) represented by the above general formula (3) is specifically desired.

(3-1)

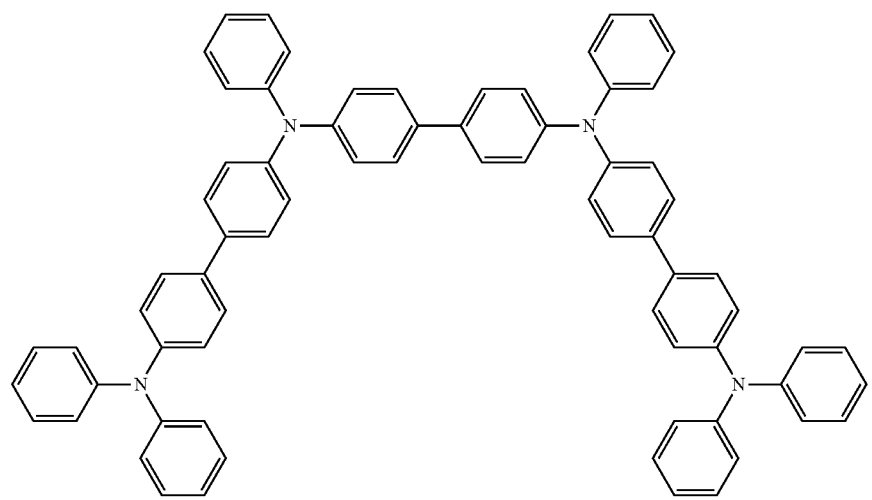

[Chemical 86]
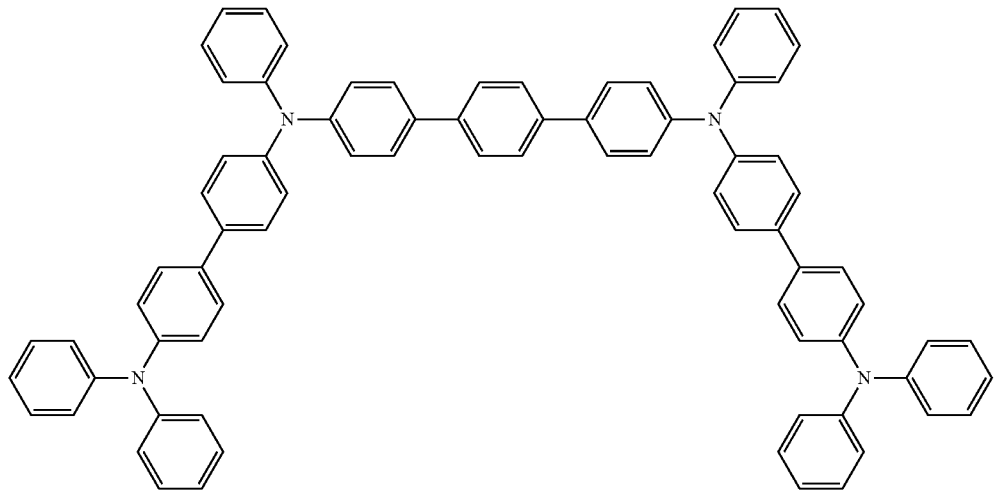
(3-2)
[Chemical 87]
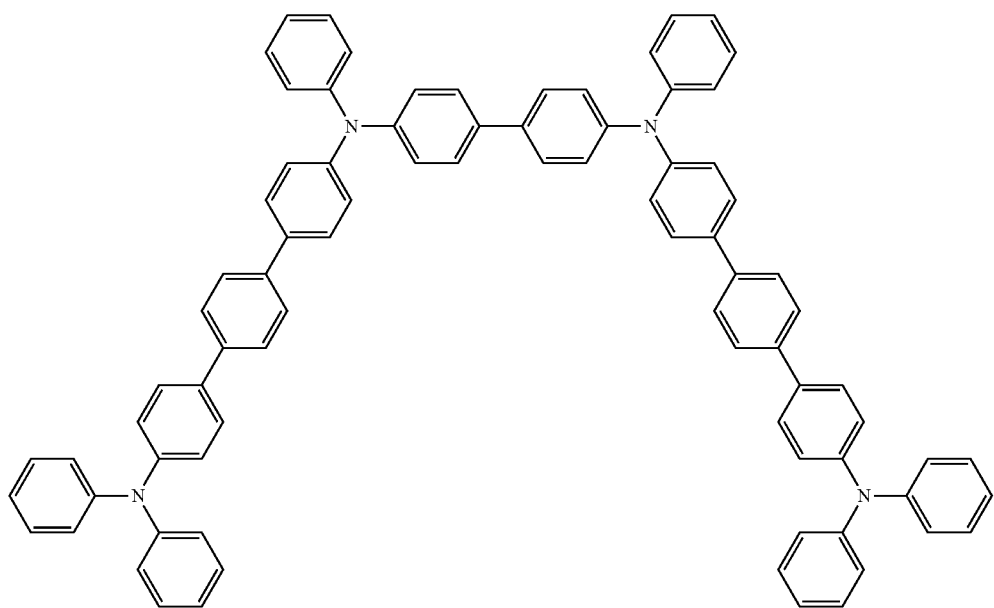
(3-3)

[Chemical 88]
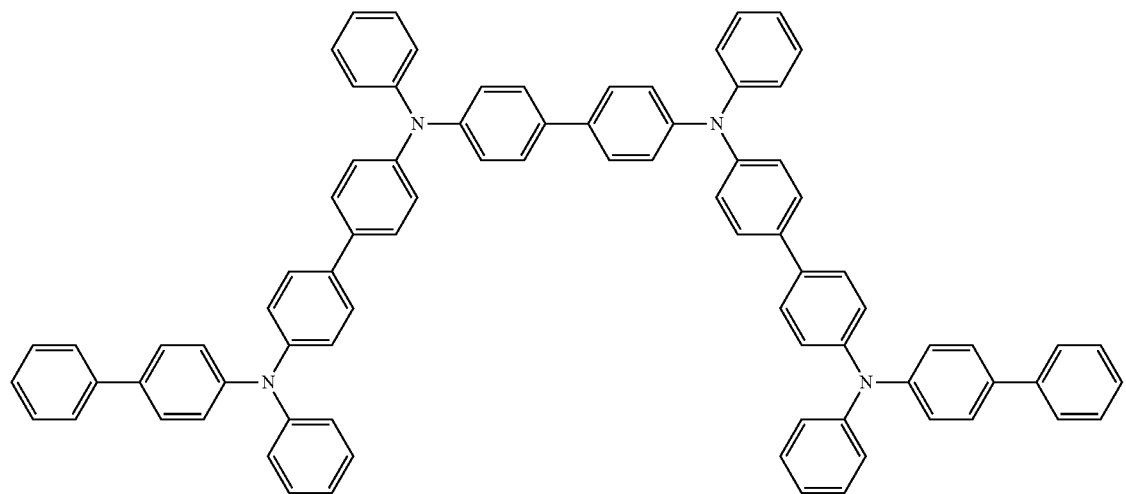
(3-4)
[Chemical 89]
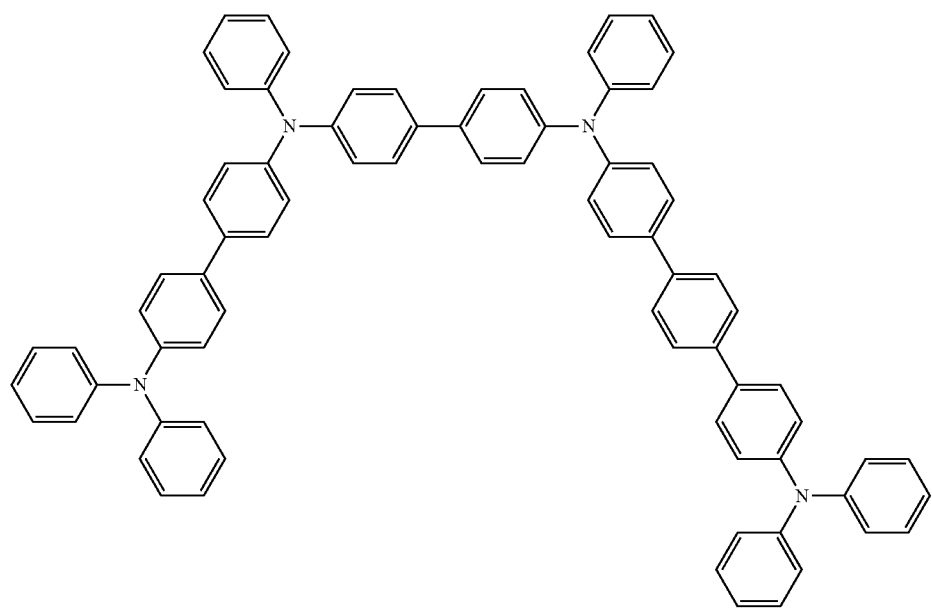
(3-5)
[Chemical 90]
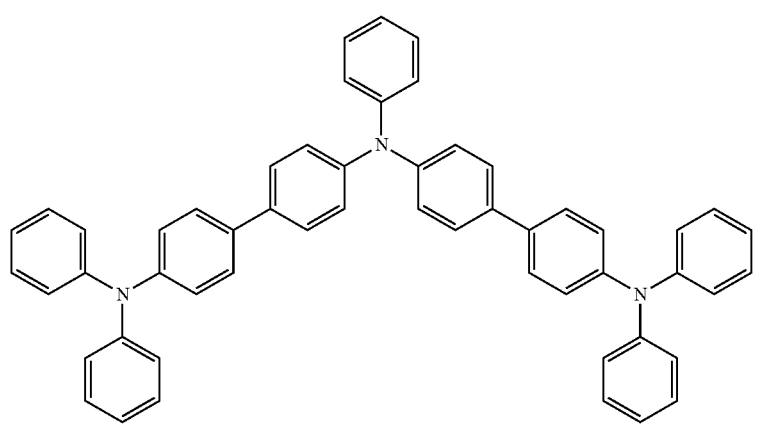
(3-6)

[Chemical 91]
(3-7)
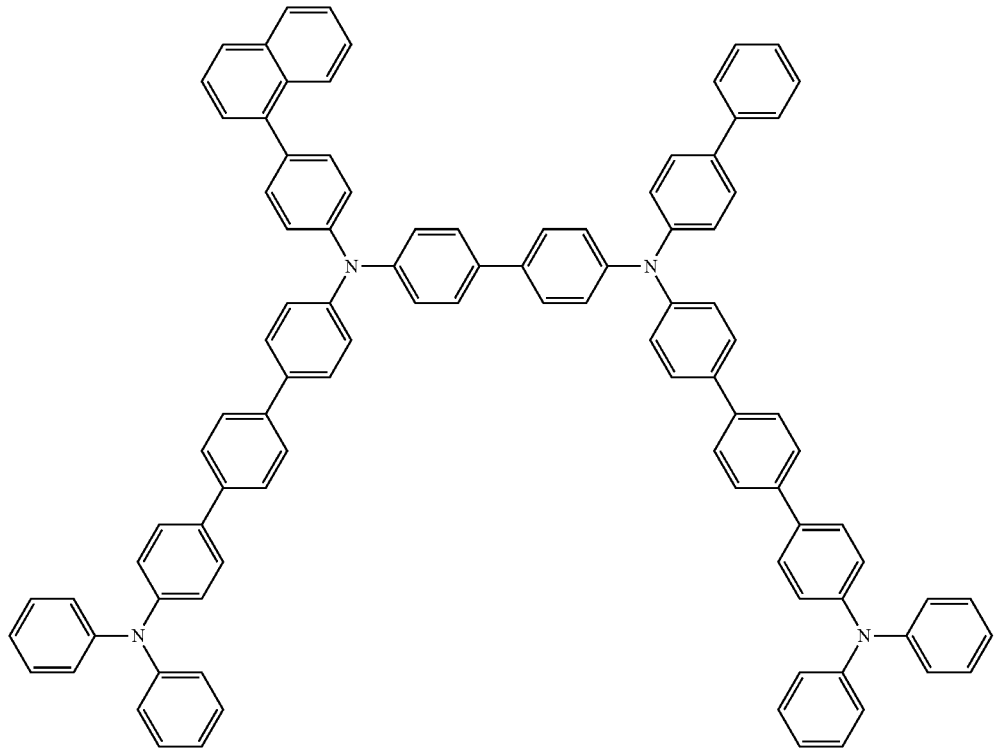
[Chemical 92]
(3-8)
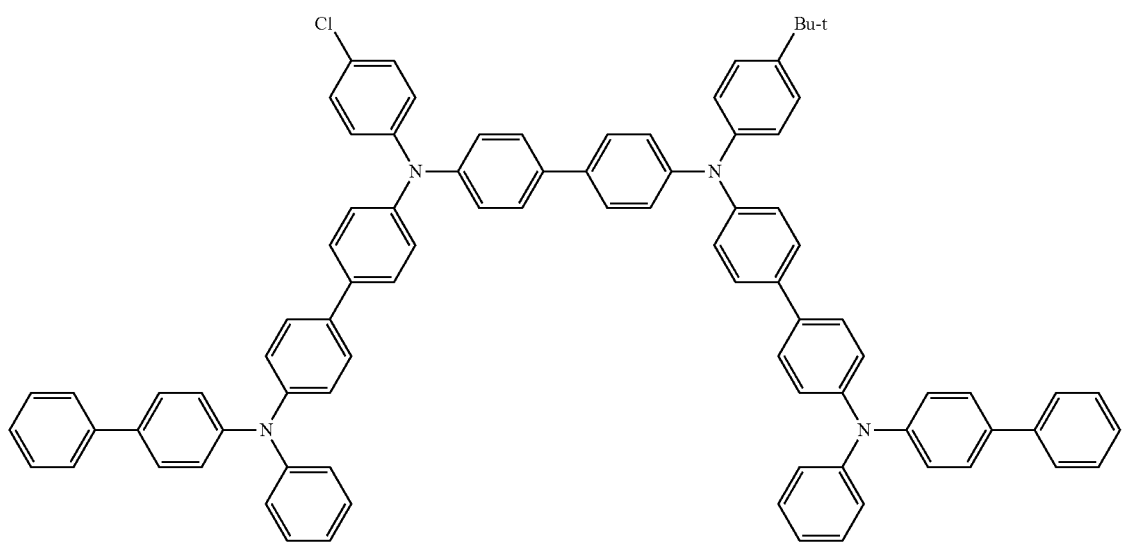

[Chemical 93]
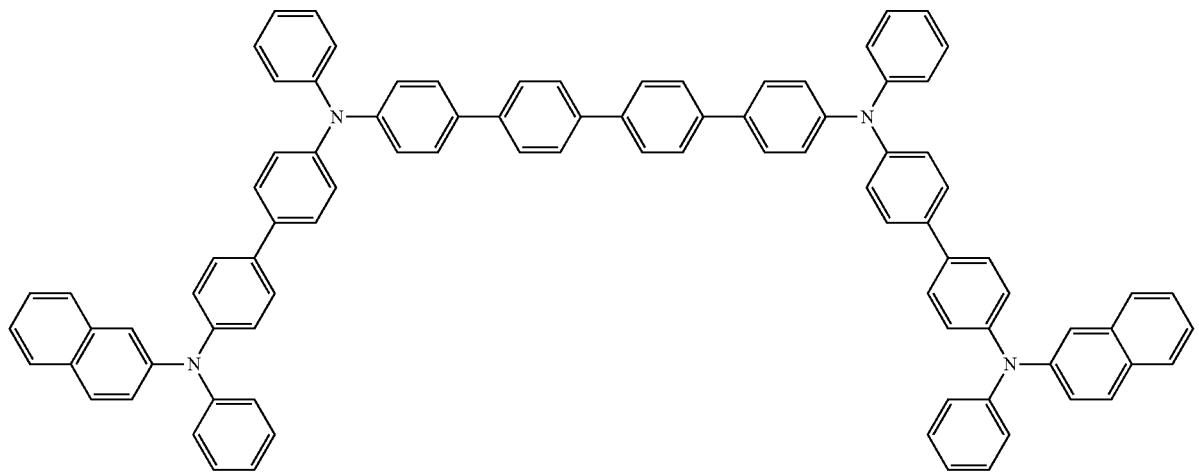
(3-9)
[Chemical 94]
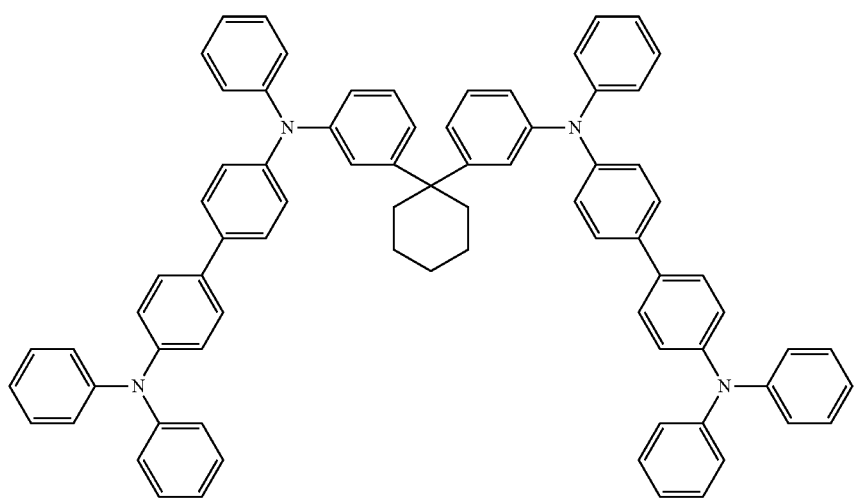
(3-10)
[Chemical 95]
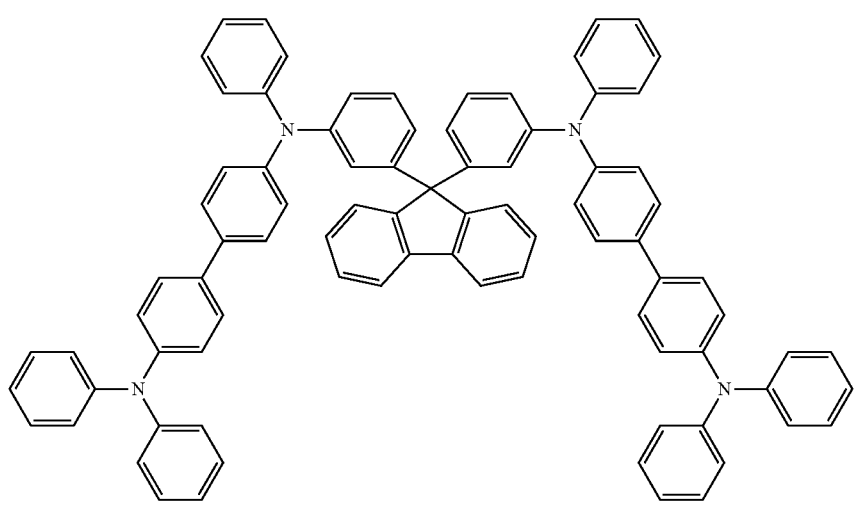
(3-11)

[Chemical 96]
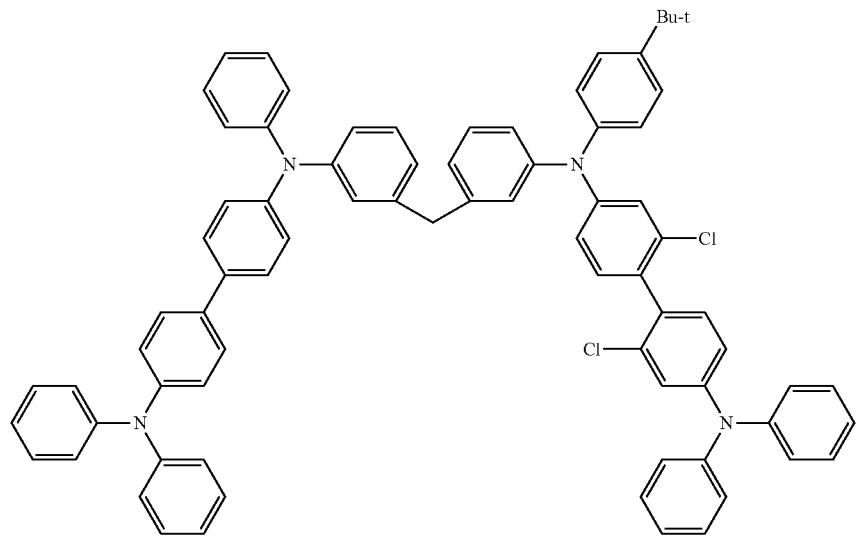
(3-12)
[Chemical 97]
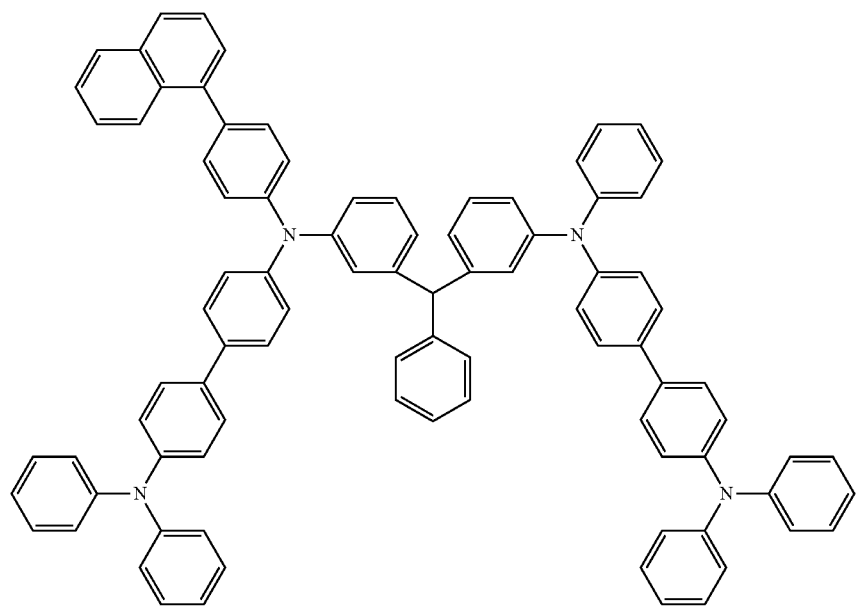
(3-13)

[Chemical 98]
(3-14)
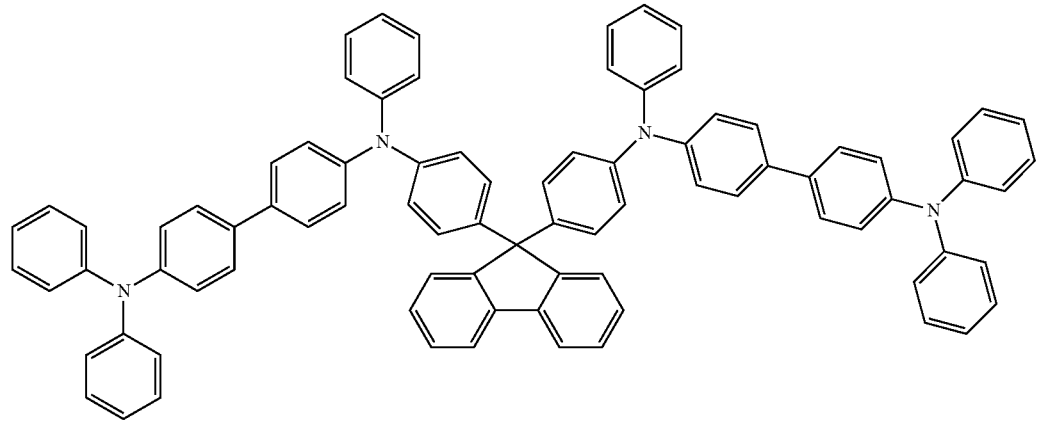
[Chemical 99]
(3-15)
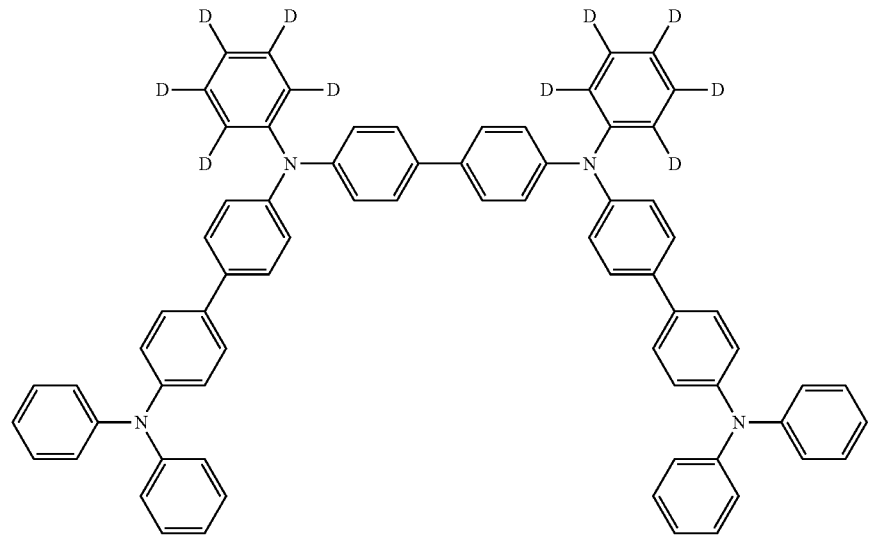

[Chemical 100]
(3-16)
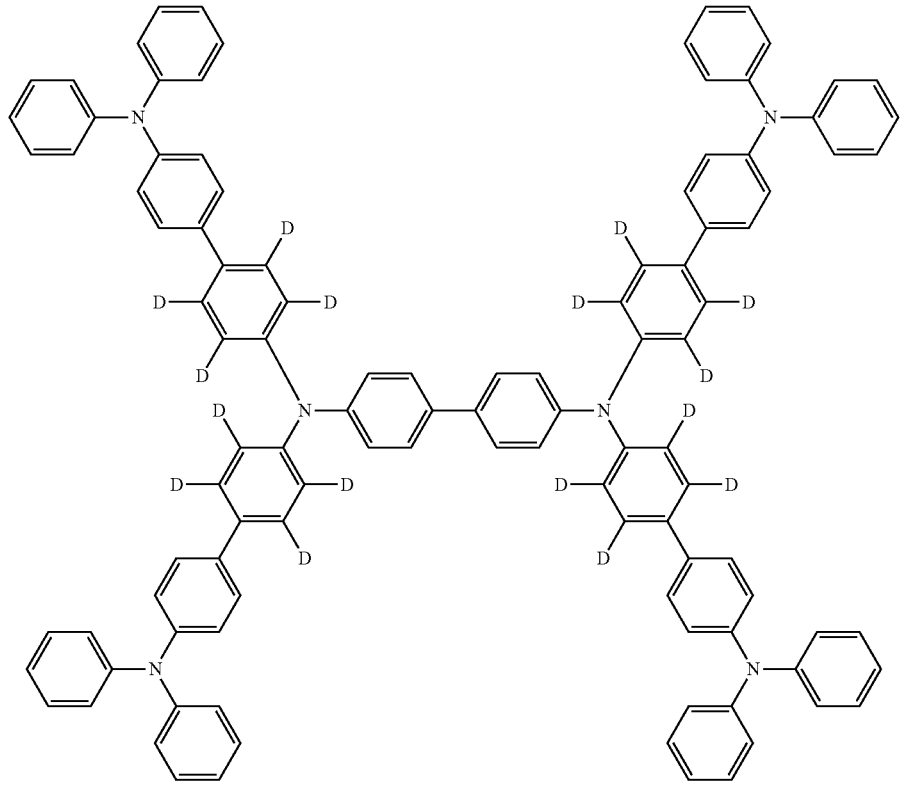
[Chemical 101]
(3-17)
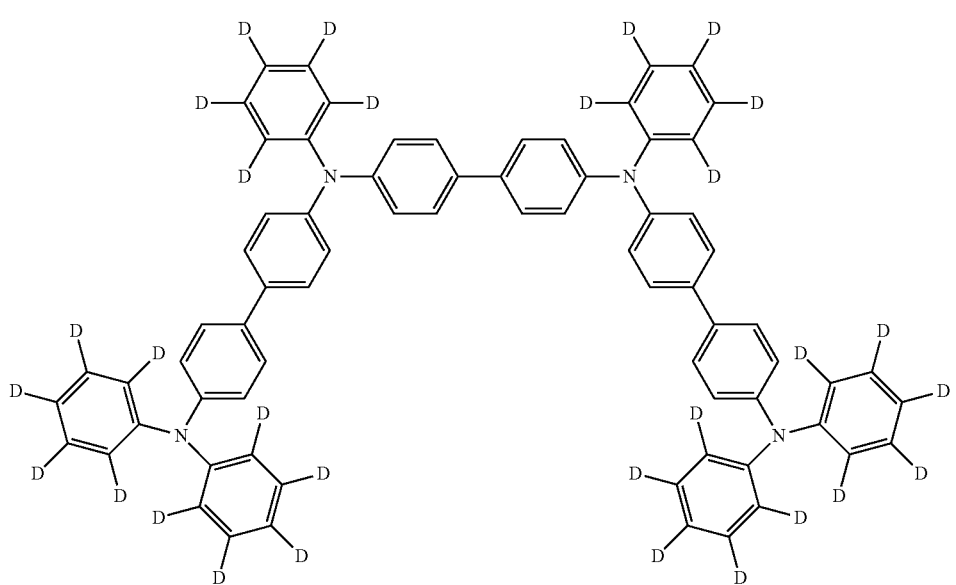

[Chemical 102]
(3-18)
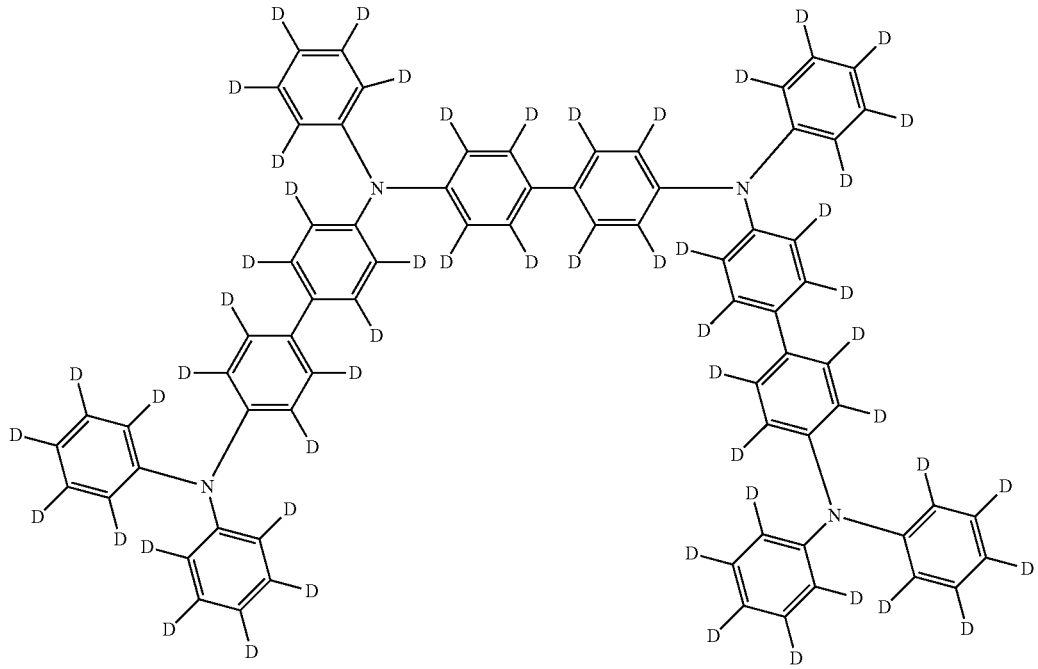
[Chemical 103]
(3-19)
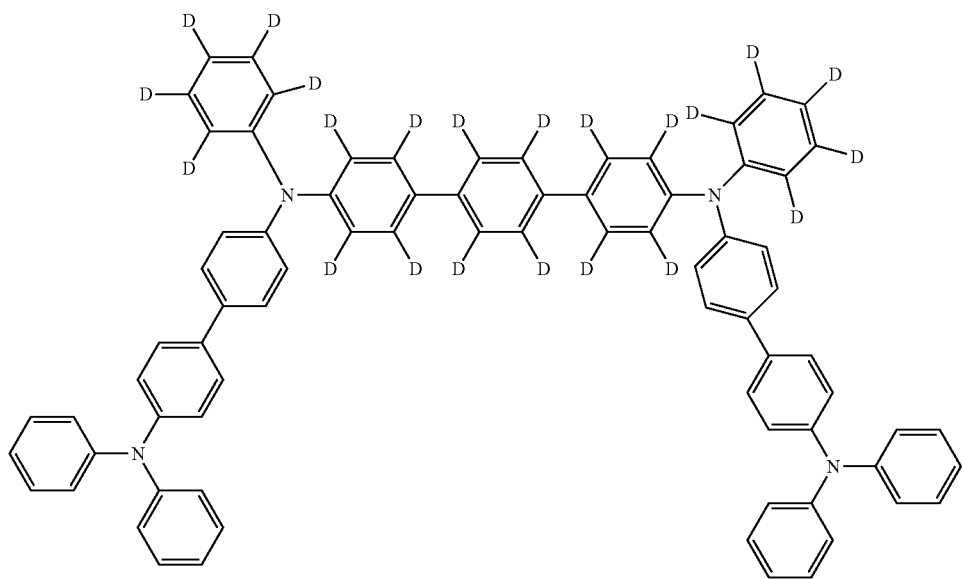

[Chemical 104]
(3-20)
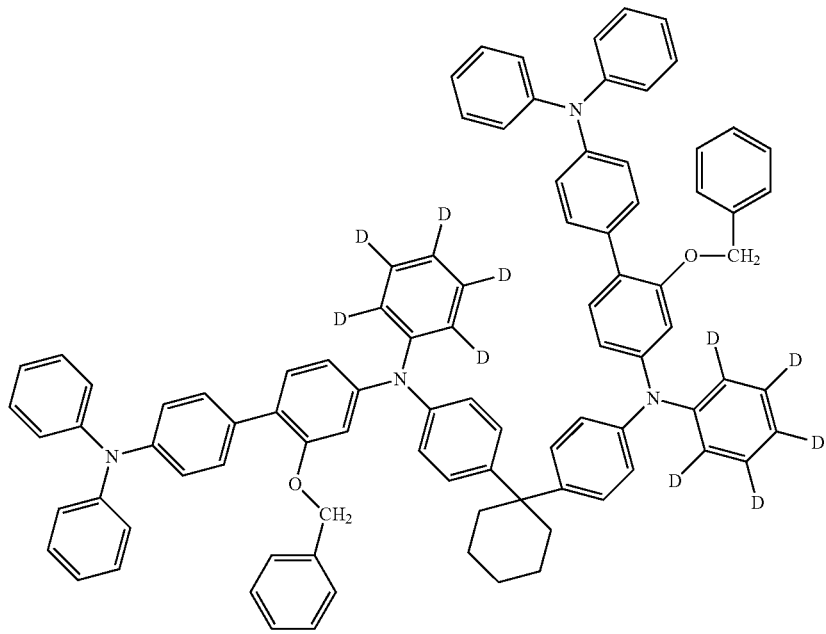
[Chemical 105]
(3-21)
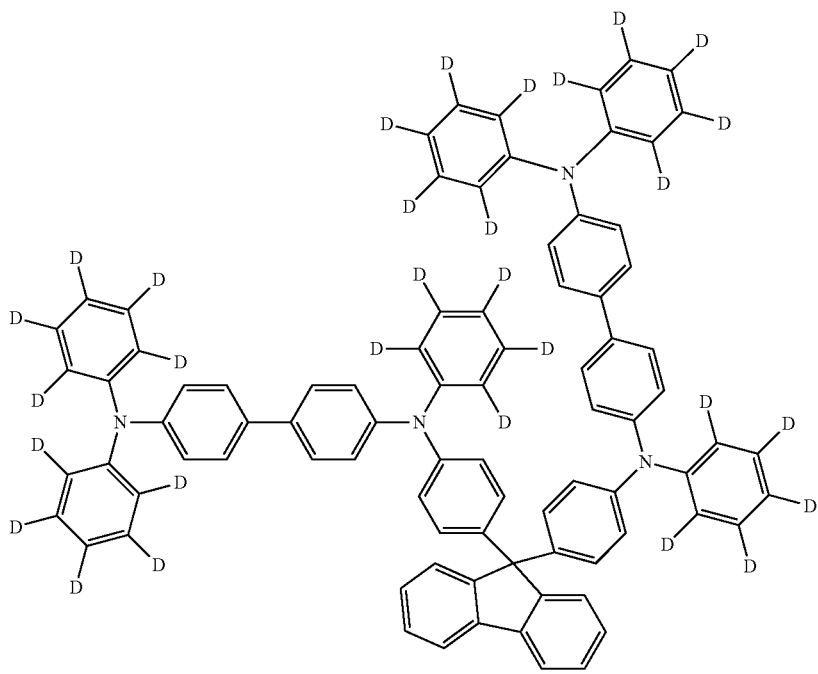

[Chemical 106]
(3-22)
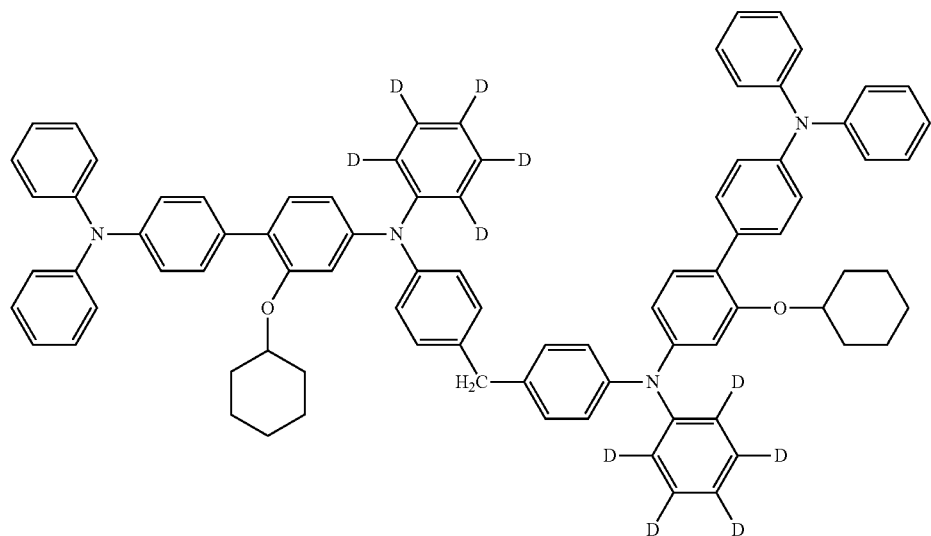
[Chemical 107]
(3-23)
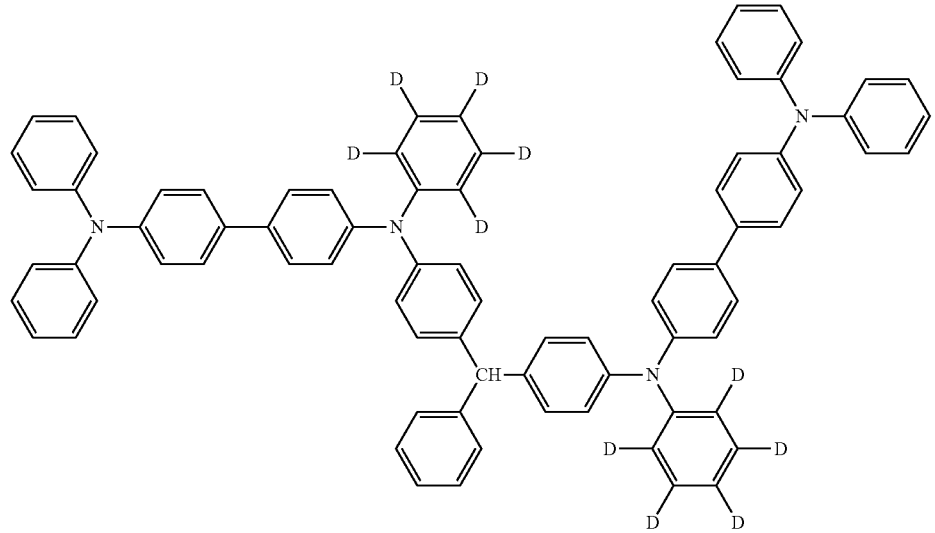
Although not having four triphenylamine skeletons as represented by the above general formula (3), there can be, further, preferably used the arylamine compounds (α) having three triphenylamine skeletons as represented by the following formulas (3'-1) to (3'-7) for forming the hole injection layer.

[Chemical 108]
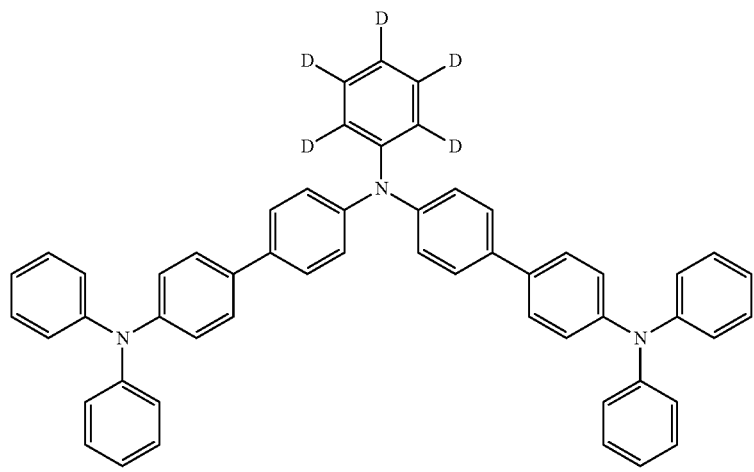
(3'-1)
[Chemical 109]
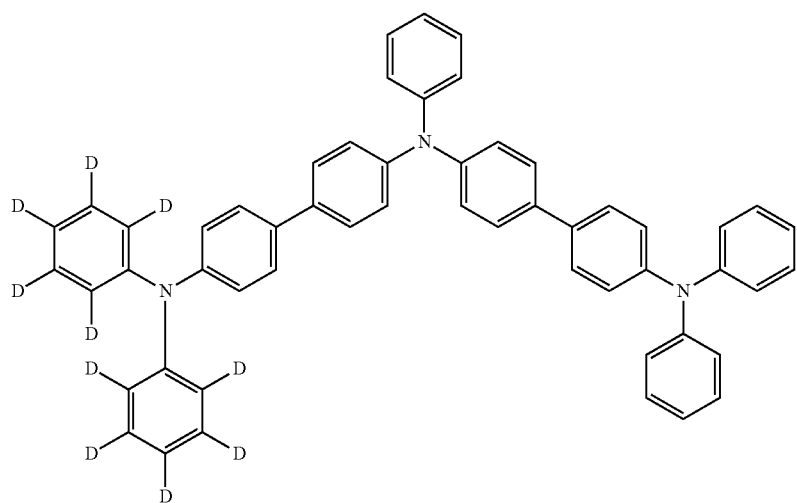
(3'-2)
[Chemical 110]
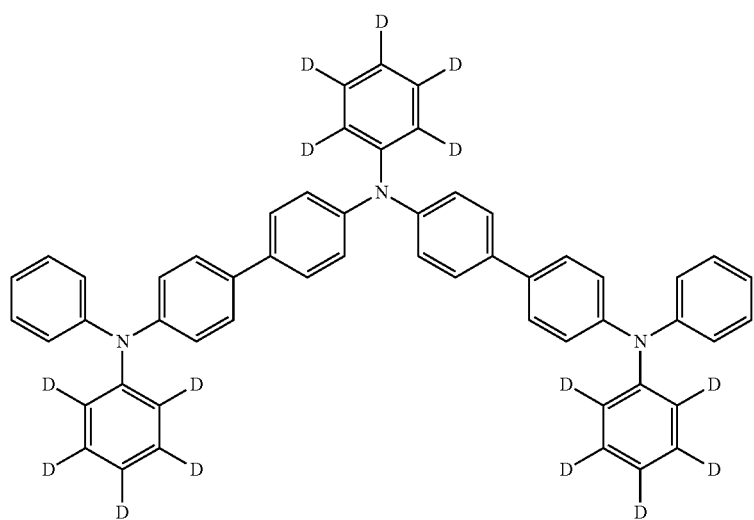
(3'-3)

[Chemical 111]
(3'-4)
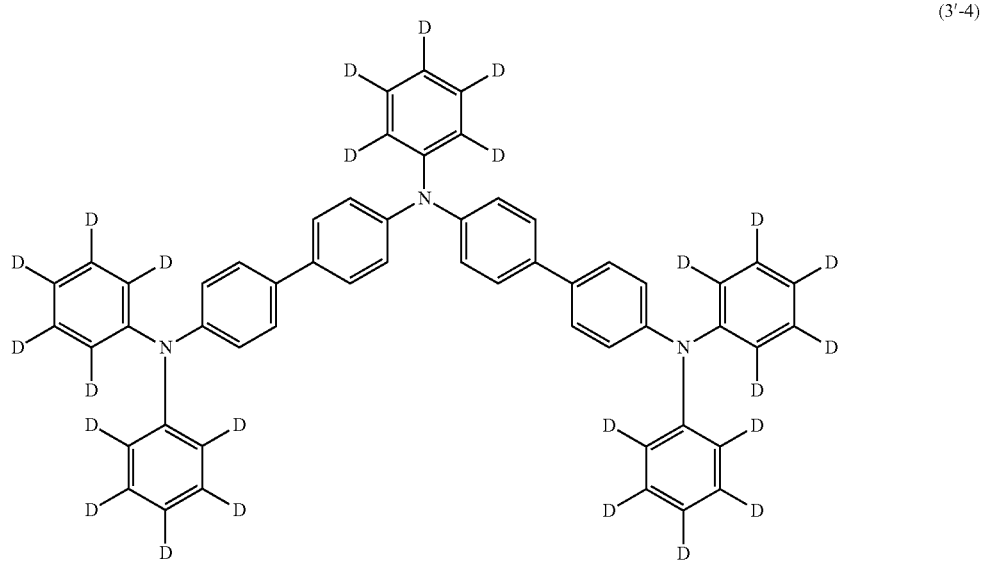
[Chemical 112]
(3'-5)
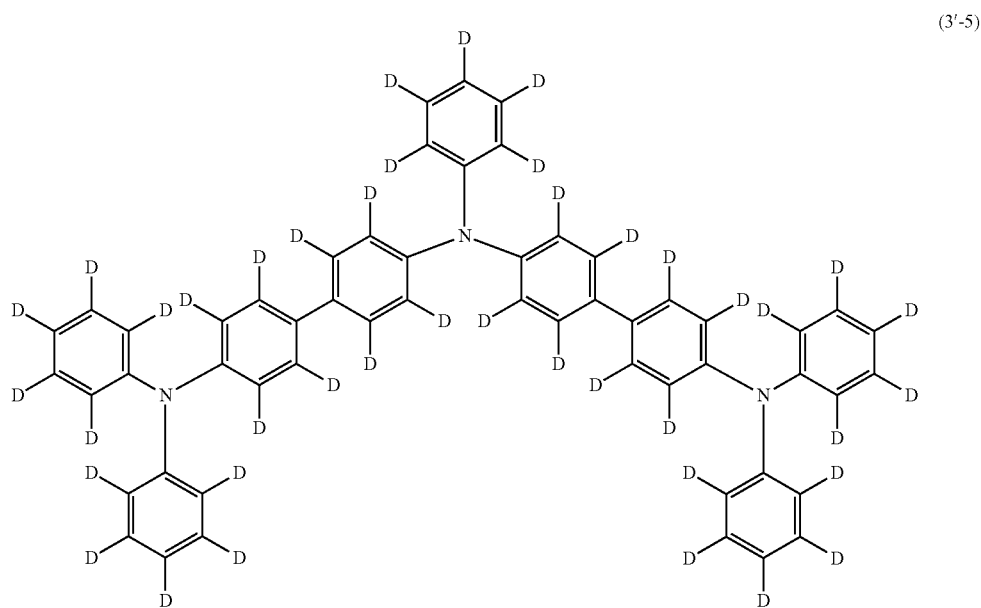

[Chemical 113]
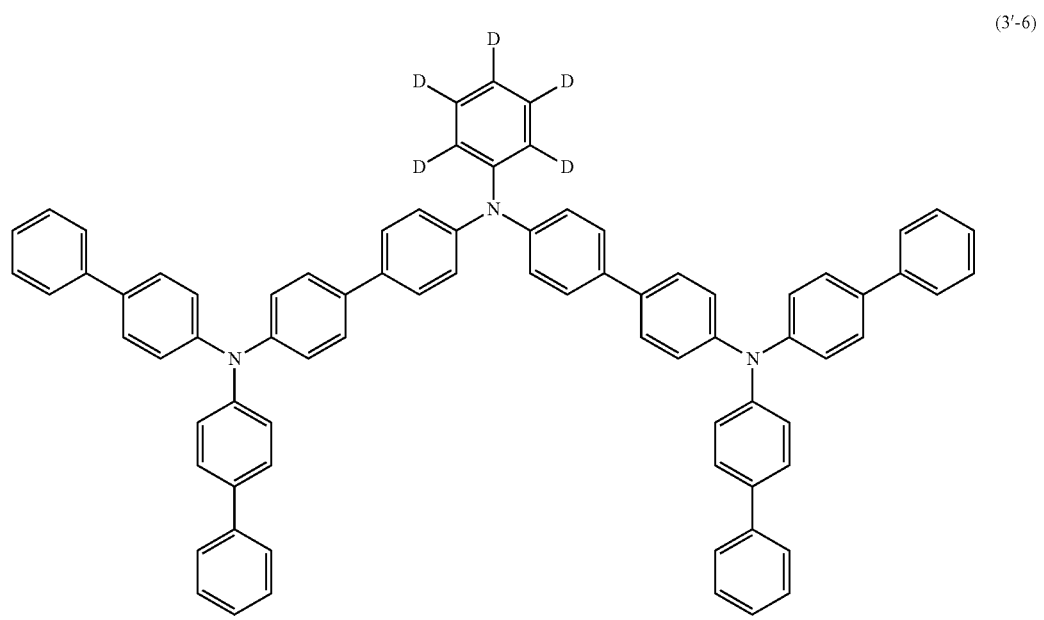
(3'-6)
[Chemical 114]
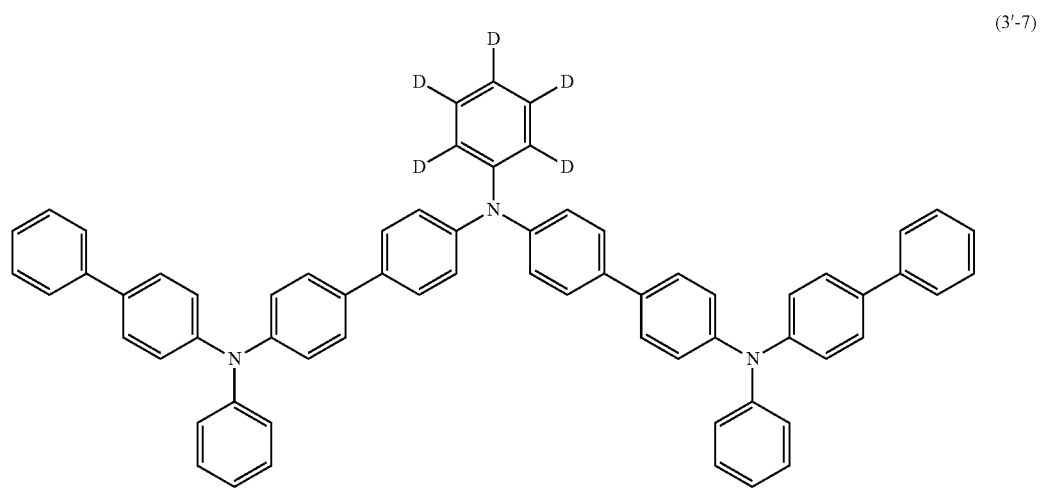
(3'-7)

<Arylamine Compounds (β)>

The invention uses the arylamine compound (β) having a molecular structure in which two triphenylamine skeletons are bonded together through a single bond or a divalent hydrocarbon group (i.e., a divalent group without hetero atom) as a compound for forming the hole-transporting layer.

The arylamine compound (β) is represented by, for example, the following general formula (4).

[Chemical 115]

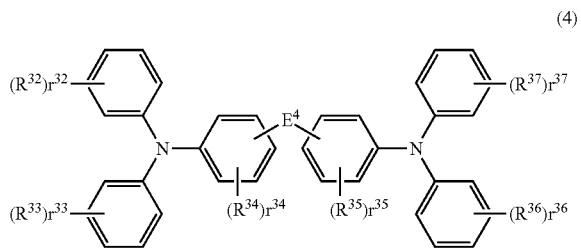

(4)

($R^{32}$ to $R^{37}$ and $r^{32}$ to $r^{37}$)

In the above general formula (4), $r^{32}$ to $r^{37}$ represent the numbers of the groups $R^{32}$ to $R^{37}$ that can be bonded to the benzene rings in the molecule, wherein $r^{32}$, $r^{33}$, $r^{36}$ and $r^{37}$ are integers of 0 to 5 while $r^{34}$ and $r^{35}$ are integers of 0 to 4. Namely, if $r^{32}$ to $r^{37}$ have a value 0, it means that none of the groups $R^{32}$ to $R^{37}$ are bonded to the benzene rings.

$R^{32}$ to $R^{37}$ are, respectively, deuterium atoms, fluorine atoms, chlorine atoms, cyano groups, trifluoromethyl groups, unsubstituted alkyl groups having 1 to 6 carbon atoms, unsubstituted or substituted alkenyl groups having 1 to 6 carbon atoms, unsubstituted or substituted aromatic hydrocarbon groups, or unsubstituted or substituted aromatic heterocyclic groups. When $R^{32}$ to $R^{37}$ are present in plural numbers (when $r^{32}$ to $r^{37}$ are 2 or more), they may be bonded together to form rings.

In the above $R^{32}$ to $R^{37}$, the unsubstituted alkyl groups having 1 to 6 carbon atoms or the unsubstituted alkenyl groups having 2 to 6 carbon atoms may be straight chains or branched and can, concretely, be the same alkyl groups or the alkenyl groups as those exemplified for $R^{17}$ to $R^{28}$ in the general formula (3).

Concrete examples of the aromatic hydrocarbon group or the aromatic heterocyclic group may be the same groups as those exemplified for $R^{17}$ to $R^{28}$.

[Chemical 117]

Further, the above alkenyl group, aromatic hydrocarbon group and aromatic heterocyclic group may have substituents which may be the same groups as the substituents exemplified for $R^{17}$ to $R^{28}$.

When some of the groups $R^{32}$ to $R^{37}$ are present in plural numbers and are bonded together to form rings, they may be bonded together through a single bond to form rings or may be bonded together through a methylene group that may have a substituent or through an oxygen atom or a sulfur atom to form rings. Specifically, it is desired that the groups are bonded together through a dimethylmethylene group to form ring.

In the invention, it is desired that at least any one of $R^{32}$ to $R^{37}$ is a deuterium atom or a substituent containing a deuterium atom (e.g., alkanyl group having a deuterium atom as a substituent, aromatic hydrocarbon group or aromatic heterocyclic group).

($E^4$)

In the general formula (4), $E^4$ is the same as $E^1$ to $E^3$ in the above general formula (3) and represents a single bond or a divalent hydrocarbon group.

As described earlier concerning $E^1$ to $E^3$, the divalent hydrocarbon group is expressed by the following formulas.

[Chemical 116]

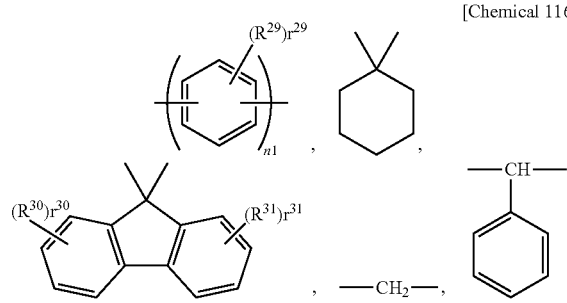

In the above formulas, n1 is an integer of 1 to 3, and $r^{29}$, $r^{30}$ and $r^{31}$ representing the numbers of $R^{29}$, $R^{30}$ and $R^{31}$ are, respectively, integers of 0 to 4. Further, $R^{29}$, $R^{30}$ and $R^{31}$ are, respectively, the same atoms or groups as those represented by $R^{17}$ to $R^{28}$ above.

Concrete examples of the arylamine compound (β) of the general formula (4).

As the arylamine compound (β) represented by the above general formula (4), there can be concretely exemplified the following compounds (4-1) to (4-23) though not limited thereto only.

[Chemical 118]

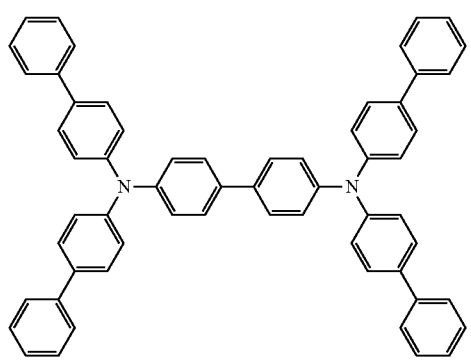

(4-1)

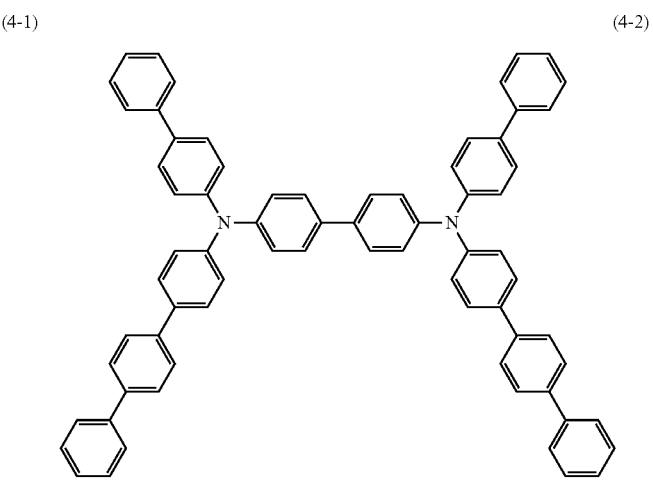

(4-2)

[Chemical 119]
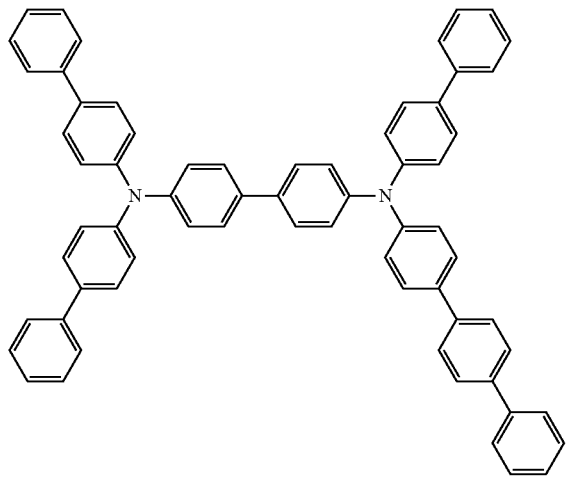
(4-3)
[Chemical 120]
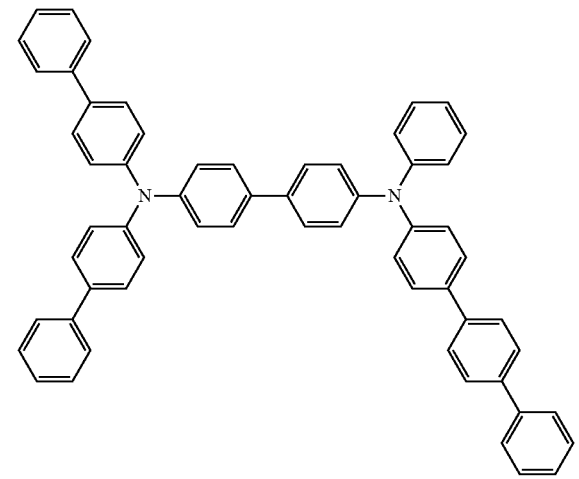
(4-4)
[Chemical 121]
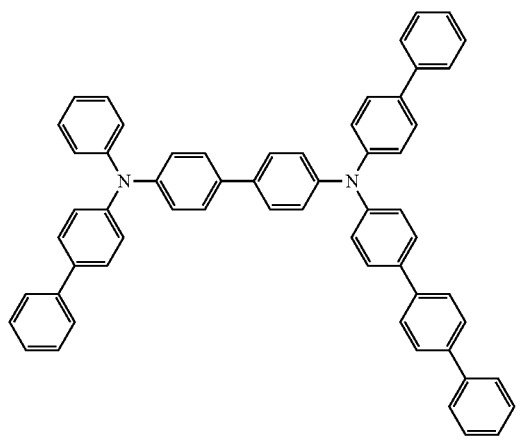
(4-5)
[Chemical 122]
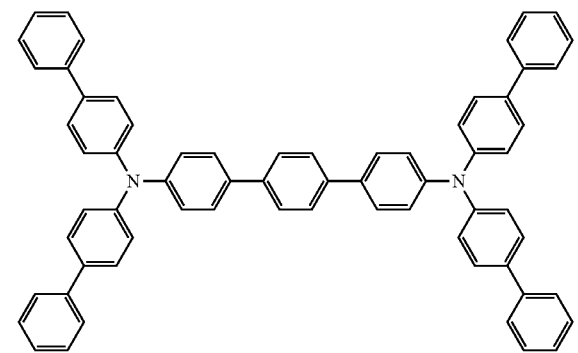
(4-6)
[Chemical 123]
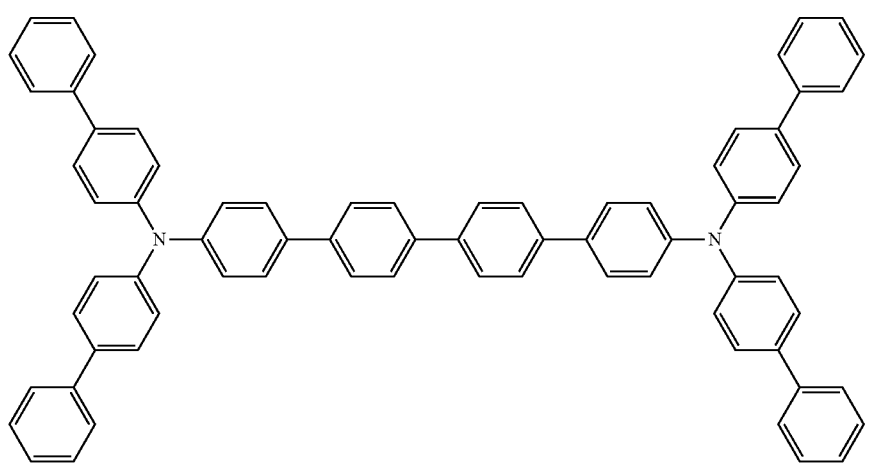
(4-7)

[Chemical 124]
(4-8)
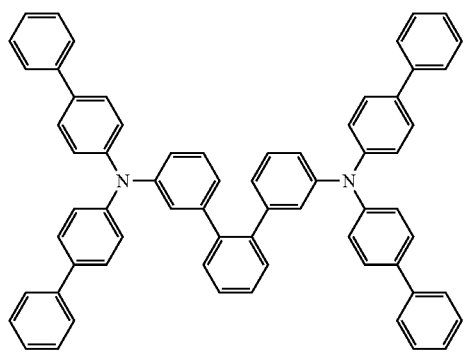
[Chemical 125]
(4-9)
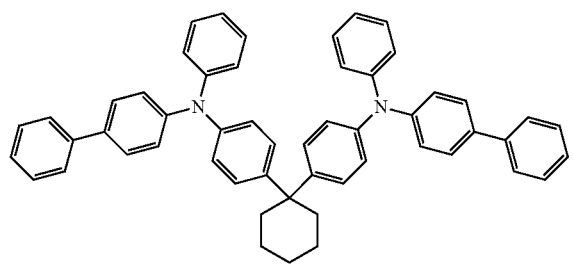
[Chemical 126]
(4-10)
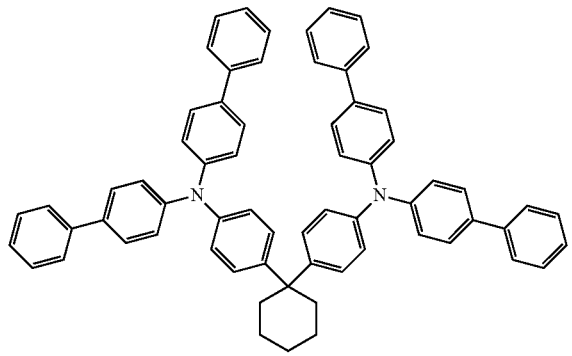
[Chemical 127]
(4-11)
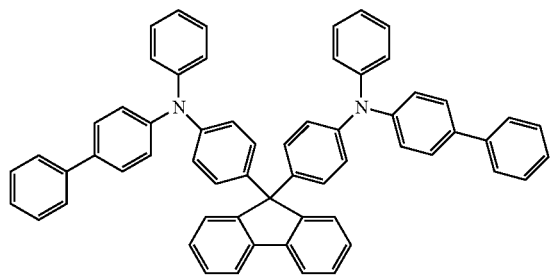
[Chemical 128]
(4-12)
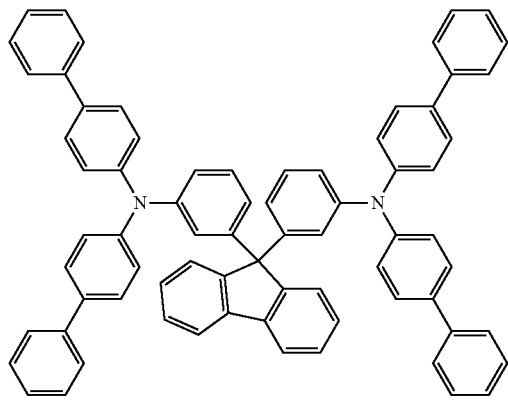
[Chemical 129]
(4-13)
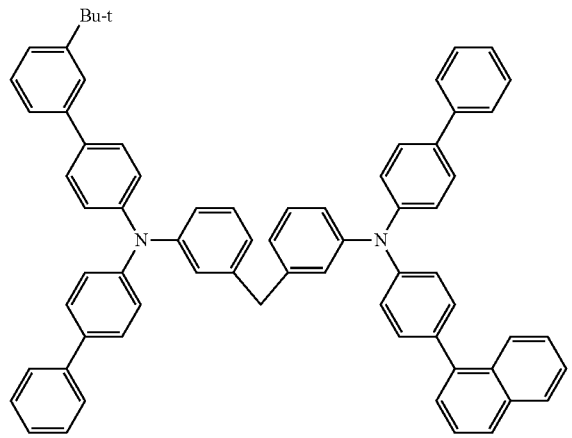

-continued
[Chemical 130]
(4-14)
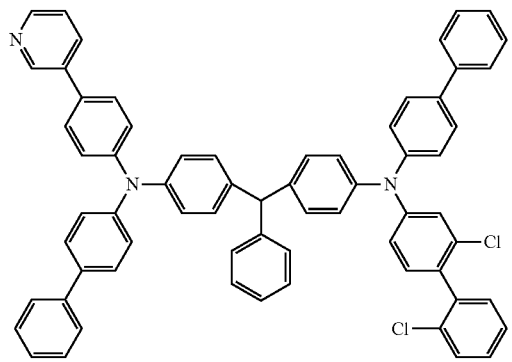
[Chemical 131]
(4-15)
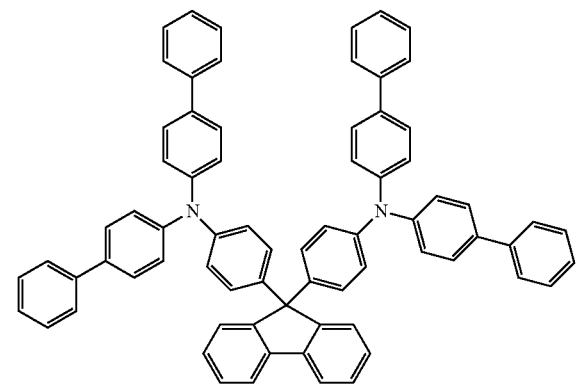
[Chemical 132]
(4-16)
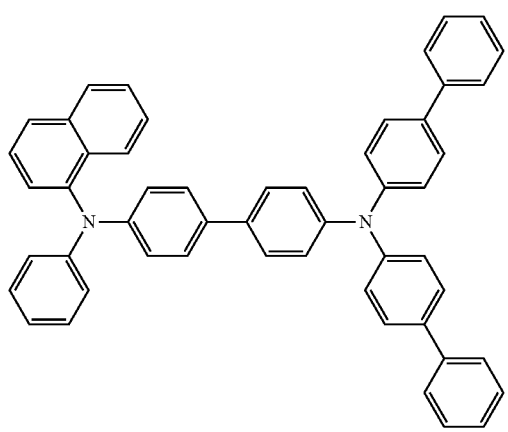
[Chemical 133]
(4-17)
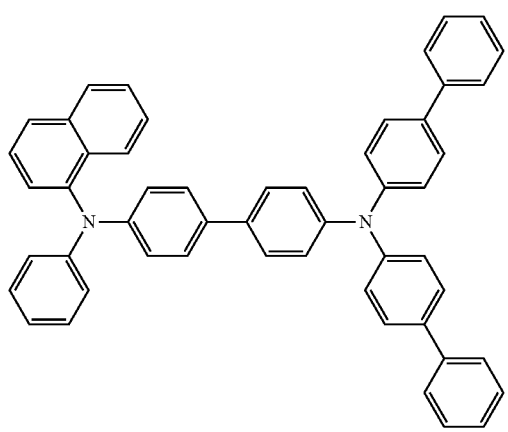
[Chemical 134]
(4-18)
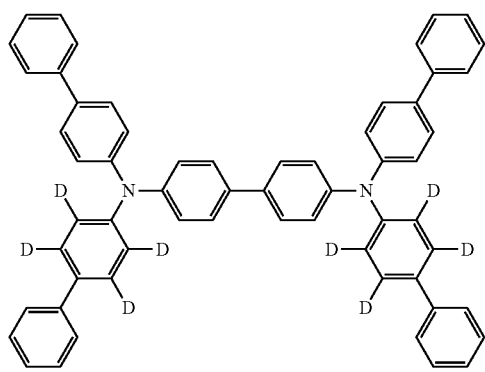
[Chemical 135]
(4-19)
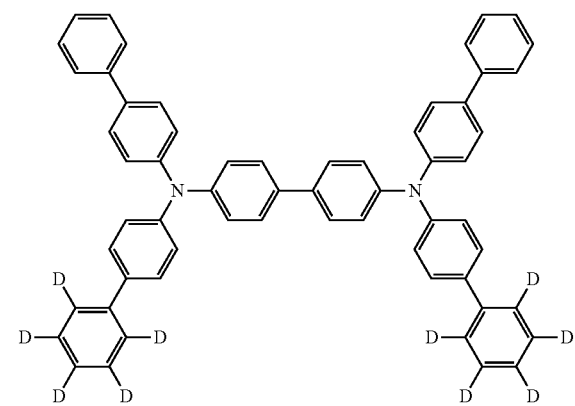

[Chemical 136]

(4-20)

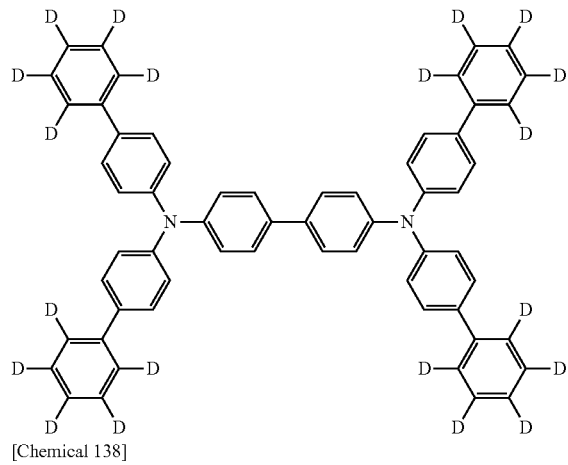

[Chemical 137]

(4-21)

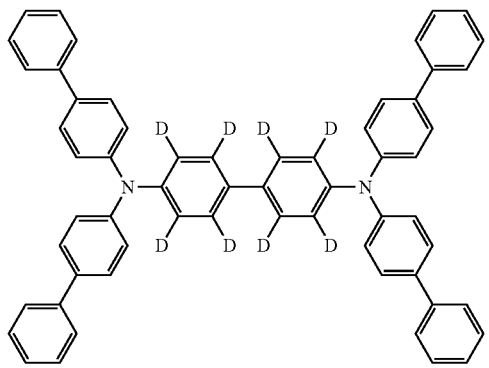

[Chemical 138]

(4-22)

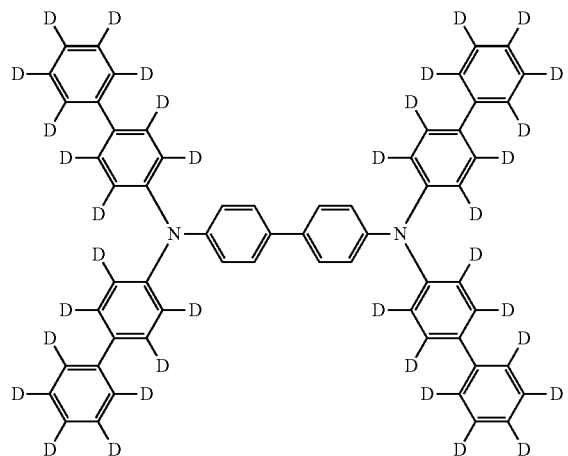

[Chemical 139]

(4-23)

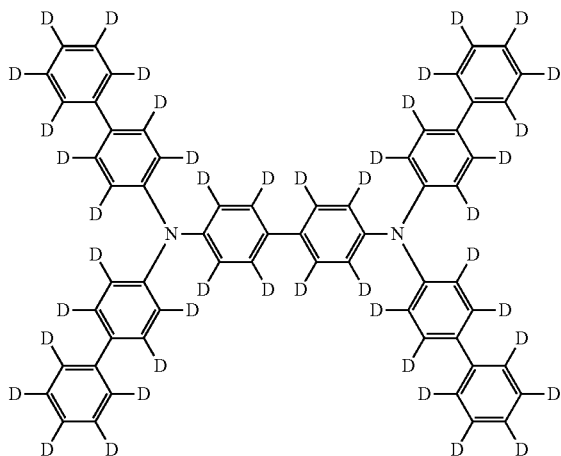

In addition to those represented by the above general formula (4), there can be, further, preferably used the arylamine compounds (β) having two triphenylamine skeletons as represented by the following formulas (4'-1) and (4'-2) for forming the hole-transporting layer.

[Chemical 140]

(4'-1)

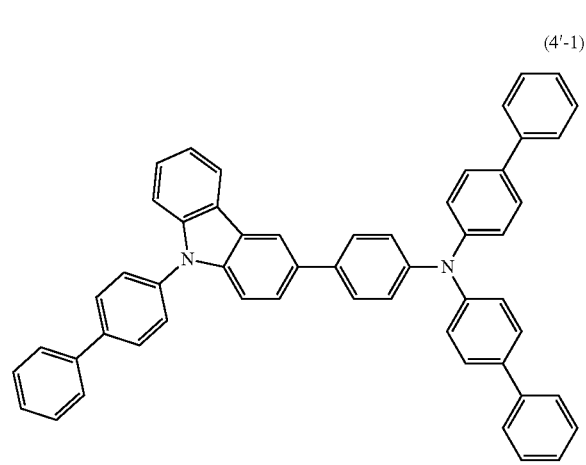

[Chemical 141]

(4'-2)

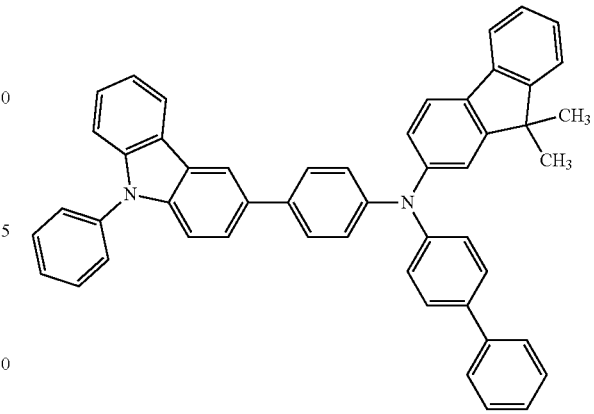

<Structure of the Organic EL Device>

The organic EL device of the invention has a basic structure in which a hole injection layer, a hole-transporting layer, a luminous layer and an electron-transporting layer are formed in this order between an anode and a cathode, the hole injection layer being formed by using the arylamine compound (α) having triphenylamine skeletons, the hole-transporting layer being formed by using the arylamine compound (β) having triphenylamine skeletons, and the electron-transporting layer being formed by using the electron-transporting compound of the above general formula (1) or (2).

The layers constituting the organic EL device will now be described.

<Anode and Cathode>

In the organic EL device of the invention, the anode is formed by being vapor-deposited on a transparent substrate such as transparent plastic substrate (e.g., polyethylene terephthalate substrate) or glass substrate by using an electrode material having a large work function such as ITO or gold.

As the cathode, use is made of a metal having a low work function, such as aluminum, or an alloy having a lower work function, such as magnesium-silver alloy, magnesium-indium alloy or aluminum-magnesium alloy.

<Hole Injection Layer>

The hole injection layer is formed by using the above arylamine compound (α), i.e., by using the compound having three or more triphenylamine skeletons in the molecule. Namely, the arylamine compound (α) has a very large hole mobility and is capable of maintaining stability in the form of a thin film. Upon forming the hole injection layer by using the above compound, therefore, it is allowed to improve the luminous efficiency, to lower the driving voltage and to lengthen the service life.

In the invention, further, it is allowed to use any other compounds that have been known as materials for forming the hole injection layer, such as porphyrin as represented by cupper phthalocyanine, heterocyclic acceptor compound such as hexacyanoazatriphenylene, or application type (organic solvent-soluble) high molecular materials in combination with the above-mentioned arylamine compound (α) so far as they do not impair the properties such as luminous efficiency, driving voltage or durability. The other compounds can be used in the form of a mixture with the arylamine compound (α) to form the hole injection layer. In this case, the amount of addition thereof should be so small as not more than 50% by weight per the arylamine compound (α). Further, the other compounds can be formed as a single layer or a plurality of layers being laminated on the layer of the arylamine compound (α).

<Hole-Transporting Layer>

The hole-transporting layer is formed neighboring the hole injection layer by using the above arylamine compound (β), i.e., the compound having two triphenylamine skeletons in the molecule.

Like the above hole injection layer, the hole-transporting layer, too, may be formed by also using the arylamine compound (β) together with other hole-transporting compounds. The other compounds can be used in the form of a mixture with the arylamine compound (β) to form the hole-transporting layer. In this case, the other compounds should be used in amounts by which they do not impair the properties of the organic EL device of the invention (e.g., in amounts of not more than 50% by weight per the arylamine compound (β)). Further, the other hole-transporting compounds can be formed as a single layer or a plurality of layers being laminated on the layer of the arylamine compound (β).

<Luminous Layer>

The luminous layer is the same as the one used in the conventional organic EL devices, and is formed by using, for example, metal complexes of quinolinol derivatives such as $Alq_3$, complexes of various metals such as zinc, beryllium and aluminum, and luminous materials such as anthracene derivative, bisstyrylbenzene derivative, pyrene derivative, oxazole derivative and polyparaphenylenevinylene derivative. The luminous layer can be, further, formed by using the compound having anthracene skeletons and pyridoindole skeletons as represented by the above-mentioned general formula (1) or (2).

The luminous layer can also be formed by using a host material and a dopant material (guest material). As the host material, in this case, there can be used thiazole derivative, benzimidazole derivative, and polydialkylfluorene derivative in addition to the above-mentioned luminous materials. As the dopant material, there can be used quinacridone, cumalin, rubrene, perylene and derivatives thereof, benzopyran derivative, rhodamine derivative and aminostyryl derivative.

As the guest material, further, there can be used a luminous phosphor. As the luminous phosphor, there can be used a luminous phosphor of a metal complex of iridium or platinum. For instance, there can be used a green luminous phosphor such as $Ir(ppy)_3$, a blue luminous phosphor such as Flrpic or $Flr_6$, and a red luminous phosphor such as $Btp_2Ir$ (acac).

As the host material, in this case, there can be used a hole injection/transport host material of a carbazole derivative, such as 4,4'-di(N-carbazolyl)biphenyl (CBP), TCTA or mCP, and there can be, further, used an electron-transporting host material such as p-bis(triphenylsilyl)benzene (UGH2) or 2,2',2"-(1,3,5-phenylene)-tris(1-phenyl-1H-benzimidazole) (TPBI). By using such host materials, it is allowed to fabricate an organic EL device of high performance.

To avoid the concentration quenching, the host material is desirably doped with the luminous phosphor in an amount in a range of 1 to 30% by weight relative to the whole luminous layer relying on the vacuum coevaporation.

The luminous layer is not limited to the one of a single-layer structure but may have a laminated structure of a lamination of layers formed by using the above-mentioned compounds.

<Electron-Transporting Layer>

In the organic EL device of the invention, the electron-transporting layer is formed by using the electron-transporting compound represented by the above-mentioned formula (1) or (2). Namely, the electron-transporting compound has the anthracene skeleton and the pyridoindole skeleton. Upon forming the electron-transporting layer by using the electron-transporting compound of the above structure, it is made possible to maintain balance in the hole injection/transport properties between the hole injection layer and the hole-transporting layer and to obtain the organic EL device that exhibits excellent properties such as luminous efficiency, driving voltage and durability (long life).

The electron-transporting layer also can be formed by combining with materials, other than the above-mentioned electron-transporting compounds, such as metal complex of quinolinol derivative like $Alq_3$, or known electron-transporting materials such as various metal complexes such as zinc, beryllium, and aluminum, triazole derivative, triazine derivative, oxadiazole derivative, thiadiazole derivative, carbodiimide derivative, quinoxaline derivative, phenanthroline derivation and silole derivative. The other electron-transporting materials can be used in the form of a mixture with the electron-transporting compound of the general formula (1) or (2) to form the electron-transporting layer. In this case, the other electron-transporting materials should be used in small amounts so will not to impair excellent properties attained by the present invention, and should be used in amounts of not more than 50% by weight per the electron-transporting compound of the general formula (1) or (2). Further, the other electron-transporting materials can be formed as a single layer or a plurality of layers being laminated on the layer formed by using the electron-transporting compound of the general formula (1) or (2).

<Other Layers>

The organic EL device of the present invention may, as required, have any other layers so far as the hole injection layer, hole-transporting layer and electron-transporting layer are formed by using the above-mentioned specific compounds. For instance, an electron-blocking layer can be provided between the hole-transporting layer and the luminous layer, a hole-blocking layer can be provided between the luminous layer and the electron-transporting layer, and an electron injection layer can be provided between the electron-transporting layer and the cathode.

Electron-Blocking Layer:

The electron-blocking layer is provided to block the passage of the injected electrons through the luminous layer. As the material for forming the electron blocking layer, there can be used various compounds having electron blocking property, and the following carbazole derivatives are representatively used.

4,4',4"-tri(N-carbazolyl)triphenylamine (TCTA),
9,9-bis[4-(carbazole-9-il)phenyl]fluorene,
1,3-bis(carbazole-9-il)benzene (mCP),
2,2-bis(4-carbazole-9-ilphenyl)adamantane (Ad-Cz).

As the material for forming the electron-blocking layer, there can be further used compounds having a triphenylsilyl group and a triarylamine skeleton in the molecules as represented by a 9-[4-carbazole-9-il]phenyl]-9-[4-(triphenylsilyl)phenyl]-9H-fluorene in addition to using the above carbazole derivatives.

Hole-Blocking Layer:

The hole-blocking layer is provided to block the passage of the injected holes through the luminous layer. The hole-blocking layer is formed by using a compound having a hole blocking action, such as a metal complex of a phenanthroline derivative like basocuproin (BCP) or quinolinol derivative like aluminum (III) bis(2-methyl-8-quinolinato)-4-phenylphenolate (BAlq), as well as various rare earth complexes, triazole derivatives, triazine derivatives and oxadiazole derivatives.

Electron Injection Layer:

The electron injection layer can be formed by using an alkali metal salt such as lithium fluoride or cesium fluoride, alkaline earth metal salt such as magnesium fluoride or a metal oxide such as aluminum oxide.

<Fabrication of the Organic EL Device>

The organic EL device of the invention having the above-mentioned structure can be fabricated by forming, on a transparent substrate, for example, an anode, a cathode, and between the anode and the cathode, a hole injection layer, a hole-transporting layer, a luminous layer, an electron-transporting layer and, as required, an electron-blocking layer, a hole-blocking layer and an electron injection layer by known methods such as vacuum evaporation method, spin-coating method and ink-jet method depending upon the kinds of the materials.

EXAMPLES

The invention will now be concretely described below by way of Examples to which only, however, the invention is in no way limited.

Example 1

Synthesis of an 8-(9,10-diphenylanthracene-2-il)-5-phenyl-5H-pyrido[4,3-b]indole [compound (2-1)]

Into a reactor purged with nitrogen, there were added:

| | |
|---|---|
| iodobenzene, | 43.0 ml |
| 5H-pyrido[4,3-b]indole, | 50.0 g |
| copper powder, | 1.9 g |
| potassium carbonate, | 82.2 g |
| dimethyl sulfoxide, | 2.1 ml | which were then heated at 170° C. and stirred for 3 hours. After cooled down to 100° C., 500 ml of toluene was added thereto, and the mixture was stirred at 100° C. for one hour. The insoluble matter was removed by filtration, and the filtrate was concentrated under reduced pressure to obtain a crude product.

The crude product was refined with a column chromatography (carrier: NH silica gel, eluent: toluene) to obtain 69.9 g of a yellow liquid of 5-phenyl-5H-pyrido[4,3-b]indol (yield, 96%).

| | |
|---|---|
| Yellow liquid of the indole compound obtained above, and | 27.2 g |
| dimethylformamide, | 150 ml | were added into the reactor purged with nitrogen and to which was, further, added with stirring:

| | |
|---|---|
| N-bromosuccinimide, | 23.8 g | and the mixture was at 50° C. and stirred for 10 hours. After cooled down to room temperature, 300 ml of chloroform and 300 ml of water were added thereto and, thereafter, the organic phase was separated. The organic phase was dehydrated with anhydrous magnesium sulfate and was concentrated under reduced pressure to obtain a crude product.

The crude product was refined with the column chromatography (carrier: NH silica gel, eluent: toluene/hexane) to obtain 18.0 g of a yellow liquid of 8-bromo-5-phenyl-5H-pyrido[4,3-b]indole (yield, 50%).

| | |
|---|---|
| Brominated product of the pyridoindole obtained above, | 2.8 g |
| 9,10-Diphenylanthracene-2-boronic acid, | 3.6 g |
| tetrakis (triphenylphosphine) palladium, | 0.1 g |
| 2M potassium carbonate aqueous solution, | 22 ml |
| Toluene, | 60 ml |
| Ethanol, | 15 ml | were added to the reactor purged with nitrogen, and the mixture was heated and refluxed for 16 hours with stirring. After cooled down to room temperature, 100 ml of toluene and 100 ml of saturated brine were added thereto and the mixture was, thereafter, stirred, and the organic phase was separated.

The organic phase was dehydrated with anhydrous magnesium sulfate and was concentrated under reduced pressure to obtain a crude product.

The crude product was refined with the column chromatography (carrier: NH silica gel, eluent: toluene/hexane) to obtain 3.0 g of a yellow powder of 8-(9,10-diphenylanthracene-2-il)-5-phenyl-5H-pyrido[4,3-b]indole [compound (2-1)] (yield, 61%).

The obtained yellow powder was identified for its structure relying on the NMR. The following 28 signals of hydrogen were detected by the $^1$H-NMR (CDCl$_3$).

$\delta(ppm) = 9.39(1H)$
$= 8.52(1H)$
$= 8.36(1H)$
$= 7.98(1H)$
$= 7.84(1H)$
$= 7.74(3H)$
$= 7.50 - 7.67(16H)$
$= 7.45(1H)$
$= 7.35(2H)$
$= 7.29(1H)$ Example 2

Synthesis of an 8-{9,10-di(naphthalene-2-il)-anthracene-2-il}-5-phenyl-5H-pyrido[4,3-b]indole [compound (2-2)]

By using the brominated product of the pyridoindole, i.e., (8-bromo-5-phenyl-5H-pyrido[4,3-b]indole obtained in Example 1, the compound was synthesized in a manner as described below.

Into the reactor purged with nitrogen, there were added:

| | |
|---|---|
| the above brominated product of the pyridoindole, | 2.0 g |
| 9,10-di(naphthalene-2-il)anthracene-2-boronic acid, | 3.5 g |
| tetrakis(triphenylphosphine)palladium, | 0.4 g |
| 2M potassium carbonate aqueous solution, | 10 ml |
| toluene, | 20 ml |
| ethanol, | 5 ml | and the mixture was heated and refluxed for 5.5 hours with stirring. After cooled down to room temperature, 50 ml of toluene and 30 ml of water were added thereto and the mixture was, thereafter, stirred, and the organic phase was separated. The organic phase was dehydrated with anhydrous magnesium sulfate and was concentrated under reduced pressure to obtain a crude product.

The crude product was refined with the column chromatography (carrier: NH silica gel, eluent: toluene) to obtain 2.2 g of a yellow powder of 8-{9,10-di(naphthalene-2-il)-anthracene-2-il}-5-phenyl-5H-pyrido[4,3-b]indole [compound (2-2)] (yield, 53%).

The obtained yellow powder was identified for its structure relying on the NMR. The following 32 signals of hydrogen were detected by the $^1$H-NMR (CDCl$_3$).

$\delta(ppm) = 9.32(1H)$
$= 8.48(1H)$
$= 8.32(1H)$
$= 8.11(2H)$
$= 8.02 - 8.07(5H)$
$= 7.95(2H)$
$= 7.88(1H)$
$= 7.68 - 7.78(5H)$
$= 7.58 - 7.64(7H)$
$= 7.49(3H)$
$= 7.37(1H)$
$= 7.33(2H)$
$= 7.24(1H)$ Example 3

Synthesis of an 8-{4-[10-(naphthalene-2-il)anthracene-9-il]phenyl}-5-phenyl-5H-pyrido[4,3-b]indole [compound (1-6)]

An 8-(4-bromophenyl)-5-phenyl-5H-pyrido[4,3-b]indole was synthesized, and this pyridoindole derivative was used as the starting material.

Into the reactor purged with nitrogen, there were added:

| | |
|---|---|
| the above pyridoindole derivative, | 4.0 g |
| 10-(naphthalene-2-il)anthracene-9-boronic acid, | 4.1 g |
| tetrakis(triphenylphosphine)palladium, | 0.3 g |
| 2M potassium carbonate aqueous solution, | 15 ml |
| toluene, | 32 ml |
| ethanol, | 8 ml | and the mixture was heated and refluxed for 18 hours with stirring. After cooled down to room temperature, the precipitated product was collected by filtration. The precipitated product was dissolved in 1,2-dichlorobenzene while being heated, and the insoluble matter was removed by filtration. Thereafter, the filtrate was concentrated under reduced pressure to obtain a crude product.

The crude product was refined by recrystallization with 1,2-dichlorobenzene to obtain 2.5 g of a yellow powder of 8-{4-(10-naphthalene-2-il-anthracene-9-il)phenyl}-5-phenyl-5H-pyrido[4,3-b]indole [compound (1-6)] (yield, 40%).

The obtained yellow powder was identified for its structure relying on the NMR. The following 30 signals of hydrogen were detected by the $^1$H-NMR (CDCl$_3$).

$\delta(ppm) = 9.50(1H)$
$= 8.62(1H)$
$= 8.57(1H)$
$= 8.09(1H)$
$= 8.04(1H)$
$= 7.99(3H)$ -continued $\delta(ppm) = 7.92(2H)$ $= 7.87(2H)$ $= 7.75(2H)$ $= 7.66 - 7.72(2H)$ $= 7.55 - 7.66(9H)$ $= 7.30 - 7.40(5H)$

Example 4

Synthesis of an 8-{3-[10-(naphthalene-2-il)anthracene-9-il]phenyl}-5-phenyl-5H-pyrido[4,3-b]indole [compound (1-11)]

Like in Example 3, an 8-(3-chrolophenyl)-5-phenyl-5H-pyrido[4,3-b]indole was synthesized, and this pyridoindole derivative was used as the starting material.

Into the reactor purged with nitrogen, there were added:

| | |
|---|---|
| the above pyridoindole derivative, | 2.85 g |
| 10-(naphthalene-2-il)anthracene-9-boronic acid, | 3.35 g |
| palladium acetate, | 0.05 g |
| butyldiadamantylphosphine, | 0.17 g |
| tripotassium phosphate, | 5.11 g |
| xylene, | 29 ml | and the mixture was heated and refluxed for 26 hours with stirring. After cooled down to room temperature, 50 ml of toluene and 100 ml of water were added thereto, and the mixture was stirred and, thereafter, the organic phase was separated. The organic phase was dehydrated with anhydrous magnesium sulfate and was, thereafter, concentrated under reduced pressure to obtain a crude product.

The crude product was refined by column chromatography (carrier: NH silica gel, eluent: toluene/hexane) to obtain 1.81 g of a yellowish white powder of 8-{3-[10-(naphthalene-2-il)anthracene-9-il]phenyl}-5-phenyl-5H-pyrido[4,3-b]indole [compound (1-11)] (yield, 36.2%).

The obtained yellowish white powder was identified for its structure relying on the NMR. The following 30 signals of hydrogen were detected by the $^1$H-NMR (CDCl$_3$).

$\delta(ppm) = 9.41(1H)$ $= 8.52(2H)$ $= 8.08(1H)$ $= 8.02(1H)$ $= 8.00(1H)$ $= 7.93(2H)$ $= 7.90(1H)$ $= 7.87(2H)$ $= 7.83(1H)$ $= 7.76 - 7.73(3H)$ $= 7.62(5H)$ $= 7.56(2H)$ -continued $= 7.54 - 7.49(3H)$ $= 7.37(2H)$ $= 7.31(3H)$

Example 5

Synthesis of an 8-{4-[10-phenylanthracene-9-il]naphthalene-1-il}-5-phenyl-5H-pyrido[4,3-b]indole [compound (1-15)]

Like in Example 3, an 8-(4-bromonaphthalene-1-il)-5-phenyl-5H-pyrido[4,3-b]indole was synthesized, and this pyridoindole derivative was used as the starting material.

Into the reactor purged with nitrogen, there were added:

| | |
|---|---|
| the above pyridoindole derivative, | 4.00 g |
| 10-phenylanthracene-9-boronic acid, | 2.92 g |
| tetrakis(triphenylphosphine) palladium, | 0.51 g |
| 2M potassium carbonate aqueous solution, | 8 ml |
| dioxane, | 32 ml | and the mixture was heated and refluxed for 20 hours with stirring. After cooled down to room temperature, toluene and water were added thereto, and the mixture was stirred and, thereafter, the organic phase was separated. The organic phase was dehydrated with anhydrous magnesium sulfate and was, thereafter, concentrated under reduced pressure to obtain a crude product.

The crude product was refined by column chromatography (carrier: NH silica gel, eluent: toluene), crystallized with a mixed solvent of acetone and methanol, and was crystallized again with a mixed solvent of o-dichlorobenzene and hexane to obtain 3.20 g of a yellowish white powder of 8-{4-[10-phenylanthracene-9-il]naphthalene-1-il}-5-phenyl-5H-pyrido[4,3-b]indole [compound (1-15)] (yield, 58%).

The obtained yellowish white powder was identified for its structure relying on the NMR. The following 30 signals of hydrogen were detected by the $^1$H-NMR (CDCl$_3$).

$\delta(ppm) = 9.47(1H)$ $= 8.59(1H)$ $= 8.54(1H)$ $= 8.16(1H)$ $= 7.84 - 7.55(18H)$ $= 7.46(1H)$ $= 7.39 - 7.34(3H)$ $= 7.30 - 7.26(4H)$

Example 6

Synthesis of an 8-{4-[10-(naphthalene-1-il)anthracene-9-il]naphthalene-1-il}-5-phenyl-5H-pyrido[4,3-b]indole [compound (1-17)]

Like in Example 5, the pyridoindole derivative (8-(4-bromonaphthalene-1-il)-5-phenyl-5H-pyrido[4,3-b]indole) was used to conduct the following synthesizing reaction.

Namely, into the reactor purged with nitrogen, there were added:

| | |
|---|---|
| the above pyridoindole derivative, | 3.50 g |
| 10-(naphthalene-1-il)anthracene-9-boronic acid, | 3.26 g |
| tetrakis(triphenylphosphine) palladium, | 0.45 g |
| 2M potassium carbonate aqueous solution, | 7 ml |
| dioxane, | 30 ml | and the mixture was heated and refluxed for 20 hours with stirring. After cooled down to room temperature, toluene and water were added thereto, and the mixture was stirred and, thereafter, the organic phase was separated. The organic phase was dehydrated with anhydrous magnesium sulfate and was, thereafter, concentrated under reduced pressure to obtain a crude product.

The crude product was crystallized with a mixed solvent of toluene and hexane, refined by the adsorption by using silica gel, washed with methanol, crystallized with a mixed solvent of toluene and hexane, and was crystallized again with a mixed solvent of toluene and methanol to obtain 1.60 g of a white powder of 8-{4-[10-(naphthalene-1-il) anthracene-9-il]naphthalene-1-il}-5-phenyl-5H-pyrido[4,3-b]indole [compound (1-17)] (yield, 310).

The obtained white powder was identified for its structure relying on the NMR. The following 32 signals of hydrogen were detected by the $^1$H-NMR (CDCl$_3$).

$$\delta(ppm) = 9.48(1H)$$

$$= 8.59 - 8.56(2H)$$

$$= 8.19 - 8.04(3H)$$

$$= 7.85 - 7.46(17H)$$

$$= 7.40 - 7.25(9H)$$

Example 7

Synthesis of an 8-{4-[10-(naphthalene-2-il)anthracene-9-il]naphthalene-1-il}-5-phenyl-5H-pyrido[4,3-b]indole [compound (1-18)]

Like in Example 5, the pyridoindole derivative (8-(4-bromonaphthalene-1-il)-5-phenyl-5H-pyrido[4,3-b]indole) was used to conduct the following synthesizing reaction.

Namely, into the reactor purged with nitrogen, there were added:

| | |
|---|---|
| the above pyridoindole derivative, | 2.30 g |
| 10-(naphthalene-2-il)anthracene-9-boronic acid, | 2.31 g |
| tetrakis(triphenylphosphine) palladium, | 0.30 g |
| 2M potassium carbonate aqueous solution, | 5 ml |
| dioxane, | 18 ml | and the mixture was heated and refluxed for 20 hours with stirring. After cooled down to room temperature, toluene and water were added thereto, and the mixture was stirred and, thereafter, the organic phase was separated. The organic phase was dehydrated with anhydrous magnesium sulfate and was, thereafter, concentrated under reduced pressure to obtain a crude product.

The crude product was refined by column chromatography (carrier: NH silica gel, eluent: toluene/hexane), crystallized with a mixed solvent of toluene and hexane, washed with methanol, and was crystallized again with a mixed solvent of acetone and methanol to obtain 0.95 g of a yellow solid of 8-{4-[10-(naphthalene-2-il)anthracene-9-il]naphthalene-1-il}-5-phenyl-5H-pyrido[4,3-b]indole [compound (1-18)] (yield, 28%).

The obtained yellow solid was identified for its structure relying on the NMR. The following 32 signals of hydrogen were detected by the $^1$H-NMR (CDCl$_3$).

$$\delta(ppm) = 9.47(1H)$$

$$= 8.59(1H)$$

$$= 8.55(1H)$$

$$= 8.17 - 8.05(4H)$$

$$= 7.96(1H)$$

$$= 7.83 - 7.78(4H)$$

$$= 7.74 - 7.58(12H)$$

$$= 7.45(1H)$$

$$= 7.38(1H)$$

$$= 7.34 - 7.27(6H)$$

Example 8

An organic EL device of a structure shown in FIG. 1 was fabricated according to the procedure described below. Namely, the organic EL device had a structure in which a transparent anode 2 (ITO electrode), a hole injection layer 3, a hole-transporting layer 4, a luminous layer 5, an electron-transporting layer 6, an electron injection layer 7 and a cathode (aluminum electrode) 8 were formed by vacuum evaporation in this order on a glass substrate 1.

First, the glass substrate 1 on which the ITO (indium tin oxide) film has been formed in a thickness of 150 nm was washed with ultrasonic waves in an isopropyl alcohol for 20 minutes and was, thereafter, dried on a hot plate heated at 200° C. for 10 minutes followed by a treatment with UV ozone for 5 minutes. Thereafter, the glass substrate with ITO was placed in a vacuum evaporation machine, and the pressure therein was decreased down to 0.001 Pa or lower.

Next, the hole injection layer 3 was formed in a thickness of 20 nm by the vacuum evaporation by using the following compound (3-1) to cover the transparent anode 2.

[Chemical 142]

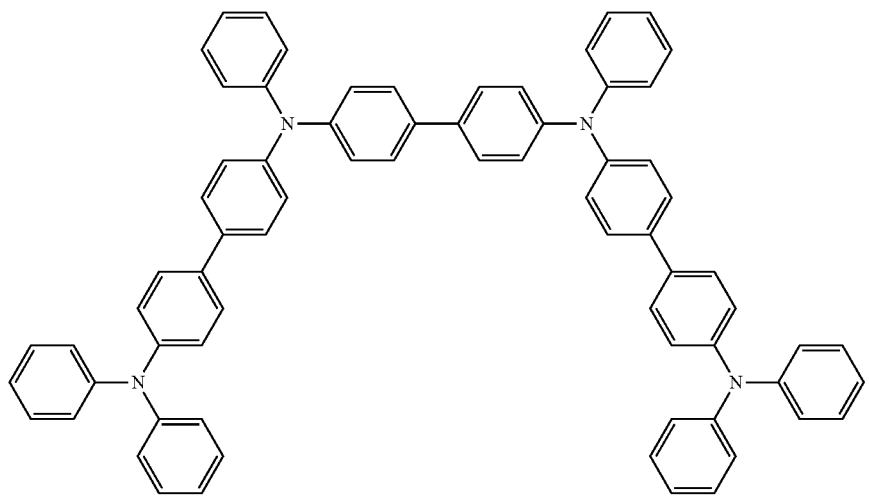

(3-1)

On the hole injection layer 3, there was formed the hole-transporting layer 4 in a thickness of 40 nm by the vacuum evaporation by using the following compound (4-1).

[Chemical 143]

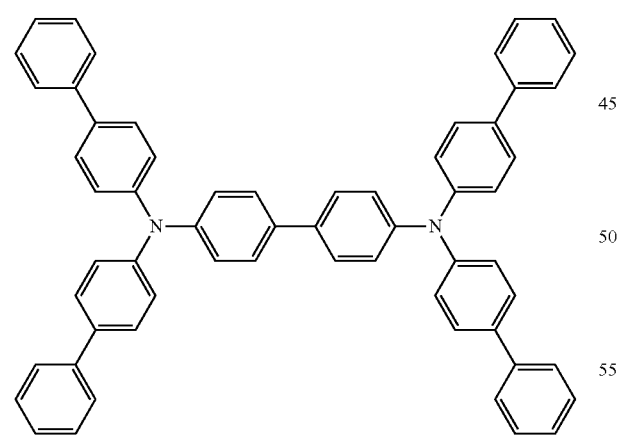

(4-1)

On the hole-transporting layer 4, there was formed the luminous layer 5 in a thickness of 30 nm by the two-way vacuum evaporation by using the following compound (5) and the compound (6) at such evaporation rates that the weight ratio thereof was 5:95.

[Chemical 144]

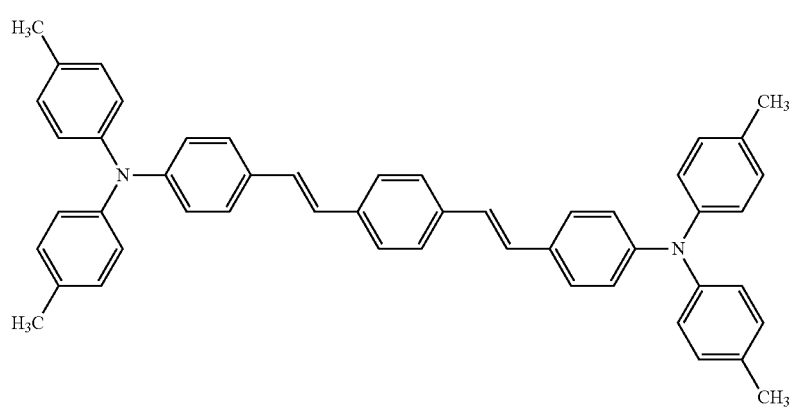

(5)

[Chemical 145]

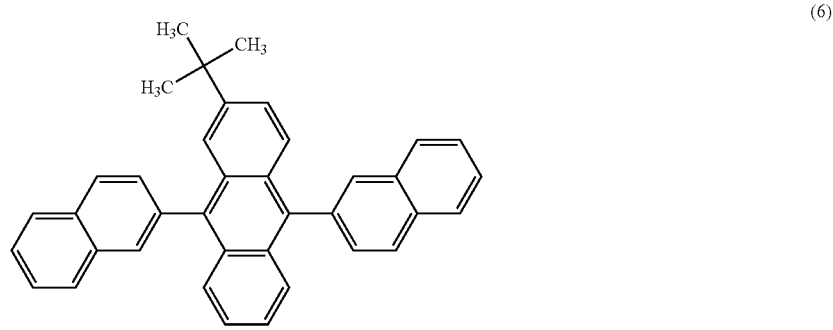

(6)

On the luminous layer 5, there was formed the electron-transporting layer 6 by vacuum evaporating the following compound (2-1) in a thickness of 30 nm.

[Chemical 146]

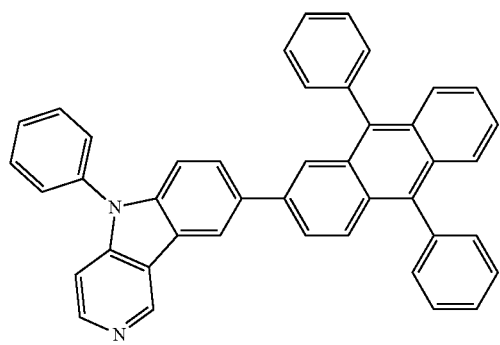

(2-1)

On the electron-transporting layer 6, there was formed the electron injection layer 7 by vacuum evaporating the lithium fluoride in a thickness of 0.5 nm.

Finally, the cathode 8 was formed by vacuum evaporating aluminum in a thickness of 150 nm.

The thus fabricated organic EL device was measured for its properties in the atmosphere at normal temperature. Table 1 summarizes the measured results of luminous properties of when a DC voltage was applied to the organic EL device.

Example 9

An organic EL device was fabricated under the same conditions as in Example 8 but forming the electron-transporting layer 6 in a thickness of 30 nm by using the compound 2-2 of the following structural formula instead of using the compound 2-1.

[Chemical 147]

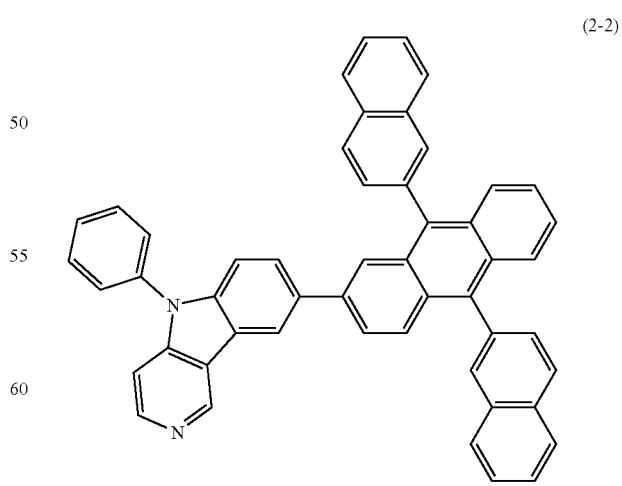

(2-2)

The thus fabricated organic EL device was measured for its properties in the atmosphere at normal temperature. Table 1 summarizes the measured results of luminous properties of when a DC voltage was applied to the organic EL device.

Example 10

An organic EL device was fabricated under the same conditions as in Example 8 but forming the electron-transporting layer 6 in a thickness of 30 nm by using the compound 1-6 of the following structural formula instead of using the compound 2-1.

[Chemical 148]

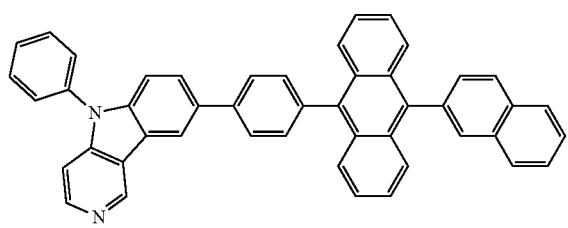

(1-6)

The thus fabricated organic EL device was measured for its properties in the atmosphere at normal temperature. Table 1 summarizes the measured results of luminous properties of when a DC voltage was applied to the organic EL device.

Example 11

An organic EL device was fabricated under the same conditions as in Example 8 but forming the electron-transporting layer 6 in a thickness of 30 nm by using the compound 1-11 of the following structural formula instead of using the compound 2-1.

[Chemical 149]

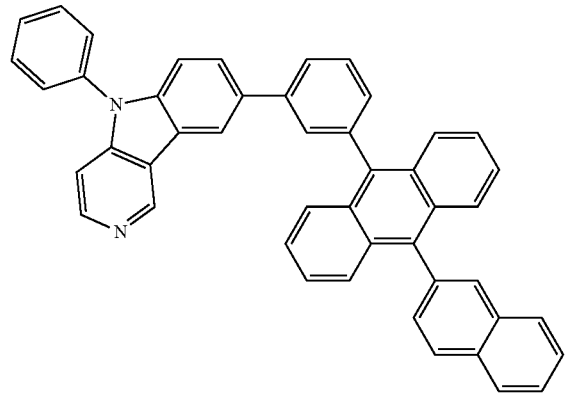

(1-11)

The thus fabricated organic EL device was measured for its properties in the atmosphere at normal temperature. Table 1 summarizes the measured results of luminous properties of when a DC voltage was applied to the organic EL device.

Example 12

An organic EL device was fabricated under the same conditions as in Example 8 but forming the electron-transporting layer 6 in a thickness of 30 nm by using the compound 1-15 of the following structural formula instead of using the compound 2-1.

[Chemical 150]

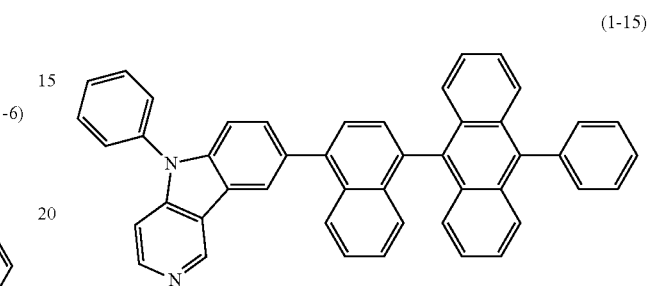

(1-15)

The thus fabricated organic EL device was measured for its properties in the atmosphere at normal temperature. Table 1 summarizes the measured results of luminous properties of when a DC voltage was applied to the organic EL device.

Example 13

An organic EL device was fabricated under the same conditions as in Example 8 but forming the electron-transporting layer 6 in a thickness of 30 nm by using the compound 1-17 of the following structural formula instead of using the compound 2-1.

[Chemical 151]

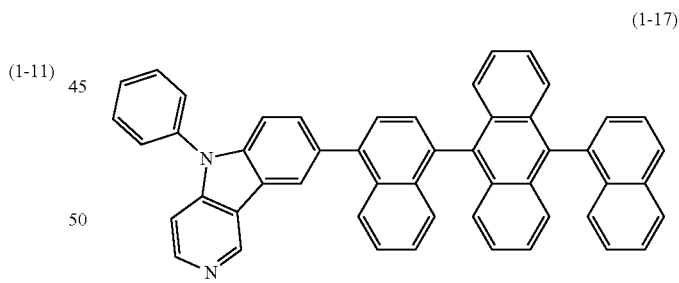

(1-17)

The thus fabricated organic EL device was measured for its properties in the atmosphere at normal temperature. Table 1 summarizes the measured results of luminous properties of when a DC voltage was applied to the organic EL device.

Example 14

An organic EL device was fabricated under the same conditions as in Example 8 but forming the electron-transporting layer 6 in a thickness of 30 nm by using the compound 1-18 of the following structural formula instead of using the compound 2-1.

[Chemical 152]

(1-18)

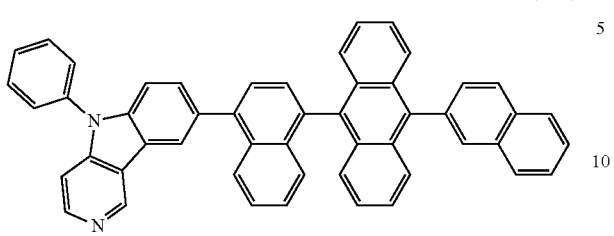

The thus fabricated organic EL device was measured for its properties in the atmosphere at normal temperature. Table 1 summarizes the measured results of luminous properties of when a DC voltage was applied to the organic EL device.

Comparative Example 1

For comparison, an organic EL device was fabricated under the same conditions as in Example 8 but forming the electron-transporting layer 6 in a thickness of 30 nm by using the Alq$_3$ instead of using the compound 2-1.

The thus fabricated organic EL device was measured for its properties in the atmosphere at normal temperature. Table 1 summarizes the measured results of luminous properties of when a DC voltage was applied to the organic EL device.

Comparative Example 2

For comparison, an organic EL device was fabricated under the same conditions as in Example 8 but forming the hole injection layer 3 in a thickness of 20 nm by using the CuPc instead of using the compound 3-1.

The thus fabricated organic EL device was measured for its properties in the atmosphere at normal temperature. Table 1 summarizes the measured results of luminous properties of when a DC voltage was applied to the organic EL device.

TABLE 1

|  | Voltage [V] (@ 10 mA/cm$^2$) | Luminous efficiency [cd/A] (@ 10 mA/cm$^2$) | Power efficiency [lm/W] (@ 10 mA/cm$^2$) |
| --- | --- | --- | --- |
| Ex. 8 | 3.94 | 9.32 | 7.43 |
| Ex. 9 | 4.15 | 9.72 | 7.36 |
| Ex. 10 | 4.18 | 9.64 | 7.24 |
| Ex. 11 | 4.37 | 8.34 | 5.99 |
| Ex. 12 | 4.31 | 10.14 | 7.39 |
| Ex. 13 | 4.78 | 8.51 | 5.59 |
| Ex. 14 | 4.17 | 9.06 | 6.82 |
| Comp. Ex. 1 | 4.87 | 7.84 | 5.06 |
| Comp. Ex. 2 | 5.40 | 8.51 | 4.95 |

From Comparative Example 1 and Comparative Example 2, it was confirmed that when the compound forming the hole injection layer was changed from the CuPc into the compound 3-1, the driving voltage decreased accompanied, however, by a decrease in the luminous efficiency. This is attributed to that the compound 3-1 has such a high hole mobility that the hole carriers increase causing a disruption in the carrier balance and a decrease in the probability of recombination.

When the compound forming the electron-transporting layer was changed to the compounds having the anthracene ring structure and the pyridoindole ring structure (compounds 2-1, 2-2, 1-6, 1-11, 1-15, 1-17 and 1-18) which are capable of quickly transporting the electron carriers, it was confirmed that the driving voltage could be further lowered, and the luminous efficiency and the power efficiency could be greatly improved as demonstrated in Examples 8 to 14. This proves that by using the material having a high hole mobility in combination with the material having a high electron carrier-transporting rate, the carrier balance is improved between the hole carriers and the electron carriers.

INDUSTRIAL APPLICABILITY

The organic EL device of the present invention features improved luminous efficiency, decreased driving voltage, improved durability, and finds a wide range of applications in the field of domestic electric appliances and lighting.

DESCRIPTION OF REFERENCE NUMERALS 1 glass substrate
2 transparent anode
3 hole injection layer
4 hole-transporting layer
5 luminous layer
6 electron-transporting layer
7 electron injection layer
8 cathode

The invention claimed is:

1. An organic electroluminescent device including, between an anode and a cathode, a hole injection layer, a hole-transporting layer, a luminous layer and an electron-transporting layer, wherein:
said hole injection layer contains an arylamine compound (α) having a molecular structure in which three or more triphenylamine skeletons are bonded together via a single bond or a divalent hydrocarbon group;
said hole-transporting layer contains an arylamine compound (β) having a molecular structure in which two triphenylamine skeletons are bonded together via a single bond or a divalent hydrocarbon group; and
said electron-transporting layer contains an electron-transporting compound having an anthracene ring skeleton and a pyridoindole ring skeleton represented by the following general formula (1) or the general formula (2), (1)

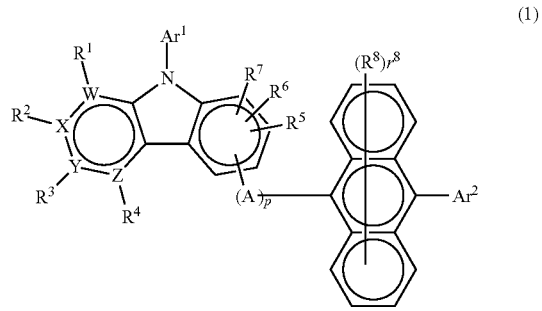

wherein,
p represents the number of the divalent groups A, and is an integer of 0 to 4,
A is a divalent unsubstituted or substituted aromatic hydrocarbon ring group or an aromatic heterocyclic group, and when p is 2 or larger, the plurality of As may be different from each other and when p is 0, A is not present, and the anthracene ring and the pyridoindole ring are bonded together via a single bond, Ar$^1$ is an unsubstituted or substituted aromatic hydrocarbon group or an aromatic heterocyclic group, Ar$^2$ is an unsubstituted or substituted aromatic hydrocarbon group, R$^1$ to R$^7$ are, respectively, hydrogen atoms, deuterium atoms, fluorine atoms, chlorine atoms, cyano groups, trifluoromethyl groups, unsubstituted alkyl groups having 1 to 6 carbon atoms, unsubstituted or substituted aromatic hydrocarbon groups or aromatic heterocyclic groups, r$^8$ which represents the number of R$^8$ is an integer of 0 to 8, R$^8$ is a deuterium atom, a fluorine atom, a chlorine atom, a cyano group, a trifluoromethyl group or an unsubstituted alkyl group having 1 to 6 carbon atoms, and when r$^8$ is a number of 2 or more, the plurality of R$^8$ may be the same or different, and W, X, Y and Z are, respectively, carbon atoms or nitrogen atoms, and only one of them is a nitrogen atom, and none of R$^1$ to R$^4$ is bonded to the nitrogen atom,

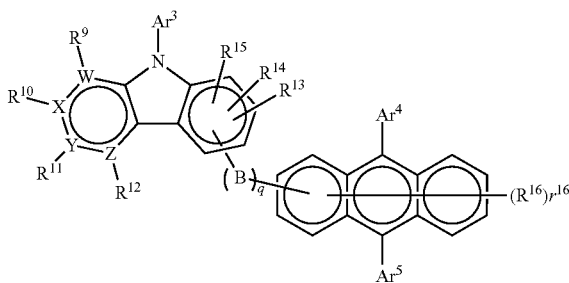

(2)

wherein, q represents the number of the divalent groups B, and is an integer of 0 to 4, B is a divalent unsubstituted or substituted aromatic hydrocarbon ring group or an aromatic heterocyclic group, and when q is 2 or larger, the plurality of Bs may be different from each other and when q is 0, B is not present, and the anthracene ring and the pyridoindole ring are bonded together via a single bond, Ar$^3$ is an unsubstituted or substituted aromatic hydrocarbon group or an aromatic heterocyclic group, Ar$^4$ and Ar$^y$ are unsubstituted or substituted aromatic hydrocarbon groups, R$^9$ to R$^{15}$ are, respectively, hydrogen atoms, deuterium atoms, fluorine atoms, chlorine atoms, cyano groups, trifluoromethyl groups, unsubstituted alkyl groups having 1 to 6 carbon atoms, unsubstituted or substituted aromatic hydrocarbon groups or aromatic heterocyclic groups, r$^{16}$ which represents the number of R$^{16}$ is an integer of 0 to 7, R$^{16}$ is a deuterium atom, a fluorine atom, a chlorine atom, a cyano group, a trifluoromethyl group or an unsubstituted alkyl group having 1 to 6 carbon atoms, and when r$^{16}$ is a number of 2 or more, the plurality of R$^{16}$ may be the same or different, and W, X, Y and Z are, respectively, carbon atoms or nitrogen atoms, and only one of them is a nitrogen atom, and none of R$^9$ to R$^{12}$ is bonded to the nitrogen atom.

2. The organic electroluminescent device according to claim 1, wherein said arylamine compound (α) is represented by the following general formula (3),

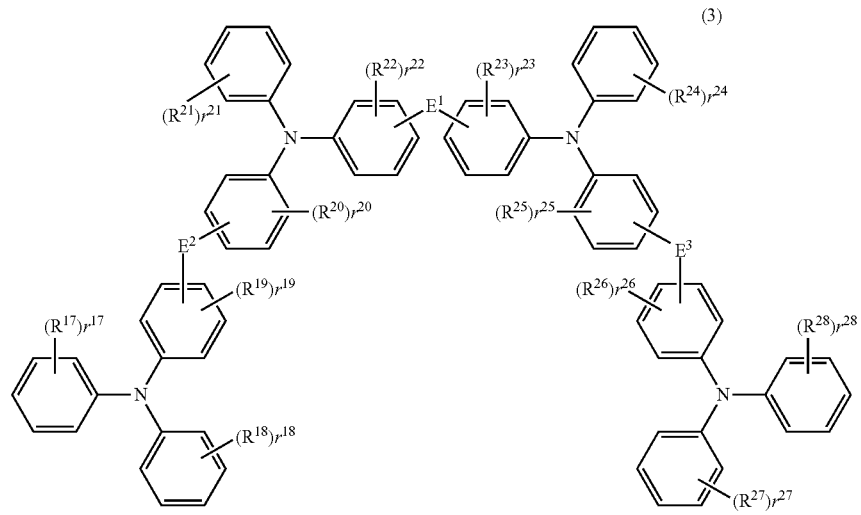

(3)

wherein, r$^{17}$ to r$^{28}$, respectively, represent the numbers of R$^{17}$ to R$^{28}$, r$^{17}$, R$^{18}$, r$^{21}$, r$^{24}$, r$^{27}$ and r$^{28}$ being integers of 0 to 5, and r$^{19}$, r$^{20}$, r$^{22}$, r$^{23}$, r$^{25}$ and r$^{26}$ being integers of 0 to 4, R$^{17}$ to R$^{28}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups or aromatic heterocyclic groups and among these groups, the groups bonded to the same benzene ring may be bonded together to form a ring, and E$^1$ to E$^3$, respectively, are single bonds or divalent groups represented by any one of the following formulas,

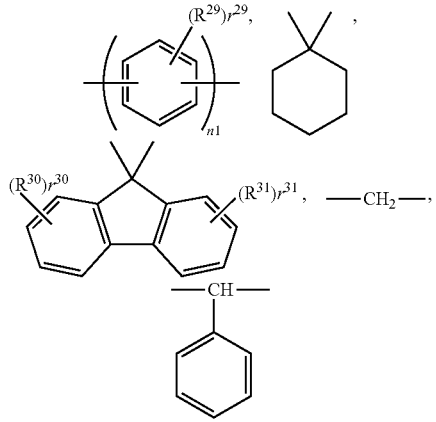

wherein, n1 is an integer of 1 to 3, r$^{29}$, r$^{30}$ and r$^{31}$ represent the numbers of R$^{29}$, R$^{30}$ and R$^{31}$, and are, respectively, integers of 0 to 4, and R$^{29}$, R$^{30}$ and R$^{31}$ are the same atoms or the groups as those of the above R$^{17}$ to R$^{28}$.

3. The organic electroluminescent device according to claim 1, wherein said arylamine compound (β) is represented by the following general formula (4),

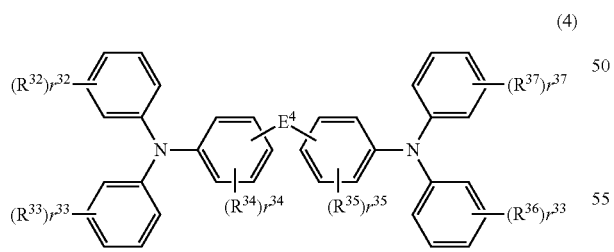

(4)

wherein, among r$^{32}$ to r$^{37}$ representing the numbers of R$^{32}$ to R$^{37}$, r$^{32}$, r$^{33}$, r$^{36}$ and r$^{37}$ are integers of 0 to 5, r$^{34}$ and r$^{35}$ are integers of 0 to 4, R$^{32}$ to R$^{37}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups or aromatic heterocyclic groups and among these groups, the groups bonded to the same benzene ring may be bonded together to form a ring, and E$^4$ is a single bond or a divalent group represented by any one of the following formulas,

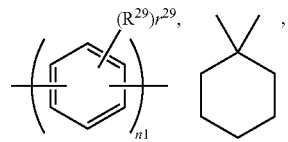

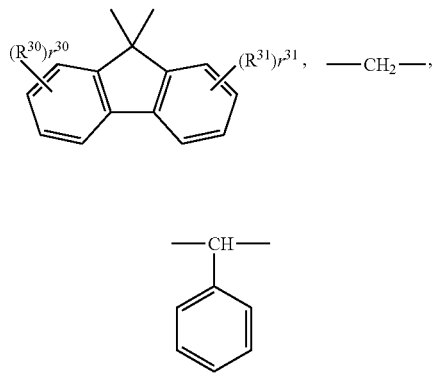

wherein, n1 is an integer of 1 to 3, r$^{29}$, r$^{30}$ and r$^{31}$ represent the numbers of R$^{29}$, R$^{30}$ and R$^{31}$, and are, respectively, integers of 0 to 4, and R$^{29}$, R$^{30}$ and R$^{31}$ are the same atoms or the groups as those of the above R$^{17}$ to R$^{28}$.

4. The organic electroluminescent device according to claim 1, wherein said electron-transporting compound is represented by the following general formula (1a),

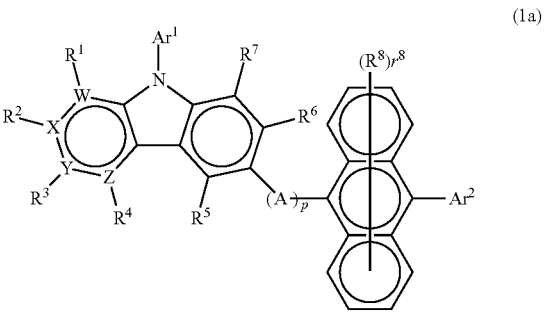

(1a)

wherein A, Ar$^1$, Ar$^2$, R$^1$ to R$^8$, p, r$^8$, W, X, Y and Z are as described in the above general formula (1).

5. The organic electroluminescent device according to claim 4, wherein said electron-transporting compound is represented by the following general formula (1b),

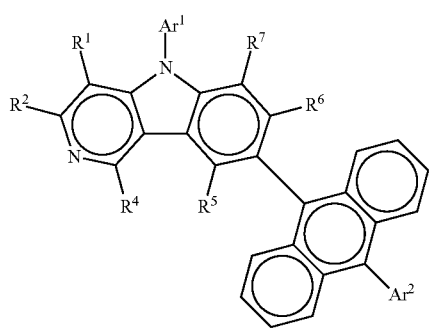

(1b)

wherein Ar$^1$, Ar$^2$, R$^1$, R$^2$ and R$^4$ to R$^7$ are as described in the above general formula (1).

6. The organic electroluminescent device according to claim 4, wherein said electron-transporting compound is represented by the following general formula (1c),

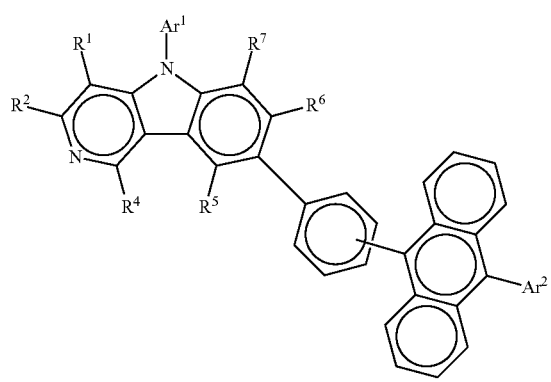

(1c)

wherein Ar$^1$, Ar$^2$, R$^1$, R$^2$ and R$^4$ to R$^7$ are as described in the above general formula (1).

7. The organic electroluminescent device according to claim 4, wherein said electron-transporting compound is represented by the following general formula (1d),

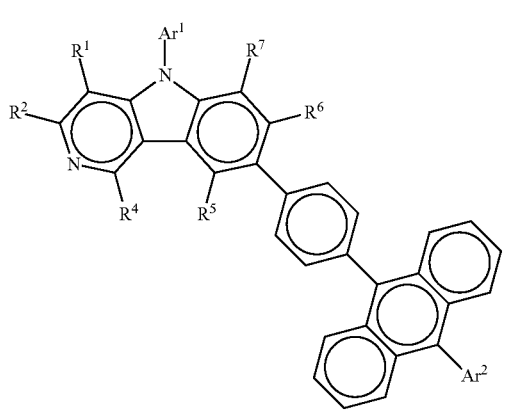

(1d)

wherein Ar$^1$, Ar$^2$, R$^1$, R$^2$ and R$^4$ to R$^7$ are as described in the above general formula (1).

8. The organic electroluminescent device according to claim 4, wherein said electron-transporting compound is represented by the following general formula (1e),

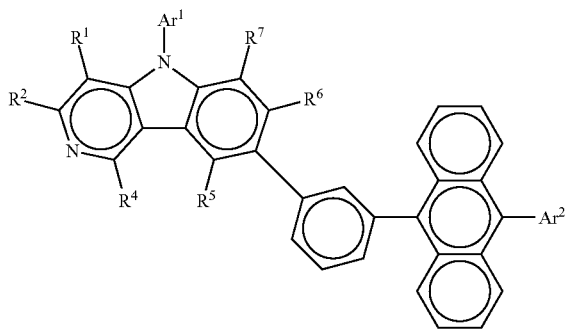

(1e)

wherein Ar$^1$, Ar$^2$, R$^1$, R$^2$ and R$^4$ to R$^7$ are as described in the above general formula (1).

9. The organic electroluminescent device according to claim 4, wherein said electron-transporting compound is represented by the following general formula (1f),

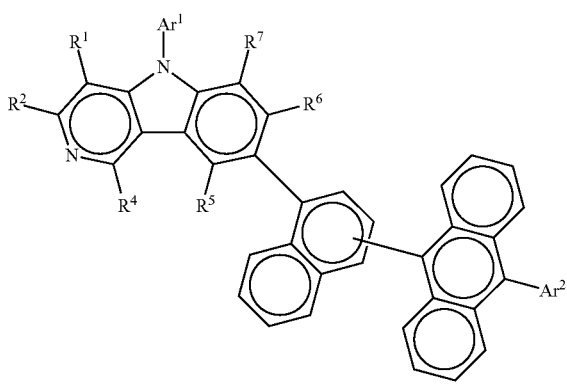

(1f)

wherein Ar$^1$, Ar$^2$, R$^1$, R$^2$ and R$^4$ to R$^7$ are as described in the above general formula (1).

10. The organic electroluminescent device according to claim 4, wherein said electron-transporting compound is represented by the following general formula (1g),

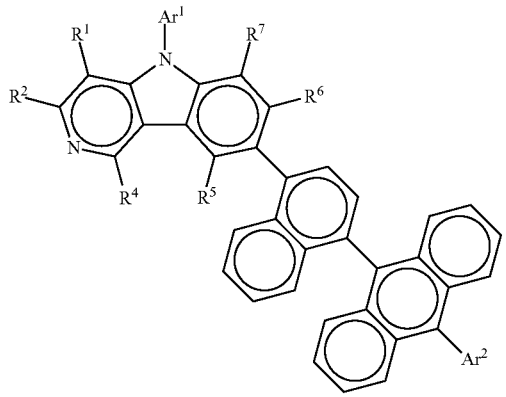

(1g)

wherein Ar$^1$, Ar$^2$, R$^1$, R$^2$ and R$^4$ to R$^7$ are as described in the above general formula (1).

11. The organic electroluminescent device according to claim 1, wherein said electron-transporting compound is represented by the following general formula (2a),

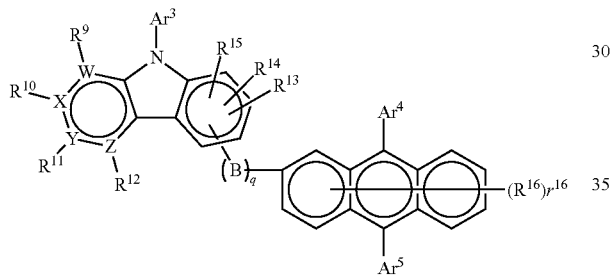

(2a)

wherein B, Ar$^3$ to Ar$^5$, R$^9$ to R$^{16}$, q, r$^{16}$, W, X, Y and Z are as described in the above general formula (2).

12. The organic electroluminescent device according to claim 11, wherein said electron-transporting compound is represented by the following general formula (2b),

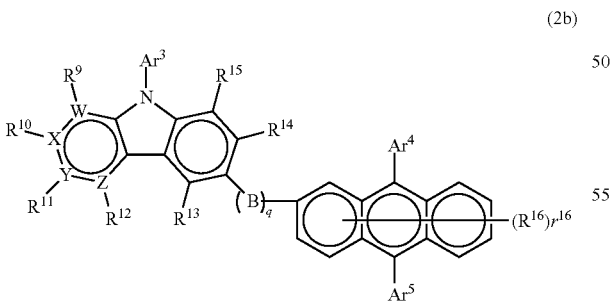

(2b)

wherein B, Ar$^3$ to Ar$^5$, R$^9$ to R$^{16}$, q, r$^{16}$, W, X, Y and Z are as described in the above general formula (2).

13. The organic electroluminescent device according to claim 12, wherein said electron-transporting compound is represented by the following general formula (2c),

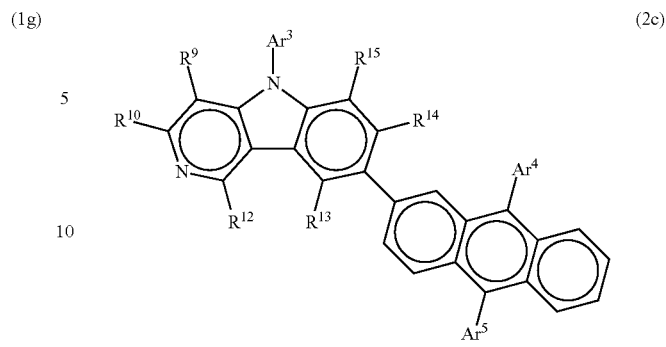

(2c)

wherein Ar$^3$ to Ar$^5$, R$^9$, R$^{10}$ and R$^{12}$ to R$^{15}$ are as described in the above general formula (2).

14. The organic electroluminescent device according to claim 12, wherein said electron-transporting compound is represented by the following general formula (2d),

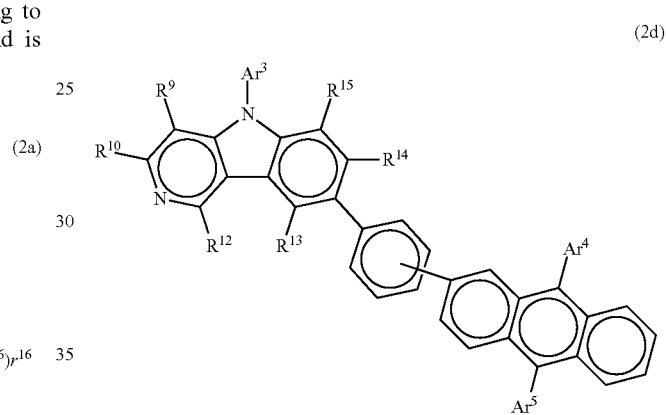

(2d)

wherein Ar$^3$ to Ar$^5$, R$^9$, R$^{10}$ and R$^{12}$ to R$^{15}$ are as described in the above general formula (2).

15. The organic electroluminescent device according to claim 12, wherein said electron-transporting compound is represented by the following general formula (2e),

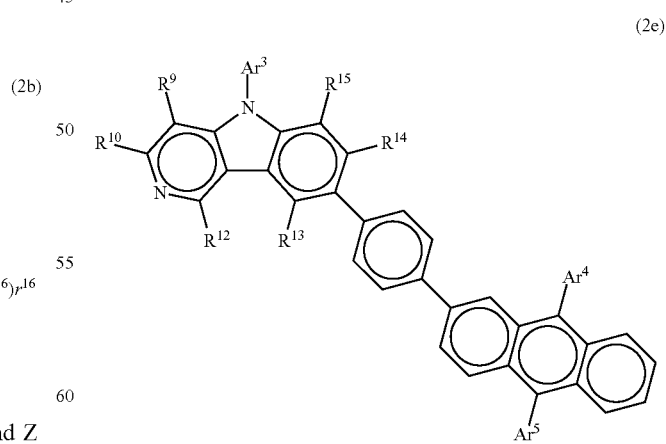

(2e)

wherein Ar$^3$ to Ar$^5$, R$^9$, R$^{10}$ and R$^{12}$ to R$^{15}$ are as described in the above general formula (2).

* * * * *